US007491811B2

(12) United States Patent
Meagher et al.

(10) Patent No.: US 7,491,811 B2
(45) Date of Patent: Feb. 17, 2009

(54) REPRESSOR-MEDIATED TISSUE-SPECIFIC GENE EXPRESSION IN PLANTS

(75) Inventors: Richard B. Meagher, Athens, GA (US); Rebecca S. Balish, Oxford, OH (US); Kim Tehryung, Athens, GA (US); Elizabeth C. McKinney, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 126 days.

(21) Appl. No.: 11/038,900

(22) Filed: Jan. 18, 2005

(65) Prior Publication Data

US 2005/0216976 A1 Sep. 29, 2005

Related U.S. Application Data

(60) Provisional application No. 60/537,275, filed on Jan. 15, 2004.

(51) Int. Cl.
C12N 15/82 (2006.01)
C07H 21/04 (2006.01)
A01H 5/00 (2006.01)

(52) U.S. Cl. ............. 536/24.1; 800/298; 800/287; 435/419

(58) Field of Classification Search ............... None
See application file for complete search history.

(56) References Cited

U.S. PATENT DOCUMENTS

| | | | |
|---|---|---|---|
| 5,110,732 | A | 5/1992 | Benfey et al. |
| 5,401,836 | A | 3/1995 | Baszczynski et al. |
| 5,459,252 | A | 10/1995 | Conkling et al. |
| 5,510,471 | A | 4/1996 | Lebrun et al. |
| 5,545,545 | A | 8/1996 | Gengenbach et al. |
| 5,633,363 | A | 5/1997 | Colbert et al. |
| 5,635,618 | A | 6/1997 | Capellades et al. |
| 5,641,876 | A | 6/1997 | McElroy et al. |
| 5,668,294 | A | 9/1997 | Meagher et al. |
| 5,808,034 | A | 9/1998 | Bridges et al. |
| 5,837,876 | A | 11/1998 | Conkling et al. |
| 5,962,769 | A | 10/1999 | Albertsen et al. |
| 5,965,796 | A | 10/1999 | Meagher et al. |
| 6,005,167 | A | 12/1999 | Van Tunen et al. |
| 6,172,279 | B1 | 1/2001 | Bridges et al. |
| 6,372,697 | B1 | 4/2002 | Mariani et al. |
| 6,384,304 | B1 | 5/2002 | Quandt et al. |
| 6,506,550 | B1 | 1/2003 | Fulton et al. |
| 6,518,483 | B1 | 2/2003 | Bruce et al. |
| 2002/0157129 | A1 | 10/2002 | Perez et al. |
| 2003/0135885 | A1 | 7/2003 | Lanahan et al. |
| 2003/0135888 | A1 | 7/2003 | Zhu et al. |
| 2004/0013658 | A1 | 1/2004 | Fulton et al. |
| 2005/0216976 | A1 | 9/2005 | Meagher et al. |

FOREIGN PATENT DOCUMENTS

| | | |
|---|---|---|
| WO | WO 93/25695 | 12/1993 |
| WO | WO 98/27201 | 6/1998 |
| WO | WO 98/39462 | 9/1998 |
| WO | WO 99/04023 | 1/1999 |
| WO | WO 01/29237 | 4/2001 |
| WO | WO 02/48335 | 6/2002 |
| WO | WO 03/066823 | 8/2003 |

OTHER PUBLICATIONS

Wilde et al. Control of gene expression in tobacco cells using a bacterial operator-repressor system (1992) EMBO Journal, vol. 11, pp. 1251-1259.*
Kyozuka et al. Light-regulated and Cell-specific expression of tomato rbcS-gusA and rice rbcS-gusA fusion genes in transgenic rice. (1993) Plant Physiology, vol. 102, pp. 991-1000.*
An et al. Strong, constitutive expression of the Arabidopsis ACT2/ACT8 actin subclass in vegetative tissues (1996) The Plant Journal, vol. 10, pp. 107-121.*
Rugh et al. Mercuric ion reduction and resistance in transgenic Arabidopsis thaliana plants expressing a modified bacterial merA gene. (1995) PNAS, vol. 93, pp. 3182-3187.*
Van der Zaal et al. Overexpression of a novel arabidopsis gene related to putative zinc-transporter genes from animals can lead to enhanced zinc resistance and accumulation. (1999) Plant Physiology, vol. 119, pp. 1047-1055.*
Wu et al. Disease resistance conferred by expression of a gene encoding H2O2-generating glucose oxidase in transgenic potato plants. (1995) The Plant Cell, vol. 7, pp. 1357-1368.*
Meagher et al. (2002) The Cytoskeletal Proteome of Arabidopsis. In; *Arabidopsis*, Meyerowitz et al. Eds., Invited Publication.
Meagher et al. (1996) "Phytoremediation of Heavy Metal Pollution: Ionic and Methyl Mercury," In; OECD Biotechnology for Water use and Conservation Workshop (Cocoyoc, Mexico: Organization for Economic Co-Operation and Development), pp. 305-321.
Moffatt et al. (1988) "Positive Selection for Male-Sterile Mutants of *Arabidopsis* Lacking Adenine Phosphoribosyl Transferase Activity," *Plant Physiol*. 86:1150-1154.

(Continued)

*Primary Examiner*—Cathy Kingdon Worley
(74) *Attorney, Agent, or Firm*—Greenlee, Winner and Sullivan, P.C.

(57) ABSTRACT

Plant tissue specific gene expression by way of repressor-operator complexes, has enabled outcomes including, without limitation, male sterility and engineered plants having root-specific gene expression of relevant proteins to clean environmental pollutants from soil and water. A mercury hyperaccumulation strategy requires that mercuric ion reductase coding sequence is strongly expressed. The actin promoter vector, A2pot, engineered to contain bacterial lac operator sequences, directed strong expression in all plant vegetative organs and tissues. In contrast, the expression from the A2pot construct was restricted primarily to root tissues when a modified bacterial repressor (LacIn) was coexpressed from the light-regulated rubisco small subunit promoter in above-ground tissues. Also provided are analogous repressor operator complexes for selective expression in other plant tissues, for example, to produce male sterile plants.

12 Claims, 17 Drawing Sheets

OTHER PUBLICATIONS

Murray et al. (1989) "Codon Usage in Plant Genes," *Nuc. Acids Res.* 17:477-498.

Nishimura et al. (1991) "A Constitutive Thiamine Metabolism Mutation, *thi80*, Causing Reduced Thiamine Pyrophosphokinase Activity, in *Saccharomyces cerevisiae*," *J. Bacteriol.* 173(8):2716-2719.

Nishimura et al. (1993) "THI3 Regulatory Protein, (*Saccharomyces cerevisiae*)," NCBI Accession No. BAA04886.

Nitz et al. (2001) "Pyk10, A Seedling and Root Specific Gene and Promoter from *Arabidopsis thaliana*," *Plant Sci.* 161:337-346.

Nosaka et al. (1993) "Isolation and Characterization of a Thiamin Pyrophosphokinase Gene, *THI80*, from *Saccharoyces cerevisiae*," *J. Biol. Chem.* 268(23):17440-17447.

Nosaka et al. (1993) "Thiamine pyrophosphokinase (TPK), (Thiamine kinase)," NCBI Accession No. P35202.

Pfahl (1979) "Tight-Binding Repressors of the Iac Operon: Selection System and in Vitro Analysis, " *J. Baceriol.* 137:137-145.

Preuss et al. (1994) "Tetrad Analysis Possible in Arabidopsis with Mutation of the Quartet (QRT) Genes," *Science* 264:1458-1460.

Rapala-Kozik et al. (1999) "Ligand-Protein Interaction in Plant Seed Thiamine-Binding Proteins. Binding of Various Thiamine Analogues to the Sepharose-Immobilized Buckwheat-Seed Protein," *J. Protein Chem.* 18:721-728.

Rugh et al. (1998) "Toxic Mercury Reduction and Remediation Using Transgenic Plants with a Modified Bacterial Gene," *Hort. Sci.* 33:618-621.

Rugh et al. (1998) "Development of Transgenic Yellow Poplar for Mercury Phytoremediation," *Nat. Biotechnol.* 16:925-928.

Rugh et al. (1996) "Mercury Ion Reduction and Resistance in Transgenic Arabidopsis thaliana Plants Expressing a Modified Bacterial merA Gene," *Proc. Natl. Acad. Sci. USA* 93:3182-3187.

Sabatini et al. (2003) "Scarecrow is Involved in Positioning the Stem Cell Niche in the Arabidopsis Root Meristem," *Genes Dev.* 17:354-358.

Sequence NP_579063 "Thiamine Phosphate Pyrophosphorylase", 2005.

Sequence NP_200288 "Thiazole Biosynthetic Enzyme, Chloroplast", 2005.

Sequence NP_189045 "Hydroxyethylthiazole Kinase Family Protein", 2005.

Sequence NP_173707 "Thiamin Biosynthesis Protein, Putative", 2005.

Sequence NP_172707 "Expressed Protein", 2005.

Sequence NP_015446 "Protein with Similarity to Hydroxymethylpyrimidine Phosphate Kinases", 2005.

Shirley et al. (1987) "5' Proximal Sequences of a Soybean Ribulose-1,5-Bisphosphate Carboxylase Small Subunit Gene Direct Light and Phytochrome Controlled Trascription," *Nuc. Acids Res.* 15:6501-6514.

Tanaka et al. (1990) "Enhancement of Foreign Gene Expression by a Dicot Intron in Rice But Not in Tobacco is Correlated with an Increased Level of mRNA and an Efficient Splicing of the Intron," *Nuc. Acids Res.* 18:6767-6770.

Tettelin et al. (1997) "Protein Required for Thiamine Biosynthesis and for Mitochondrial Genome Stability, (*Saccharomyces cerevisiae*)," NCBI Accession No. NP_011660.

Tsuchiya et al. (1995) "Tapetum-Specific Expression of the Gene for an Endo-β-1,3-Glucanase Causes Male Sterility in Transgenic Tobacco," *Plant Cell Physiol.* 36(3):487-494.

Ulmasov et al. (1997) "Regulated Expression of Plant tRNA Genes by the Prokaryotic tet and lac Repressors," *Plant Mol. Biol.* 35:417-424.

Watanabe et al. (1998) "Thiamin-Binding Protein from Sunflower Seeds," *J. Nutr. Sci. Vitaminol.* 44:665-672.

Watanabe et al. (1998) "Characterization of Thiamin-Binding Protein from Buckwheat Seeds," *J. Nutr. Sci. Vitaminol.* 44;323-328.

Wood et al. (2002) "Hypothetical Protein SPBC26H8.01, (*Schizosaccharomyces pombe* 972h-)," NCBI Accession No. NP_596642.

Xu et al. (1995) "*Bcp1*, A Gene Required for Male Fertility in Arabidopsis," *Proc. Natl. Acad. Sci. USA* 92:2106-2110.

Yamamoto et al. (1990) "Root-Specific Genes from Tobacco and *Arabidopsis Homologous* to an Evolutionary Conserved Gene Family of Membrane Channel Proteins," *Nuc. Acids Res.* 18:7449.

Yamamoto et al. (1991) "Characterization of Cis-Acting Sequences Regulating Root-Specific Gene Expression in Tobacco," *Plant Cell.* 3:371-382.

An et al. (1996) "Stron, Constitutive Expression of the Arabidopsis ACT2/ACT8 Actin Subclass In Vegetative Tissues," *Plant J.* 10:107-121.

Arabidopsis Genome Initiative (2000) "Analysis of the Genome Sequence of the Flowering Plant *Arabidopsis thaliana*," *Nature* 408:796-815.

Bariola et al. (1999) "Regulation of S-Like Ribonuclease Levels in Arabidopsis. Antisense Inhibition of *RNS1* or *RNS2* Elevates Anthocyanin Accumulation," *Plant Physiol.* 119:331-342.

Betz et al. (1986) "Base Substitution Mutants of the lac Operator: In Vivo and In Vitro Affinities for lac Repressor," *Gene* 50:123-132.

Bizily et al. (2003) "Subcellular Targeting of Methylmercury Lyase Enhances its Specific Activity for Organic Mercury Detoxification in Plants," *Plant Physiol.* 131:463-471.

Bizily, S. (2001) "Genetic Engineering of Plants with the Bacterial Genes merA and merB for the Phytoremediation of Methylmercury Contaminated Sediments," In, Genetics Department (Athens GA, University of GA), pp. 145.

Bizily et al. (2000) "Phytodetoxification of Hazardous Organomercurials by Genetically Engineered Plants," *Nat. Biotechnol.* 18:213-217.

Bizily et al. (1999) "Phytoremediation of Methylmercury Pollution: merB Expression in *Arabidopsis thaliana* Confers Resistance to Organomercurials," *Proc. Natl. Acad. Sci. USA* 96:6808-6813.

Blattner et al. (1997) "Hydroxyethylthiazole Kinase, (*Escherichia coli* K12)," NCBI Accession No. NP_416607.

Brown, S. (2001) "Cloning Vector pSB3616 Alkakine Phosphatase (phoA), lac Repressor (lacl), and Chloramphenicol acetyltransferase (cat) Genes, Complete cds," NCBI Accession No. AY042185.

Brown et al. (1987) "Biosynthesis of Folic Acid, Roboflavin, Thiamine, and Pantothenic Acid," In; *Escherichia Coli and Salmonella Typhimurium*, Neidhardt, F. ed., Washington, DC: American Society for Microbiology, pp. 521-538.

Bussey et al. (1997) "Bifunctional Enzyme with Thiamine-phosphate Pyrophosphorylase and 4-methyl-5-beta-hydroxyethythiazole Kinase Activities, Required for Thiamine Biosynthesis; GFP=Fusion Protein Localizes to the Cytoplasm in a Punctate Pattern, (*Saccharomyces cerevisiae*)," Sequence NP_015110.

Chabregas et al. (2001) "Dual Targeting Properties of the N-Terminal Signal Sequence of *Arabidopsis Thaliana THI1* Protein to Mitochondria and Chloroplasts," *Plant Mol. Biol.* 46:639-650.

Chang et al. (1999) "Aspastate-27 and Glutamate-473 are Involved in Catalysis by *Zymomonas mobilis* Pyruvate Decarboxylase," *Biochem. J.* 339(2):255-260.

Chuang et al. (2000) "Specific and Heritable Genetic Interference by Double-Stranded RNA in *Arabidopsis thaliana*," *Proc Natl. Acad. Sci. USA* 97:4985-4990.

Conkling et al. (1990) "Isolation of Transcriptionally Regulated Root-Specific Genes from Tobacco," *Plant Physiol.* 93:1203-1211.

Dhankher et al. (Nov. 2002) "Engineering Tolerance and Hyperaccumulation of Arsenic in Plants by Combining Arsenate Reductase and Gamma-Glutamylcysteine Synthetase Expression," *Nat. Biotechnol.* 20:1140-1145.

Falcon et al. (2000) "Operator DNA Sequence Variation Enhances High Affinity Binding by Hinge Helix Mutants of Lactose Repressor Protein," *Biochem.* 39:11074-11083.

Fuerst et al. (1989) "Transfer of the Inducible lac Repressor/Operator System from *Escherichia coli* to a Vaccinia Virus Expression Vector," *Proc. Natl. Acad. Sci USA* 86:2549-2553.

Gao et al. (2000) "Fungal Pathogen Protection in Potato by Expression of a Plant Defensin Peptide," *Nat. Biotechnol.* 18:1307-1310.

Goddeimeier et al. (1998) "Root Specific Expression of a Zea Mays Gene Encoding a Novel Glycine-Rich Protein, zmGRP3," *Plant Mol. Biol.* 36:799-802.

Goldfarb et al. (1986) "Synthetic Peptides as Nuclear Localization Signals," *Nature* 322:641-644.

Goffeau et al. (1996) "Thi2p, (*Saccharomyces cervisiae*)," NCBI Accession No. NP_009799.
Hayashi et al. (2001) "ThiE, (*Escherichia coli* 0157:H7)," NCBI Accession No. NP_312943.
Heaton et al. (1998) "Phytoremediation of Mercury and Methylmercury Polluted Soils Using Genetically Engineered Plants," *J. Soil Contam.* 7:497-509.
Held et al. (1993) "An mRNA Putatively Coding for an O-Methyltransferase Accumulates Preferentially in Maize Roots and is Located Predominantly in the Region of the Endodermis," *Plant Physiol.* 102:1001-1008.
Held et al. (1997) "Zrp2: A Novel Maize Gene Whose mRNA Accumulates in the Root Cortex and Mature Stems," *Plant. Mol. Biol.* 35:367-375.
Hu et al. (1990) "A Combination of Depression of the lac Operator-Repressor System with Positive Induction by Glucocorticoid and Metal ions Provides a High-Level-Inducible Gene Expression System Based on the Human Metallothionein-IIA Promoter," *Mol. Cell. Biol.* 10:6141-6151.
Huang et al. (1996) "The *Arabidopsis thaliana* ACT4/ACT12 Actin Gene Subclass is Strongly Expressed Throughout Pollen Development," *Plant J.* 10(2):189-202.
Iqbal et al. (2002) "A Pyramid of Loci for Partial Resistance to Fusarium solani f. sp. Glycines Maintains Myo-Inositol-1-Phosphate Synthase Expression in Soybean Roots," *Theor. Appl. Genet.* 105:1115-1123.
Jefferson et al. (1987) "GUS Fusions: B-Glucuronidase as a Sensitive and Versitile Gene Fusion Marker in Higher Plants," *EMBO J.* 6:3901-3907.
Kandasamy et al. (Mar. 2003) "Cell Cycle-Dependant Association of Arabidopsis Actin-Related Proteins AtARP4 and AtARP7 with the Nucleus," *Plant J.* 33:393-348.
Kandasamy et al. (Jan. 2002) "Functional Non-Equivalency of Actin Isovariants in Arabidopsis," *Mol. Biol. Cell* 13:251-261.
Kandasamy et al. (1999) "The Late Pollen-Specific Actins in Angiosperms," *Plant J.* 18:681-691.
Kellermann et al. (1990) "Pyruvate decarboxylase Isozyme 1," NCBI Accession No. PO6169.
Kursteiner et al. (Jun. 2003) "The *Pyruvate decarboxylase 1* Gene of Arabidopsis Is Required During Anoxia but not Other Environmental Stresses," *Plant Physiol.* 132:968-978.
Lauter, F.R. (1996) "Root Specific Expression of the LeRse-1 Gene in Tomato is Induced by Exposure of the Shoot to Light," *Mol. Gen. Genet.* 252:751-754.
Ledoux et al. (1974) "DNA-Mediated Genetic Correction of Thiamineless *Arabidopsis thaliana*," *Nature* 249:17-21.
Li et al. (1969) "Thiamine Mutants of the Crucifer, Arabidopsis," *Biochem. Genet.* 3:163-170.
Machado et al. (1996) "Thi1, A Thiamine Biosynthetis Gene in *Arabidopsis thaliana*, Complements Bacterial Defects in DNA Repair," *Plant Mol. Biol.* 31:585-593.
Machado et al. (1997) "Dual Role for the Yeast Thi4 Gene in Thiamine Biosynthesis and DNA Damage Tolerance," *J. Mol. Biol.* 273:114-121.
Manetti et al. (1994) "*nmt2* of Fission Yeast: A Second Thiamine-Repressible Gene Co-Ordinately Regulated with *nmt1i*," *Yeast* 10:1075-1082.
Mariani et al. (1992) "A Chimaeric Ribonuclease-Inhibitor Gene Restores Fertility to Male Sterile Plants," *Nature* 357:384-387.
McDowell et al. (1996) "The Arabidopsis ACT7 Actin Gene is Expressed in Rapidly Developing Tissues and Responds to Several External Stimuli." *Plant Physiol.* 111:699-711.
McKinney et al. (Mar. 2002) "Arabidopsis Contains Ancient Classes of Differentially Expressed Actin-Related Protein Genes," *Plant Physiol.* 128:997-1007.
McKinney et al. (2001) "Small Changes in the Regulation of One Arabidopsis Profilin Isovariant, PRF1, Alter Seedling Development," *Plant Cell* 13:1179-1191.
Meagher, R.B. (2000) "Phytoremediation of Toxic Elemental and Organic Pollutants," *Curr. Opin. Plant. Biol.* 3:153-162.

Meagher et al. (2002) The Cytoskeletal Proteome of Arabidopsis. In; *Arabidopsis*, Meyerowitz et al. Eds., Invited Publication.
Meagher et al. (1996) "Phytoremediation of Heavy Metal Pollution: Ionic and Methyl Mercury," In; OECD Biotechnology for Water use and Conservation Workshop (Cocoyoc, Mexico: Organization for Economic Co-Operation and Development), pp. 305-321.
Moffatt et al. (1988) "Positive Selection for Male-Sterile Mutants of *Arabidopsis* Lacking Adenine Phosphoribosyl Transferase Activity," *Plant Physiol.* 86:1150-1154.
Murray et al. (1989) "Codon Usage in Plant Genes," *Nuc. Acids Res.* 17:477-498.
Nishimura et al. (1991) "A Constitutive Thiamine Metabolism Mutation, *thi80*, Causing Reduced Thiamine Pyrophosphokinase Activity, in *Saccharomyces cerevisiae*," *J. Bacteriol.* 173(8):2716-2719.
Nishimura et al. (1993) "THI3 Regulatory Protein, (*Saccharomyces cerevisiae*)," NCBI Accession No. BAA04886.
Nitz et al. (2001) "Pyk10, A Seedling and Root Specific Gene and Promoter from Arabidopsis thaliana," *Plant Sci.* 161:337-346.
Nosaka et al. (1993) "Isolation and Characterization of a Thiamin Pyrophosphokinase Gene, *THI80*, from *Saccharoyces cerevisiae*," *J. Biol. Chem.* 268(23):17440-17447.
Nosaka et al. (1993) "Thiamine pyrophosphokinase (TPK), (Thiamine kinase)," NCBI Accession No. P35202.
Pfahl (1979) "Tight-Binding Repressors of the lac Operon: Selection System and in Vitro Analysis," *J. Bacteriol.* 137:137-145.
Preuss et al. (1994) "Tetrad Analysis Possible in Arabidopsis with Mutation of the Quartet (QRT) Genes," *Science* 264:1458-1460.
Rapala-Kozik et al. (1999) "Ligand-Protein Interaction in Plant Seed Thiamine-Binding Proteins. Binding of Various Thiamine Analogues to the Sepharose-Immobilized Buckwheat-Seed Protein," *J. Protein Chem.* 18:721-728.
Rugh et al. (1998) "Toxic Mercury Reduction and Remediation Using Transgenic Plants with a Modified Bacterial Gene," Hort. Sci. 33:618-621.
Rugh et al. (1998) "Development of Transgenic Yellow Poplar for Mercury Phytoremediation," Nat. Biotechnol. 16:925-928.
Rugh et al. (1996) "Mercury Ion Reduction and Resistance in Transgenic *Arabidopsis thaliana* Plants Expressing a Modified Bacterial merA Gene," *Proc. Natl. Acad. Sci. USA* 93:3182-3187.
Sabatini et al. (2003) "Scarecrow is Involved in Positioning the Stem Cell Niche in the Arabidopsis Root Meristem," *Genes Dev.* 17:354-358.
Sequence NP_579063 "Thiamine Phosphate Pyrophosphorylase".
Sequence NP_200288 "Thiazole Biosynthetic Enzyme, Chloroplast".
Sequence NP_189045 "Hydroxyethylthiazole Kinase Family Protein".
Sequence NP_173707 "Thiamin Biosynthesis Protein, Putative".
Sequence NP_172707 "Expressed Protein".
Sequence NP_015446 "Protein with Similarity to Hydroxymethylpyrimidine Phosphate Kinases".
Shirley et al. (1987) "5' Proximal Sequences of a Soybean Ribulose-1,5-Bisphosphate Carboxylase Small Subunit Gene Direct Light and Phytochrome Controlled Transcription," *Nuc. Acids Res.* 15:6501-6514.
Tanaka et al. (1990) "Enhancement of Foreign Gene Expression by a Dicot Intron in Rice But Not in Tobacco is Correlated with an Increased Level of mRNA and an Efficient Splicing of the Intron," *Nuc. Acids Res.* 18:6767-6770.
Tettelin et al. (1997) "Protein Required for Thiamine Biosynthesis and for Mitochondrial Genome Stability, (*Saccharomyces cerevisiae*)," NCBI Accession No. NP_011660.
Tsuchiya et al. (1995) "Tapetum-Specific Expression of the Gene for an Endo-β-1,3-Glucanase Causes Male Sterility in Transgenic Tobacco," *Plant Cell Physiol.* 36(3):487-494.
Ulmasov et al. (1997) "Regulated Expression of Plant tRNA Genes by the Prokaryotic tet and lac Repressors," *Plant Mol. Biol.* 35:417-424.
Watanabe et al. (1998) "Thiamin-Binding Protein from Sunflower Seeds," *J. Nutr. Sci. Vitaminol.* 44:665-672.
Watanabe et al. (1998) "Characterization of Thiamin-Binding Protein from Buckwheat Seeds," *J. Nutr. Sci. Vitaminol.* 44;323-328.

Wood et al. (2002) "Hypothetical Protein SPBC26H8.01, (*Schizosaccharomyces pombe* 972h-)," NCBI Accession No. NP_596642.

Xu et al. (1995) "*Bcp1*, A Gene Required for Male Fertility in *Arabidopsis*," *Proc. Natl. Acad. Sci. USA* 92:2106-2110.

Yamamoto et al. (1990) "Root-Specific Genes from Tobacco and Arabidopsis Homologous to an Evolutionary Conserved Gene Family of Membrane Channel Proteins," *Nuc. Acids Res.* 18:7449.

Yamamoto et al. (1991) "Characterization of Cis-Acting Sequences Regulating Root-Specific Gene Expression in Tobacco," *Plant Cell.* 3:371-382.

Wilde et al. (1992) "Control of gene expression in tobacco cells using a bacterial operator—repressor system," The EMBO J. 11:1251-1259.

* cited by examiner

Fig. 2A-1

```
  1 TCATTATGTA AGAAAGTTTT GACGAATATG GCACGACAAA ATGGCTAGAC

51 TCGATGTAAT TGGTATCTCA ACTCAACATT ATACTTATAC CAAACATTAG

101 TTAGACAAAA TTTAAACAAC TATTTTTTAT GTATGCAAGA GTCAGCATAT

151 GTATAATTGA TTCAGAATCG TTTTGACGAG TTCGGATGTA GTAGTAGCCA

201 TTATTTAATG TACATACTAA TCGTGAATAG TGAATATGAT GAAACATTGT

251 ATCTTATTGT ATAAATATCC ATAAACACAT CATGAAAGAC ACTTTCTTTC

301 ACGGTCTGAA TTAATTATGA TACAATTCTA ATAGAAAACG AATTAAATTA

351   CGTTGAATTG TATGAAATCT AATTGAACAA GCCAACCACG ACGACGACTA

401   ACGTTGCCTG GATTGACTCG GTTTAAGTTA ACCACTAAAA AAACGGAGCT

451   GTCATGTAAC ACGCGGATCG AGCAGGTCAC AGTCATGAAG CCATCAAAGC

501   AAAAGAACTA ATCCAAGGGC TGAGATGATT AATTAGTTTA AAAATTAGTT

551   AAAAGAACTA ATCCAAGGGC TGAGATGATT AATTAGTTTA AAAATTAGTT

601   AACACGAGGG AAAAGGCTGT CTGACAGCCA GGTCACGTTA TCTTTACCTG

651   TGGTCGAAAT GATTCGTGTC TGTCGATTTT AATTATTTTT TTGAAAGGCC

701   GAAAATAAAG TTGTAAGAGA TAAACCCGCC TATATAA gtggaattgtgag 751   cggataacaatt GAATTGTC TCGTTGTCCT CCTCACTTTC ATCAGCCGTT
                    ts start sites
    801   TTGAATCTCC GGCGACTTGA CAGAGAAGAA CAAGGAT gtggaattgtgag
```

Fig. 2A-2

```
851  cggataacaatt TAATCCAG GAGATTCATT CTCCGTTTTG AATCTTCCTC

901  AATCTCATCT TCTTCCGCTC TTTCTTTCCA AGGTAATAGG AACTTTCTGG

951  ATCTACTTTA TTTGCTGGAT CTCGATCTTG TTTTCTCAAT TTCCTTGAGA

1001 TCTGGAATTC GTTTAATTTG GATCTGTGAA CCTCCACTAA ATCTTTTGGT

1051 TTTACTAGAA TCGATCTAAG TTGACCGATC AGTTAGCTCG ATTATAGCTA

1101 CCAGAATTTG GCTTGACCTT GATGGAGAGA TCCATGTTCA TGTTACCTGG

1151 GAAATGATTT GTATATGTGA ATTGAAATCT GAACTGTTGA AGTTAGATTG

1201 AATCTGAACA CTGTCAATGT TAGATTGAAT CTGAACACTG TTTAAGGTTA

1251 GATGAAGTTT GTGTATAGAT TCTTCGAAAC TTTAGGATTT GTAGTGTCGT

1301 ACGTTGAACA GAAAGCTATT TCTGATTCAA TCAGGGTTTA TTTGACTGTA

1351 TTGAACTCTT TTTGTGTGTT TGCAGCTCATAAA CCATGG GGGCCC CTCGAG
                                          Ncol*  Apa1   Xhol
1401 GCATGC GTCGAC AAGCTT GATATC CCCGGG GGATCC TCTAGA CTCGGAG
     Sphl*  Sall   HindIII EcoRV Smal*  EcoRI* Xbal
1451 GCTCTCAAGA TCAAAGGCTT AAAAAGCTGG GGTTTTATGA ATGGGATCAA

1501 AGTTTCTTTT TTTCTTTTAT ATTTGCTTCT CCATTTGTTT GTTTCATTTC

1551 CCTTTTTGTT TTCGTTTCTA TGATGCACTT GTGTGTGACA AACTCTCTGG

1601 GTTTTTACTT ACGTCTGCGT TTCAAAAAAA AAAACCGCTT TCGTTTTGCG

1651 TTTTAGTCCC ATTGTTTTGT AGCTCTGAGT GATCGAATTG ATGCCTCTTT

1701 ATTCCTTTTG TTCCCTATAA TTTCTTTCAA AACTCAGAAG AAAAACCTTG
```

Fig. 2A-3

```
1751 AAACTCTTTG CAATGTTAAT ATAAGTATTG TATAAGATTT TTATTGATTT

1801 GGTTATTAGT CTTACTTTTG CTACCTCCAT CTTCACTTGG AACTGATATT

1851 CTGAATAGTT AAAGCGTTAC ATGTCTTCCA TTCACAAATG AACTTAAACT

1901 AGCACAAAGT CAGATATTTT AAGACCGCGG TGGAGCTC
```

Fig. 2B-1

```
  1 ATGGGTAAAC CAGTAACGTT ATACGATGTC GCAGAGTATG CCGGTGTCTC

51 TTATCAGACC GTTTCCCGCG TGGTGAACCA GGCCAGCCAC GTTTCTGCGA

101 AAACGCGGGA AAAAGTGGAA GCGGCGATGG CGGAGCTGAA TTACATTCCC

151 AACCGCGTGG CACAACAACT GGCGGGCAAA CAGTCGTTGC TGATTGGCGT

201 TGCCACCTCC AGTCTGGCCC TGCACGCGCC GTCGCAAATT GTCGCGGCGA

251 TTAAATCTCG CGCCGATCAA CTGGGTGCCA GCGTGGTGGT GTCGATGGTA

301 GAACGAAGCG GCGTCGAAGC CTGTAAAGCG GCGGTGCACA ATCTTCTCGC

351     GCAACGCGTC AGTGGGCTGA TCATTAACTA TCCGCTGGAT GACCAGGATG

401 CCATTGCTGT GGAAGCTGCC TGCACTAATG TTCCGGCGTT ATTTCTTGAT

451 GTCTCTGACC AGACACCCAT CAACAGTATT ATTTTCTCCC ATGAAGACGG

501 TACGCGACTG GGCGTGGAGC ATCTGGTCGC ATTGGGTCAC CAGCAAATCG

551 CGCTGTTAGC GGGCCCATTA AGTTCTGTCT CGGCGCGTCT GCGTCTGGCT

601 GGCTGGCATA AATATCTCAC TCGCAATCAA ATTCAGCCGA TAGCGGAACG

651 GGAAGGCGAC TGGAGTGCCA TGTCCGGTTT TCAACAAACC ATGCAAATGC

701 TGAATGAGGG CATCGTTCCC ACTGCGATGC TGGTTGCCAA CGATCAGATG

751 GCGCTGGGCG CAATGCGCGC CATTACCGAG TCCGGGCTGC GCGTTGGTGC

801 GGATATCTCG GTAGTGGGAT ACGACGATAC CGAAGACAGC TCATGTTATA
```

Fig. 2B-2

```
 851  TCCCGCCGTT AACCACCATC AAACAGGATT TTCGCCTGCT GGGGCAAACC

901   AGCGTGGACC GCTTGCTGCA ACTCTCTCAG GGCCAGGCGG TGAAGGGCAA

951  TCAGCTGTTG CCCGTCTCAC TGGTGAAAAG AAAAACCACC CTGGCGCCCA

1001  ATACGCAAAC CGCCTCTCCC CGCGCGTTGG CCGATTCATT AATGCAGCTG

1051  GCACGACAGG TTTCCCGACT GGAAAGCGGGCAG TCT TCT GTT GTT CAT
                                           -----------------
1101       CCT AAG AAG AAG AGA AAG GTT TGA
           -------NLS----------------- stop
```

Fig. 2C

```
  1 MGKPVTLYDV AEYAGVSYQT VSRVVNQASH VSAKTREKVE AAMAELNYIP

51 NRVAQQLAGK QSLLIGVATS SLALHAPSQI VAAIKSRADQ LGASVVVSMV

101 ERSGVEACKA AVHNLLAQRV SGLIINYPLD DQDAIAVEAA CTNVPALFLD

151 VSDQTPINSI IFSHEDGTRL GVEHLVALGH QQIALLAGPL SSVSARLRLA

201 GWHKYLTRNQ IQPIAEREGD WSAMSGFQQT MQMLNEGIVP TAMLVANDQM

251 ALGAMRAITE SGLRVGADIS VVGYDDTEDS SCYIPPLTTI KQDFRLLGQT

301 SVDRLLQLSQ GQAVKGNQLL PVSLVKRKTT LAPNTQTASP RALADSLMQL

351 ARQVSRLESGQ SSVVHPKKKRKV *
             ---NLS------
```

Fig. 2D-1

```
  1 ATGGGTAGCA CTCTCAAGAT CACTGGTATG ACTTGTGACT CTTGTGCAGT

51 GCATGTCAAG GATGCACTGG AGAAAGTTCC AGGTGTGCAA TCTGCTGATG

101 TGAGCTATGC AAAGGGCTCT GCCAAATTGG CCATTGAAGT TGGCACTTCT

151 CCAGATGCAC TTACTGCTGC TGTTGCAGGT CTGGGCTATC GTGCTACTCT

201 TGCAGATGCA CCATCTGTGT CTACTCCAGG TGGTCTGCTT GATAAGATGC

251 GTGACCTGCT TGGTCGTAAT GACAAGACTG GGAGCTCTGG TGCACTCCAC

301 ATTGCTGTGA TTGGCTCTGG TGGTGCAGCA ATGGCAGCAG CACTTAAAGC

351 TGTTGAACAA GGTGCTCGTG TGACTCTGAT GAACGTGGC ACTATTGGTG

401 GCACTTGTGT TAATGTTGGT TGTGTGCCAA GCAAGATCAT GATTCGTGCT

451 GCTCACATTG CTCATCTTCG TCGTGAATCT CCATTTGATG GTGGCATTGC

501 TGCAACCACT CCAACCATTC AACGTACTGC ACTCCTTGCA CAACAACAAG

551 CACGTGTTGA TGAACTTCGT CATGCAAAGT ATGAAGGTAT TCTTGAAGGT

601 AACCCAGCCA TCACTGTGCT TCATGGCTCT GCACGTTTCA AGGACAACCG

651 TAACCTCATT GTTCAACTTA ATGATGGTGG TGAACGTGTG GTGGCTTTTG

701 ACCGCTGTCT CATTGCCACT GGTGCAAGCC CAGCTGCTCC ACCAATTCCT

751 GGTCTCAAGG ACACTCCTTA CTGGACTTCC ACTGAAGCAC TAGTGTCTGA

801 GACCATTCCA AAGCGTCTTG CAGTCATTGG CTCCTCTGTG GTGGCTCTTG

851 AACTTGCCCA GGCCTTTGCA CGTCTTGGTG CTAAAGTGAC CATTCTCGCA
```

Fig. 2D-2

```
 901 CGCTCCACTC TCTTCTTTCG TGAAGACCCA GCTGTAGGTG AAGCTGTTAC

951 TGCTGCATTT CGCATGGAAG GTATTGAAGT GCGTGAGCAT ACTCAAGCAA

1001 GCCAAGTTGC CTATATCAAT GGTGAAGGTG ATGGTGAATT CGTCCTTACC

1051 ACTGCTCATG GTGAACTTCG TGCAGACAAA CTCCTTGTTG CAACTGGTCG

1101 TGCACCAAAC ACTCGCAAAC TGGCACTTGA TGCAACTGGT GTGACCCTTA

1151 CTCCACAAGG TGCTATTGTG ATTGATCCAG GTATGCGTAC CTCTGTGGAA

1201 CACATCTATG CAGCTGGTGA TTGCACTGAT CAACCACAAT TTGTGTATGT
```

Fig. 2D-3

```
1251  TGCTGCTGCT GCTGGTACAC GTGCTGCTAT CAACATGACT GGTGGCGATG

1301  CTGCCCTCAA CCTGACCGCG ATGCCGGCCG TGGTGTTCAC CGACCCGCAA

1351  GTGGCGACCG TGGGCTACAG CGAGGCGGAG GCGCACCATG ACGGCATCAA

1401  AACTGATAGT CGCACGCTAA CGCTGGACAA CGTGCCGCGC GCGCTCGCCA

1451  ACTTCGACAC GCGCGGCTTC ATCAAACTGG TGGTTGAAGA AGGCAGCGGA

1501  CGACTGATCG GCGTGCAGGC AGTGGCCCCG GAAGCGGGCG AACTGATCCA

1551  GACGGCCGCA CTGGCGATTC GCAACCGGAT GACGGTGCAG GAACTGGCCG

1601  ACCAGTTATT CCCCTACCTG ACGATGGTCG AAGGGTTGAA GCTCGCGGCG

1651  CAGACCTTCA ACAAGGATGT GAAGCAGCTT TCCTGCTGCG CCGGGTGA
```

Fig. 3A-3K
GUS expression patterns of Columbia, Act2pot::GUS, and LacI+LacO-GUS
Columbia (wildtype)
Act2pot::GUS
LacI+LacO-GUS
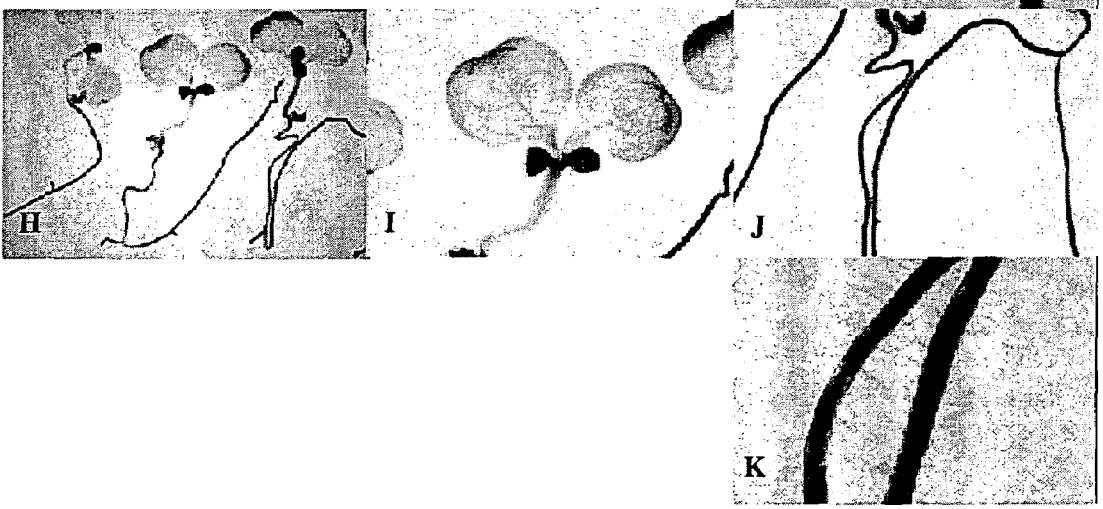

REPRESSOR-MEDIATED TISSUE-SPECIFIC GENE EXPRESSION IN PLANTS

CROSS REFERENCE TO RELATED APPLICATIONS

This application claims benefit of U.S. Provisional Application 60/537,275, filed Jan. 15, 2004, which is incorporated herein to the extent there is no inconsistency with the present application.

ACKNOWLEDGMENT OF FEDERAL RESEARCH SUPPORT

This invention was made, at least in part, with funding from the United States Department of Agriculture under contract No. 2001-35100-10652, the Department of Energy EMSP Grant No. DE-FG07-02ER63493 and National Institutes of Health under Grant No. GM 36397-18. Accordingly, the U.S. Government has certain rights in this invention.

BACKGROUND OF THE INVENTION

The field of this invention is plant molecular biology. In particular, the invention relates to chimeric transcription regulatory sequences which promote target gene expression in a particular plant tissue, for example in root tissue or in reproductive tissue, by coupling regulatory elements of the bacterial lac operon with a strong plant promoter of choice.

There is a longfelt need in the art for organ-specific and tissue-specific plant regulatory systems, and especially for strong, tightly controlled root-specific transcriptional expression systems and for tightly controlled expression systems for other plant tissues, including reproductive tissue, such that controlled plant gene expression, including determination of conditional sterility, can be achieved. There is also a need in the art for phytoremediation strategies with improved sequestration of the target environmental pollutant, for example, mercury.

SUMMARY OF THE INVENTION

The present invention provides for organ- and tissue-specific expression of a coding or other functional target sequence of interest in a plant, especially root-specific expression of that target sequence. In a particular specifically exemplified embodiment for root-specific expression, a repressor, for example, the Lac repressor protein or a derivative thereof, especially a nuclear-targeted derivative, is expressed under the regulatory control of a plant promoter, which is selectively functional in aboveground plant tissue. Examples of such promoters are the light-regulated SRS1 promoter, such as that from *Arabidopsis thaliana* or *Glycine max* or any other plant known in the art, or a light-regulated promoter such as that driving expression of the CAB protein of a plant or any other known to the art. The coding or other functional target sequence of interest is operably linked to a promoter functional in a plant, which promoter comprises an operator sequence, which specifically binds the cognate repressor. The promoter is modified (made chimeric) to contain the binding site (operator sequence) for the repressor protein. When both of these constructs are introduced into and incorporated within a plant cell and a transgenic plant is produced from that cell, the repressor protein is synthesized in the above ground plant tissues and binds to the corresponding operator sequence within the transcriptional regulatory sequence operably linked to the coding or other functional target sequence in those above ground tissues, effectively preventing expression of the coding or other functional target sequence in those above ground tissues. In the below ground tissue, i.e., the root, the repressor protein is not expressed and the coding or other functional target sequence is expressed. A suitable (and well-characterized) repressor is that of the *Escherichia coli* lac operon, and the operator (repressor binding region) of the *Escherichia coli* lac operon is also well characterized and suitable.

While the invention has been specifically exemplified as a root-specific expression system, it is also possible to construct a chimeric repressor gene where its expression is under the control of a different tissue-specific or organ-specific promoter, with the result that the target sequence is expressed in the tissue and/or organs where the repressor is not expressed. For example, root-specific transcription regulatory sequences are known; the use of a root-specific promoter to drive expression of the repressor protein results in expression of the target sequence in plant tissues other than root; i.e., in above-ground tissues and organs. Alternatively, expression specifically in reproductive tissue can also be achieved via the appropriate choices of regulatory sequences, with conditional male and/or female sterility being possible.

Also within the scope of the invention are transgenic plants in which expression of a target sequence is effected by induction of an environmentally or chemically regulated chimeric target coding or other functional sequence. For example, IPTG or lactose can be used to release the repressor from the operator associated with the chimeric target gene in the tissues or organ to which IPTG or lactose is applied, when the operator and repressor are those of the lac operon.

Also within the scope of the present invention is a nucleic acid construct (which does not occur in nature) which comprises a repressor coding sequence operably linked to an organ- or tissue-specific promoter functional in a plant or to an environmentally inducible promoter (for example, inducible by light, but not requiring the application of an exogenous chemical signal) and a construct comprising a coding or other functional target sequence of interest operably linked to a promoter functional in a plant and to an operator sequence which binds the repressor protein, with the result that transcription of the associated coding or other functional target sequence is prevented. In the absence or repressor protein, for example, in organs and/or tissues in which the organ- or tissue-specific or environmentally regulated promoter is not functional, the coding or other functional target sequence of interest is transcribed. Plant vectors which comprise these constructs and which are useful for introducing these constructs into a plant cell are also within the scope of the present invention, as are transgenic plants and seeds and progeny, including seeds of the progeny plants, which contain the particular chimeric repressor and transcriptional regulatory sequences of the present invention.

The present invention generally provides methods for directing organ- or tissue-specific expression of a coding or other functional target sequence of interest in a transgenic plant. The constructs described above are introduced into the genome of a plant cell, and a transgenic plant is produced therefrom. As specifically exemplified herein, root-specific expression of a coding sequence or other functional target sequence of interest is achieved. The lac repressor or a derivative which is efficiently translocated into the nucleus of the transgenic plant cell (the lacIn repressor, nuclear-targeted repressor) is expressed in above ground plant tissue to prevent the expression of a coding or other functional target sequence operably linked to a plant expressible promoter which has been modified to contain a lac operator sequence, desirably a tandem lac operator sequence so that transcription is prevented in cells in which the lac repressor is expressed. The promoter into which the lac operator sequence, for example, 5'GTGGAATTGT GAGCGGATAA CAATT-3', SEQ ID NO:16, can be that of the constitutive, *Arabidopsis thaliana* Act2 promoter.

It is a further object of the invention to provide a Lac repressor protein which is targeted to the nucleus of a eukaryotic cell. As specifically exemplified, the NLS is SSVVHP-KKKRKV (SEQ ID NO:9), and the coding and amino acid sequences of the LacIn protein are given in FIGS. 2B and 2C, and in SEQ ID NO:10 and SEQ ID NO:11, respectively.

In another specifically exemplified embodiment of the invention, there are provided methods and genetic constructs for tissue specific (regulated) gene expression in plant reproductive tissue, e.g., male reproductive tissue, genetically modified plants, plant parts, plant cells and seeds containing such constructs within the genome of those plants, parts, cells and seeds. As specifically exemplified, the repressor-operator system is the lacI-lacO system, where the operator sequences are incorporated within a reproductive-specific promoter, for example, the A12 (actin 12) promoter which is selectively expressed in anther, and where a deleterious gene is expressed under the regulatory control of that tissue-specific promoter. The deleterious gene is one whose expression results in a male sterile (or female sterile) phenotype; it can be any of a variety of deleterious genes which prevent pollen production, when the goal is male sterility and the target tissue is anthers. As specifically exemplified, the deleterious gene is one which results in starvation of the tissue for thiamine; e.g., a high affinity thiamine binding protein or it can be a gene encoding an RNAi molecule which results in the destruction of mRNA encoding a thiamine biosynthetic enzymes such as the bifunctional enzyme (phosphomethylpyrimidine kinase, thiamine phosphate pyrophosphorylase also called thiamine synthase) and a monofunctional enzyme (hydroxyethylthiazole kinase) (Thi2 or Thi3). To obtain functional gene expression in the particular tissue resulting from a genetic cross, the cognate repressor coding sequence is operably linked to a promoter functional in that same tissue, with the result that the repressor turns off expression of the deleterious gene, allowing fertility. Genetic segregation of the repressor gene away from the deleterious gene results in sterility. Controlled expression can be effected in other tissues by the use of promoters, operators and repressors in an analogous fashion.

DESCRIPTION OF THE DRAWINGS

FIG. 1A shows a phytoremediation strategy for mercury. Ionic mercury (Hg(II)) extracted from soil enters the roots and is electrochemically reduced to Hg(0) by the bacterial mercuric ion reductase (MerA). Hg(0) is a moderately soluble gas and is transported aboveground along with waste gases like $CO_2$ and $O_2$. There, reactive Hg(0) can be transpired from leaves, or it is reoxidized to Hg(II) by the action of endogenous plant peroxidases and catalases and trapped in thiol compounds. FIG. 1B shows construction of a strong, root-specific promoter based on leaf repression of a modified constitutive actin promoter. The modified LacIn repressor protein contains a NLS and is expressed from the strong light-induced promoter cassette, S1pt. The constitutive actin ACT2 promoter cassette was modified to contain two bacterial lacO operator sequences, the binding sites for LacIn, making the A2pot cassette. A2pot is used to express GUS (β-glucuronidase) and merA. When these two transgenes are coexpressed in leaves, the lacIn protein enters the nucleus and represses A2pot::GUS or A2pot::merA activity. In roots there is no repressor expressed, and the A2pot constructs are expressed.

FIGS. 2A-2D provide sequences for an A2pot cassette, lacIn repressor, and merA77. FIG. 2A shows the A2pot expression cassette, which includes elements from the constitutive actin ACT2 gene. See SEQ ID NO:12. The ACT2 promoter region was modified to contain two 25 nucleotide bacterial lac operator sequences (lac0) (lower case, underlined regions) replacing 25 nt of native ACT2 sequence. The first operator is located immediately after the TATA box sequence (TATATAA in bold) specifying transcriptional start sites approximately 37 bp down stream and the second operator following the first start of transcription within the 5' UTR. In addition to the MCS (multiple cloning site), there is also included the ACT2t transcription termination sequence. FIGS. 2B and 2C show the coding and amino acid sequences of the LacIn repressor coding and protein, respectively. See also SEQ ID NO:10 and SEQ ID NO:11. The lacIn coding sequence was generated by adding codons for a C-terminal nuclear localization signal NLS (underlined sequences) to the wildtype bacterial lacI coding sequence. FIG. 2D shows how the modified bacterial mercuric ion reductase gene sequence merA77 was constructed to have a more plant-like GC composition and lower CpG dinucleotide frequency. The portions of the merA77 sequence that have been made synthetically, and the translational start and stop codons are underlined. See also SEQ ID NO:13.

FIGS. 3A-3K show the constitutive and root-specific expression of beta-glucuronidase from the A2pot::GUS sequence in transgenic *Arabidopsis* with and without lacI repressor expression. Control (wild type) seedlings (FIGS. 3A-3C), seedlings transformed with the A2pot::GUS gene (FIGS. 3D-3G) or seedlings cotransformed with both the A2pot::GUS and the S1pt::lacIn genes (FIGS. 3H-3K) were examined for GUS enzyme expression. Transgenic seedlings were stained for 8 hours in GLUC at room temperature, washed in 70% ethanol, and photographed in bright field.

FIG. 4A is a photograph of Western blots showing LacIn protein expression cells from transgenic plants expressing the SRS1pt:lacIn in leaves but not roots. 15 μg total protein was isolated from transgenic *Arabidopsis* leaf and root tissues and size-separated by SDS-PAGE (12% gel). The separated proteins were electroblotted onto immobilon-P nylon transfer membranes (Millipore). The membranes were incubated in blocking solution for one hour, and primary antibody (anti-LacI polyclonal antibody, Stratagene, Inc, La Jolla, Calif.) was added with incubation for one additional hour. The blots were washed with TBSt buffer and then incubated with anti-rabbit IgG conjugated with horseradish peroxidase (Amersham, Inc.). The blots were then washed 3 times with TBSt buffer, and the proteins were visualized using the ECL system (Amersham, Inc.). FIG. 4B illustrates the subcellular localization of LacIn in leaf cells of plants expressing S1pt::LacIn. The LacIn protein was localized using FITC-goat anti-rabbit antiserum (Sigma, St. Louis, Mo.). No signal was detected in wild type or transgenic root tissue.

DETAILED DESCRIPTION OF THE INVENTION

Figure 1A:
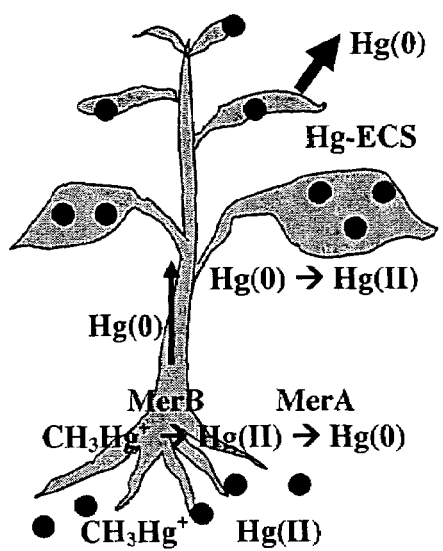
FIGS. 1A-1B provide strategies and constructs for engineering the hyperaccumulation of mercury above ground, which depend upon the root-specific expression of mercuric ion reductase.

Phytoremediation is the use of plants to clean toxic pollutants from soil, water, and/or air. Strategies for the phytoremediation of mercury are outlined in FIGS. 1A-1B. These strategies include transgenic plants managing mercury by controlling the transport, chemical species, electrochemical state, and aboveground sequestration of mercury. We now have three very significant findings. First, plants constitutively expressing the bacterial merB organomercury lyase gene in *Arabidopsis* efficiently convert methylmercury (MeHg) to ionic mercury (Hg(II)), which is much less toxic, and unlike MeHg, Hg(II) is not biomagnified in the food chain (Heaton et al., 1998; Bizily et al., 1999; Bizily et al., 2000). Plants can accumulate low µM levels of the Hg(II) product in tissues with no measurable negative effect on growth. Second, a variety of plant species constitutively expressing the bacterial merA mercuric ion reductase gene convert Hg(II) to volatile and less toxic Hg(0) (Rugh et al., 1996; Heaton et al., 1998; Rugh et al., 1998a). These plants accumulate very little mercury in their tissues as compared to wild-type because the elemental mercury appears to be transpired from the plants. Plants expressing merB and plants expressing merA are highly resistant to organic and ionic mercury, respectively, while wildtype plants are highly sensitive to both compounds. Plants expressing both merB and merA can efficiently couple the two reactions and volatilize Hg(0) when given organic mercury substrates (Bizily, 2001; Bizily et al., 2003). Third, compared to wild type, plants expressing bacterial ECS γ-glutamylcysteine synthetase gene make more cysteine sulfur-rich peptides that can sequester Hg(II) and are moderately resistant to ionic mercury. See also U.S. Pat. Nos. 5,668,294 and 5,965,796 and International Patent Publication WO 02/048335.

It is essential to develop additional strategies for the aboveground accumulation of mercury. One is based on combining the reduction of Hg(II) in roots with Hg(0) oxidation in leaves and stems. Critical to this strategy is whether or not the engineered root-specific expression of merA (FIG. 1) increases the transport of metallic elemental mercury (Hg(0)) to aboveground tissue. Support for this idea comes from a grafting experiment between engineered and wildtype (WT) tobacco. When WT tobacco stems and leaves are grafted onto transgenic merA tobacco roots the aboveground parts of these plants accumulate more mercury than plants expressing the MerA protein in roots, leaves, and stems or than wildtype plants (Heaton et al., 1998). Hg(II) entering roots is converted to Hg(0) by MerA and transported aboveground as the soluble gas Hg(0) in the transpiration stream. Furthermore, without MerA activity in stems and leaves, Hg(0) is oxidized back to reactive Hg(II) and trapped. Bacterial peroxidases and catalases are known to reoxidize Hg(0) to Hg(II) (Ogata and Aikoh, 1984; Smith et al., 1998). Similar endogenous activities can oxidize Hg(0) to Hg(II) in higher animals and plants (Waldron and Terry, 1975; Halbach et al., 1988). Hg(0) volatilization demonstrated for merA transgenic *Arabidopsis*, cottonwood, and yellow poplar (Meagher and Rugh, 1996; Heaton et al., 1998; Rugh et al., 1998a; Rugh et al., 1998b); was dependent upon the continued reduction of Hg(II) to Hg(0) by the MerA enzyme in leaves. Without wishing to be bound by theory, we believe that without continued electrochemical reduction, mercury is oxidized and trapped aboveground by these plants.

Figure 1B:
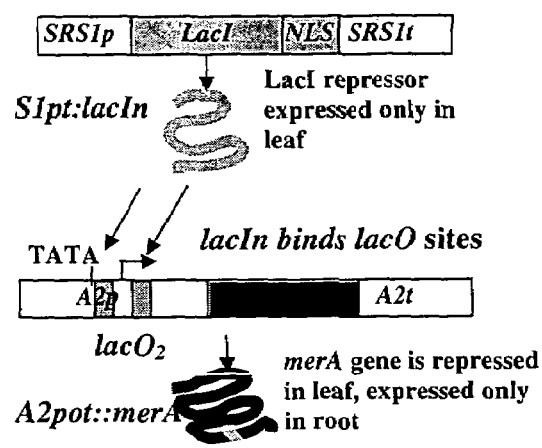

We have developed a strong constitutive root-specific expression system by combining elements from the bacterial lac operon (e.g., repressor (I), operator (O)) with two strong plant expression cassettes as outlined in FIG. 1B. A modified LacI repressor protein containing a nuclear localization signal (NLS; see SEQ ID NO:9), termed LacIn herein (see SEQ ID NO:11), was expressed from a light-regulated, leaf-specific promoter. In addition, the strong constitutive promoter was modified to contain two lacO sequences. Therefore, the LacI repressor functions in leaves to shut down the lacO-modified promoter, but this promoter is fully active in roots. When the expression of these two elements are combined, strong root-specific expression was observed for two representative target gene sequences, β-glucuronidase (GUS) and merA.

The *Arabidopsis* ACT2 actin promoter drives strong constitutive target gene expression in all vegetative plant organs, tissues, and cell types in young and mature plants (An et al., 1996; Kandasamy et al., 2002). The Act2pt promoter terminator cassette was modified into a LacI-repressible expression cassette, A2pot, via the addition of two 25 bp lacO operator sequences from the *Escherichia coli* lactose operon as shown in FIG. 1B. These sequences were inserted after the ACT2 TATA box sequence, replacing two 25 bp stretches of native sequence before and after the start site for transcription constructing the new vector A2pot sequence presented in FIG. 2A. Because the two 25 bp substituted regions of ACT2 native promoter are poorly conserved with the closely related ACT8 actin promoter sequence, it was believed that these sequences are not essential to strong constitutive expression (An et al., 1996). The GUS reporter sequence was cloned as a perfect translational fusion with the ACT2 AUG initiation codon into A2pot. The resulting A2pot::GUS gene was transferred into a plant binary vector, and transformed into *Arabidopsis* via vacuum infiltration, and then GUS reporter expression was examined in $T_2$ generation transgenic seedlings and plants as shown in FIGS. 3A-3K. The leaves and roots from several $T_2$ generation transgenic plants (FIGS. 3D-3G) were assayed for the indigo blue product of β-glucuronidase (produced by the GUS chimeric gene) and its chromogenic substrate. A2pot::GUS was expressed in all vegetative tissues and cells in transgenic *Arabidopsis*. All vegetative organs and tissues and cells of the transgenic plants turned blue even after short 2 hour staining times, demonstrating the strength of GUS expression. Hence, it does not appear that insertion of the lacO sequences significantly alters the strong vegetative constitutive expression pattern of the A2pt promoter from those of the wild type ACT2 promoter (An et al., 1996).

Figure 4A:
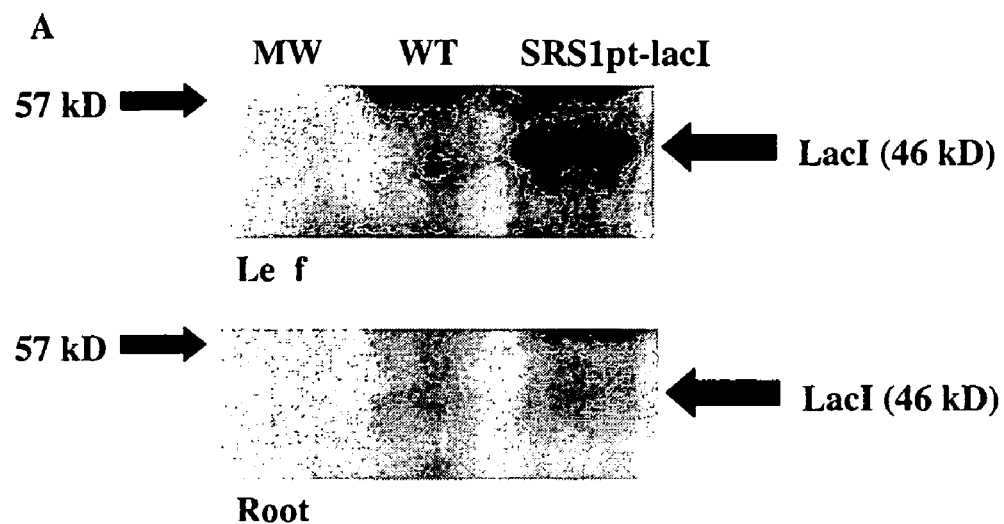
FIGS. 4A-4B show expression of the LacIn protein.
Figure 4B:
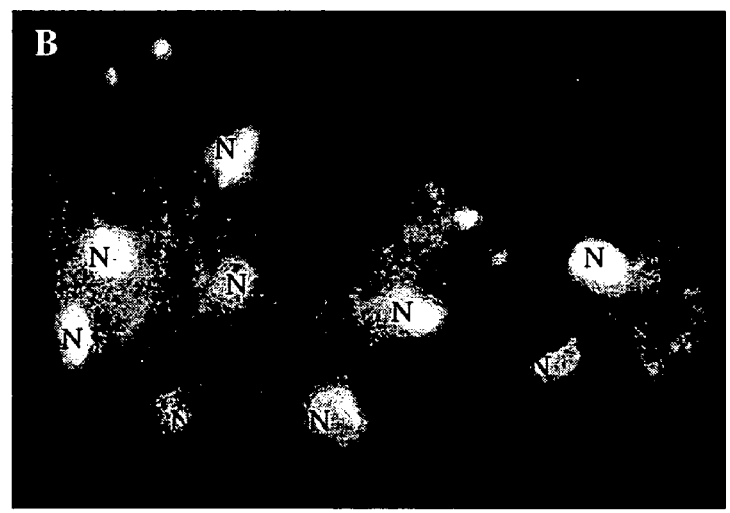

The S1pt::LacI repressor vector was constructed as follows. An expression cassette (S1pt) from the soybean ribulose bisphosphate carboxylase (RUBISCO) small subunit gene SRS1 was chosen to drive expression of a modified bacterial lac operon repressor, LacIn, in leaves. The lacIn DNA sequence (FIG. 2B) was modified from the wild type bacterial LacI sequence to encode a protein with the C-terminal artificial eukaryotic nuclear localization signal, SSVVHP-KKKRKV (SEQ ID NO:9), as shown in the LacIn protein sequence (FIG. 2C, SEQ ID NO:11). LacIn was cloned as a perfect translational fusion into the S1pt promoter terminator vector to make S1pt::LacIn (FIG. 1). Transgenic plants expressing the S1pt::LacIn sequence produced LacIn protein in aboveground tissues, as shown on Western blots in FIG. 4A. No LacIn protein was detected in roots. LacIn was concentrated in the nuclei of leaf cells (FIG. 4B), demonstrating the efficiency of this artificial NLS.

An A2pot root-specific expression system with a GUS reporter was tested. When the A2pot::GUS gene is co-transformed with S1pt:LacI approximately 40% of the transgenic plants survived selection for both linked drug markers, kanamycin and hygromycin. More than 50% of the $T_2$ generation plants showed little or no GUS expression in the first two leaves (FIGS. 3H and 3I), while root expression remained quite strong in these plants (FIGS. 3J and 3K). Strong staining was observed in all tissues and cells of the primary and lateral roots and root staining was indistinguishable from that in plants lacking the repressor (compare FIGS. 3G and 3K). Some staining was observed in cotyledons at the distal leaf margins. Non-transgenic control plants showed no GUS staining (FIGS. 3A-3C).

Figure 5:
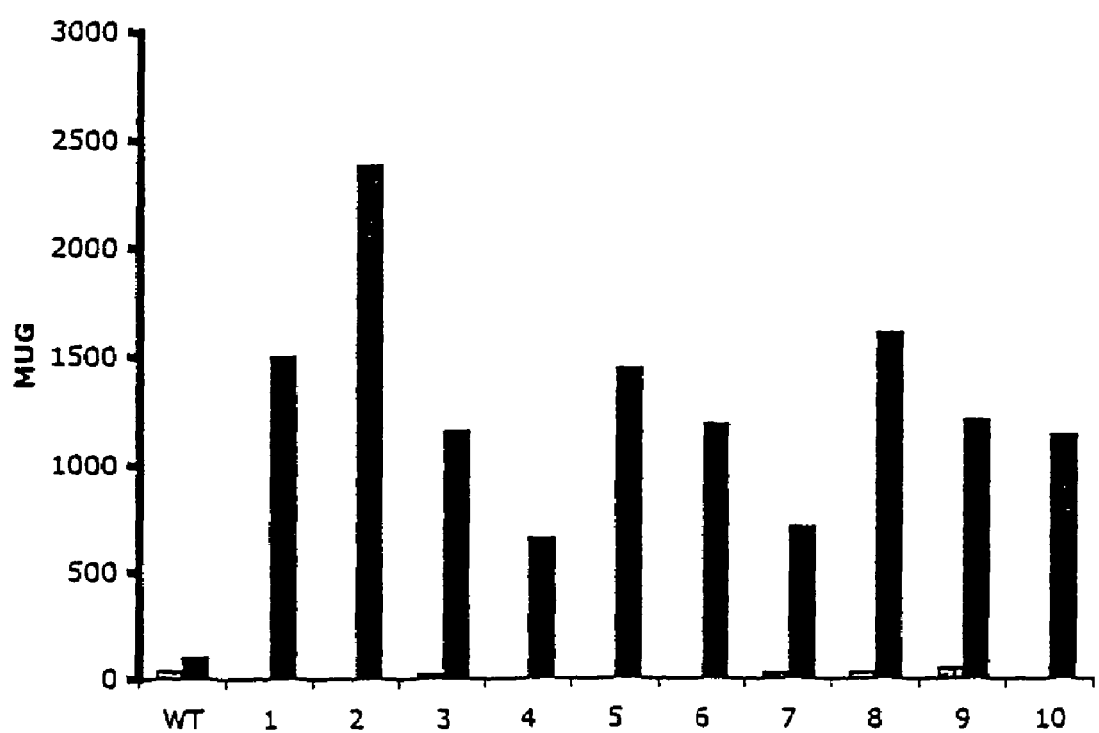
FIG. 5 shows quantification of GUS expression in individual transgenic plants expressing both A2pot::GUS and the S1pt::lacIn. Wild type plants and 10 individual $T_2$ generation plants were stained with MUG substrate, excited at 490 nm and fluorescence measured at 520 nm. The relative GUS activity is given in arbitrary fluorescent units for the average background (91 units) in control leaf and root samples.
Figure 6:
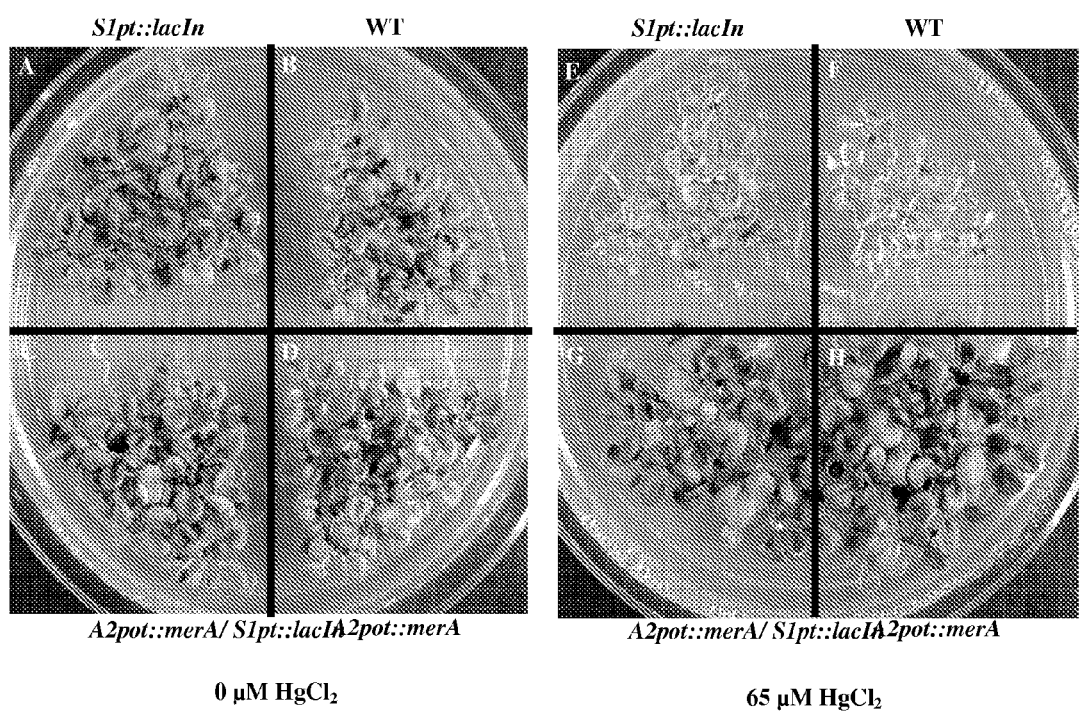
FIG. 6 illustrates the mercury tolerance of plants with root-specific MerA expression. The tolerance of plants coexpressing the A2pot::merA and S1::lacIn genes was compared to plants expressing either construct alone and wild type plants. Transgenic seeds of *Arabidopsis* containing S1pt::lacIn (Panel A), seeds of wild-type (WT, Panel B), transgenic seed containing A2pot::merA (Panel C) and transgenic seeds containing S1pt::lacIA2pot::merA (Panel D) were germinated on half-strength MS media containing no $HgCl_2$ and grown for 2 weeks. Transgenic seeds of *Arabidopsis* containing S1pt::lacIn (Panel E), seeds of wild-type (WT, Panel F), transgenic seed containing A2pot::merA (Panel G) and transgenic seeds containing S1pt::lacIA2pot::merA (Panel H) were germinated on half-strength MS media containing 65 µM $HgCl_2$ and grown for 2 weeks.
Figure 7:
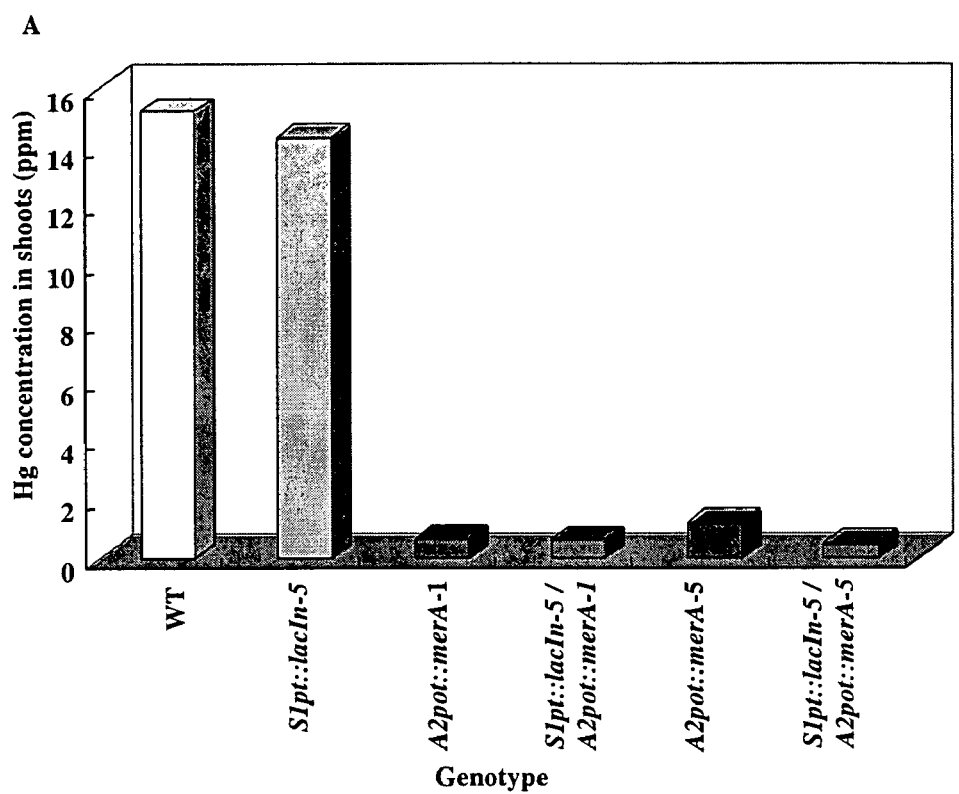
FIG. 7 summarizes quantification of above-ground mercury concentration. Above-ground mercury accumulation in plants coexpressing the A2pot::merA and S1::lacIn genes was compared to plants expressing either construct alone and wild type. Seeds were germinated on agar medium containing 20 µM Hg(II) and seedlings were grown on platforms in liquid media for 3 weeks. Shoots were harvested, washed 3 to 4 times with deionized water, and frozen in liquid nitrogen. The plant samples were lyophilized at −70° C. for 72 h, digested in a mixture of nitric and perchloric acids (7:1 v/v) using standard methods, and were analyzed for mercury content using Inductively Coupled Plasma-Mass Spectrometry (ICP-MS) (Suszcynsky and Shann, 1995).

The ratios of GUS expression in roots and leaves were quantified in several T2 generation A2pot::GUS+S1pt:LacIn plants grown as shown in FIGS. 3A-3K using the fluorescent MUG assay (FIG. 5). GUS expression in these LacIn-repressed plants was 20 to 200 fold higher in roots than in leaves. Leaf expression was so low as to be indistinguishable from that in WT non-transformed plants. However, these doubly transformed plants have only slightly diminished root GUS expression as compared to plants expressing. Using purified GUS protein as a standard for absolute levels, GUS appears to be highly expressed.

Root-specific expression of merA in transgenic plants was achieved. A modified version of the bacterial merA gene, merA77, was cloned into the repressible actin expression vector to make A2pot::merA (FIG. 2D). The merA77 sequence encodes a wild type MerA protein, but has a lower GC composition and fewer CpG dinucleotides than the wild type merA gene sequence. Approximately 77% of the merA77 coding sequence has codon usage modified from the wild type sequence. See U.S. Pat. No. 5,668,294 for further information on merA sequences adapted for efficient plant expression. The leaves and roots of plants expressing A2pot::merA show high levels of MerA protein on Western blots using a monoclonal antibody specific to MerA, shown in FIG. 5. In contrast, MerA protein was undetectable on Western blots examining leaf proteins of most plants (60%) cotransformed with both A2pot::merA and with S1p::LacIn. The plants with low levels of MerA expression in leaves correspond with those having high levels of LacI protein. These doubly transformed plants all show high levels of root specific MerA expression. Using purified MerA protein as a standard, the level of root MerA protein in plants showing leaf repression is approximately 0.2% of total root protein. Hence, the S1p::LacIn construct expresses insufficient LacIn repressor to cause significant repression.

The T2 generation seeds of doubly transformed plants expressing MerA protein exclusively in roots are plated on media with 50 and 75 μM Hg(II). These plants expressing root-specific MerA were as resistant to Hg(II) as were plants expressing MerA from the A2pot::merA construct alone without LacIn repression. As expected from previous studies, wild type seeds and seedlings die on these same Hg(II) concentrations. Thus, detoxification of Hg(II) to Hg(0) in roots is sufficient to confer resistance to above ground portions of the plant.

Hydroponic growth experiments are conducted to determine mercury accumulation levels in plant organs of wild-type and genetically modified plants. Plants are suspended on a platform in the growth medium and exposed to lower, sublethal mercury concentrations (20 μM Hg(II)). After 24 hours, roots and leaves are harvested and analyzed for mercury content by ICP-MS. Doubly transformed plants expressing MerA protein exclusively in roots accumulate more mercury in stems and leaves than plants expressing MerA in all organs and more mercury than wild type plants as shown.

Our results show that expression of the LacIn repressor from S1pt::LacIn results in strong constitutive root-specific expression of transgenes expressed from the A2pot cassette. Evidently insertion of two lac operator sequences flanking the TATA box in A2pot did not greatly reduce the strong expression from the ACT2 promoter. This is in contrast to similar insertions into in some mammalian expression vectors, which resulted in inefficient transgene expression even in the absence of added bacterial LacI repressor (Hu and Davidson, 1990). This confirms previous suggestions that the two 25 bp substituted sequences in the ACT2 actin promoter, one immediately after the TATA box and one immediately after the start of transcription, were not evolutionarily conserved even over a short 50 million time scale and hence were not important to ACT2 promoter activity (An et al., 1996).

A key to many engineered phytoremediation strategies is plant and plant tissue resistance to the toxin being remediated. To effectively remediate Hg(II), sufficient root expression of MerA must occur in all root tissues to convert the majority of Hg(II) to Hg(0) in order to protect the plant from ionic mercury's toxic effects. In other words, the levels of MerA protein need to be high enough to withstand a large amount of incoming Hg(II) at highly contaminated environments. The root-specific expression strategy outlined herein results in sufficient Hg(II) resistance, a critical aspect of any mercury phytoremediation strategy.

An additional benefit of MerA root expression is the mobilization of Hg(0) to above-ground tissues and organs, where it can be reoxidized and trapped. Mobilization of mercury to above ground tissues must be coupled to increasing sinks than bind mercury for a true hyperaccumulator to be engineered. Initial efforts to make sinks for Hg(II) in leaves were moderately successful. We found that a 10 fold enhancement in the levels of the dipeptide gamma-glutamylcysteine (EC), which binds reactive Hg(II), did provide some level of resistance.

Several root-specific genes have been reported previously, which might have been chosen as a source of natural promoter and terminator sequences to drive MerA expression, however, few of their promoters could have driven the expression of MerA in all root tissues and cells. For example, the *Zea maize* zmGRP3, ZRP2, and ZRP4 genes (Held et al., 1993; Held et al., 1997; Goddemeier et al., 1998) and tomato LeRse-1 gene (Lauter, 1996) all showed weak to moderate levels of root-specific expression. Localization of ZRP2 and ZRP4 mRNAs suggest their expression is concentrated in cortical parenchyma cells of young roots and the root endodermis, respectively. A few plant promoters driving root-specific expression of reporters in transgenic plants have been described, such as *Arabidopsis* SCARECROW (Sabatini et al., 2003), tobacco TobRD2 (also NtQPT1) (Conkling et al., 1990), and TobRB7 (Yamamoto et al., 1991). Reporter expression patterns from these promoters are restricted to subsets of tissues including the root meristematic region, root cortex, and root vascular cylindar, respectively. Finally, promoter constructs derived from the *Arabidopsis* Pyk10 gene drive weak to moderate levels of constitutive root-specific reporter expression in a large percentage of transgenic plants (Nitz et al., 2001). The expression of one Pyk10 reporter construct was quantified to be only about 7-fold higher in roots than in shoots. Both Pyk10 constructs that had their expression levels quantified showed significant shoot expression. This would be disadvantageous to the mercury remediation strategy being explored, because shoot expression of merA would result in Hg(0) volatilization. We previously tested merA expression in transgenic tobacco driven from two of these promoters, NPQpT1 (TobRD2) (Conkling et al., 1990; Yamamoto et al., 1990) and RB7 (Yamamoto et al., 1991) using designs similar to our earliest 35Sp::merA constructs that were quite strongly expressed (Rugh et al., 1996). The RD2p::merA and RB7p::merA constructs were examined separately in transgenic plants and transgenic plants that expressed both. Plants expressing the individual constructs and both constructs these together were weakly mercury-resistant. However, neither promoter-merA fusion alone nor the two combined generated strongly mercury-resistant tobacco. MerA protein levels in roots from both constructs were weakly detectable by Western blots as compared to the strong MerA expression demonstrated herein. The RB7::merA plants showed almost as much expression in leaves as in roots. These disappointing results led to the development of the LacIn-repressed actin promoter (A2Ppot) vector system described herein.

The promoter from the soybean SRS1 RUBISCO gene has been characterized in detail; it is known to drive strong, white light-dependent, transcription and transgene expression in the leaves and stems of transgenic plants (Shirley et al., 1987; Shirley, 1989). More recently, SRS1 derived cassette vectors have been shown to drive strong leaf-specific expression of arsenic reductase, β-glucuronidase (GUS), and γ-glutamylcysteine synthetase (Dhankher et al., 2002). In contrast, none of these three protein products were detected in transgenic roots in sensitive Western blot assays. In particular, one S1pt:: GUS reporter construct strongly expresses GUS in all leaf tissues of transgenic plants. Again, lack of repressor expression in roots was essential to the mercury hyperaccumulation strategy described in FIG. 1A, because small amounts of repressor expression in root nuclei lower root MerA activity and weaken electrochemical reduction of Hg(II). Expressing repressor from the S1pt vector has limitations. For example, using this expression system in transgenic shrubs and trees might result in no repressor being made in any non-photosynthetic tissues, and this would result in target gene expression (i.e., MerA) expression in stem tissues.

The LacIn protein was primarily localized to the nucleus and clearly worked as an effective repressor of the A2pot expression constructs in leaves, where it was expressed. However, some LacIn was detected in the cytoplasm, generating the background of fluorescence shown in FIG. 4B. It is possible that nuclear localization signals other than the NLS sequence SSVVHPKKKRKV (SEQ ID NO:9) used herein could be fused to LacI and improve nuclear targeting. Alternatively, and without wishing to be bound by theory, it is believed that when a nuclear-targeted protein is expressed at the high levels that occur from the S1 cassette, other nuclear transport machinery limits nuclear transport of LacIn protein.

The lac system is one of the best-characterized inducible regulatory systems. Lac operon-based inducible gene expression has been successfully transferred into mammalian and plant systems previously (Fuerst et al., 1989; Ulmasov et al., 1997). This property of inducibility has been used in several commercially available mammalian expression vectors such as LacSwitch from Stratagene, La Jolla, Calif. The inducibility of lac-based expression systems is based on the fact that the homo-tetrameric LacI repressor undergoes a conformational shift in the presence of an inducer like lactose or IPTG and is released from the operator sequence. Constitutively expressed lacIn constructs are designed to repress the constitutive A2pot cassette in all tissues. This results in a plant system where expression is normally off but can be turned on by plant exposure to lactose or ITPG. Considering the initial strength of A2pot-driven expression of the GUS and merA77 genes and the tight repression in leaves, the inducibility of this promoter is useful in basic research. For example, in *Arabidopsis* the constitutive expression of RNA interference (RNAi) constructs targeting suppression of essential genes requires that these genes be expressed at levels necessary for plant survival and recovery of viable $T_1$ generation seeds. In contrast, an inducible suppression system results in the recovery of plants with more deleterious phenotypes or even allow the demonstration of lethality, because the RNAi transgene can be turned on at any time in plant development.

None of the published and commercially available lac operon-based regulatory systems have been designed for permanent repression of target genes in a subset of organs and tissues; i.e., there have been no tissue-specific expression systems combining the bacterial lac operon control sequences with a strong constitutive promoter from a plant where application of a chemical inducer is not required. The root-specific gene expression strategy described herein does not require inducibility, but only permanent repression in green tissue. For inducible expression in eukaryotic systems, it is essential the Lac repressor protein concentrate in the nucleus and have only a moderate affinity for operator sequences so that repressor is released after interacting with inducer and undergoing an conformational shift. The affinity of wild type bacterial Lac repressor for operator is about $K_d = 10^{-12}$ mole/liter (Betz et al., 1986; Whitson et al., 1986). Tighter binding and more efficient repression in the leaf is useful in this plant root-specific expression system, because it results in lower expression levels of the LacIn repressor being required. Mutant LacI repressors with 10,000-fold higher affinities for operator sequences and mutant operators with 30-fold higher affinities for repressor have been reported (Pfahl, 1979; Betz et al., 1986; Falcon and Matthews, 2000), and these mutant repressors can be modified with a nuclear translocation signal and incorporated into the regulated expression strategy described herein. Other mutated but functional (operator binding) Lac repressor protein sequences are known to the art. Similarly, there are other (mutated) functional (repressor binding) lacO sequences known to the art which can be substituted in place of the operator sequence specifically disclosed herein.

A strong constitutive, root-specific promoter is essential in many areas of plant biotechnology including phytoremediation, control of plant root diseases, plant nutrition, and food safety. Phytoremediation strategies for detoxification of organic pollutants and transformation of toxic elements to less toxic forms such as the electrochemical reduction of niter-aromatics or protonolysis of methylmercury require the intense interaction of roots with soil-born toxicants. Such approaches use plant roots as both energy conduits and enzyme sources to condition soil (Meagher, 2000; Meagher and Fechheimer, 2002). The enhanced uptake of essential nutrients such as iron, zinc, potassium, and/or nitrate into plant roots enhances plant yield and nutritional quality (Guerinot and Eide, 1999; Guerinot, 2001). Numerous fungal pathogens, such as *Fusarium solani* f. sp. *glycines*, which causes sudden death syndrome in soybean (Iqbal et al., 2002), *Gaeumannomyces graminis* var. *tritici*, which causes take-all disease in wheat (Gutteridge et al., 2003), and various *Fusarium* and *Verticillium* species, which cause wilt diseases in vegetable crops (Anjaiah et al., 2003; Lievens et al., 2003) target roots. Nematodes nearly all target roots, and several diseases such as soybean cyst nematode (Lewers et al., 2002) and nematode root-knot (Giblin-Davis et al., 2003) cause significant annual loss of crops. Targeting the synthesis of fungal-specific and nematode-specific toxins or degradative enzymes such as chitinase with the root-specific expression system described herein improves the yield and quality for many food, forage, and animal feed crops (Gao et al., 2000). Proteins and functional RNAs which confer resistance to fungal, bacterial and viral pathogens are also known, and can be similarly expressed using the transcription regulatory system of the present invention to protect plants from the corresponding pathogens. Root-specific protection from pathogens would improve crop and food safety by restricting expression of anti-fungal and anti-nematode agents to roots and preventing the synthesis of native toxins by these pathogens. The economics of production are also improved where loss is less and there is reduced need for the application of pesticides.

Figure 8:
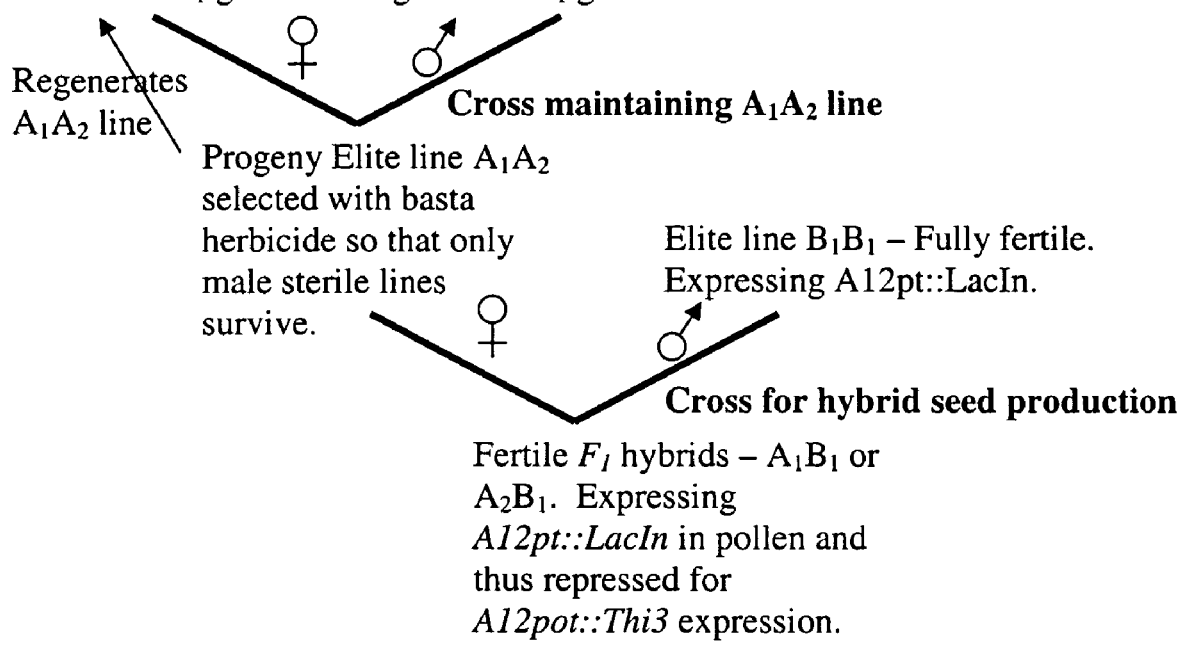
FIG. 8 illustrates the genetic crosses used in male-sterility repressor operator complex system for the hybrid seed industry. This repressor-operator gene complex (ROC) is used to conditionally target pollen for ablation by expression of a sterilizing transgene (deleterious gene) in the $A_1$ genome unless the sterilizing transgene is repressed by a gene in the $B_1$ genome. Genetic crosses between various lines used to create and maintain a plant male-sterility system are shown. When the two elite lines, $A_1A_2$ and $B_1B_1$, are crossed the resulting hybrids, $A_1B_1$ and $A_2B_1$, are fully-fertile (bottom). The male-sterile $A_1A_2$ elite line is maintained by crosses with the $A_2A_2$ elite inbred plant line followed by spraying with the herbicide basta.

Referring to the embodiment of the present invention in which the tissue-specific gene expression is for reproductive (anther) tissue and a method for relevant hybrid seed production, there is an elite line $A_1A_2$, a female, male sterile parent by way of an $A_{12}$pot::Thi3Ri (or A12pot::Thi2Ri) gene (or a similarly regulated high affinity thiamine binding protein) and a basta marker also incorporated within the genome, crossed with an elite line $A_2A_2$ maintainer line, which is a fully fertile parent lacking the Ri (or other deleterious gene) and basta genes on the $A_1$ genome. From this cross, only the $A_1A_2$ male sterile lines survive basta selection. These progeny are then crossed with fully fertile $B_1B_1$ line which expressed A12pot::lacIn. Fully fertile F1 hybrids are produced, which are either $A_1B_1$ or $A_2B_1$. These fertile hybrids express A12pot::lacIn in pollen and are thus repressed for A12pot::Thi3Ri (or A12pot::Thi2Ri) expression. See FIG. 8 or a summary of the plant crossing strategy and FIG. 9 for a schematic of the gene expression strategy. It is understood that where there would be male sterility due to the interference RNA which disrupts expression of the Thi3 or Thi2 thiamine biosynthetic gene, the male sterility can be avoided by spraying the flowers with a thiamine-containing solution or by otherwise supplementing the growth medium or irrigation water with thiamine in an amount sufficient for overcoming the nutritional thiamine deficiency. As an alternative to the expression of the Thi3 or Thi2 interfering RNA expression, there can be expression of an enzymatically inactive, high affinity thiamine binding protein coding sequence under the control of a lacO-containing promoter which specifically directs expression in plant reproductive tissue.

As used herein, a male sterile plant is a plant which does not produce functional pollen, and hence, there is no outcrossing. Seed sterility is where viable seeds are not produced to embryo lethality. Female sterility refers to the inability of the female germ line of a plant (ovule and endosperm) to develop, receive pollen or develop once fertilized, and there is no introgression or selfing. Where there is female sterility, pollen from a native plant cannot fertilize the engineered female sterile plant and no fertile offspring are produced. When male and female sterility are present, there is no outcrossing, no introgression and no selfing.

Systems of plant sterility are important tools in the hybrid seed industry, forestry, and phytoremediation. The hybrid seed industry, for example, plants millions of acres in which one of the two elite parent plants in a genetic cross is male sterile as a result of physical or genetic emasculation. In phytoremediation, genetically engineered plants are being developed that extract, detoxify, and/or sequester toxic pollutants, and their germplasm needs to be tightly controlled. In this case, systems of male and female sterility are needed if plants are to be released permanently into the environment. Control of fertility also limits unauthorized propagation of proprietary material. An especially useful sterility system is one in which sterility is conditional, and in which elite parental lines can still be propagated through fully fertile crosses. The present invention provides a specifically exemplified conditional sterility system based on suppression of the pathway for thiamine B1 synthesis, sequestration of thiamine or destruction of thiamine B1 during pollen and/or ovule development such that the plants exhibit thiamine-deficiency based conditional sterility (TDCS). Fertility of the TDCS plants is restored by treatment with excess thiamine, a harmless vitamin. In addition, plant sterility can improve the economics of wood and pulpwood production because phosphorus and nitrogen are not "wasted" in the production of pollen and seed. This is particularly applicable to pine and eucalyptus. Controlled sterility is also applicable to genetically modified turfgrass or bentgrass; to the production of seedless fruit such as watermelon or grapes. These methods can also be applied to the animal forage crops; many forage crops such as alfalfa, fescue and Bermuda grass decline in feed quality when they go to seed. Similarly, the sugar yield from sugar cane is improved if the cane does not go to seed as a result of genetic modification to contain and express a conditional sterility construct of the present invention. A particularly important advantage of the sterility embodiment of the present invention is that it is not labor-intensive.

Systems of plant sterility are essential tools in the hybrid seed industry, forestry, conservation biology, and phytoremediation. The hybrid seed industry plants millions of acres of in which one of the two elite parent plants in a genetic cross is male sterile as a result of physical or genetic emasculation. Male sterility is the basis for this 400 million dollar per year industry. Foresters are interested in plant sterility, because wood production is dramatically reduced when nitrogen and phosphorus are drained into pollen and megagametophyte production. In addition, genetically engineered trees, shrubs, and grasses are being developed that extract, detoxify, and/or sequester toxic pollutants and for phytomining of precious elements. Conditional male sterility adds value to and limits unauthorized propagation of valuable plants for any purpose. Plant sterility systems are needed if genetically modified organisms (GMOs) are to be released into the natural environment with no release of their germplasm. In this case, complete male-female sterility is desirable so that the organisms cannot reproduce seed by any means.

TDCS can be achieved by altering the expression of three different genes in the model plant *Arabidopsis*. Two genes, AtThi2 and AtThi3, encoding a bifunctional enzyme (phosphomethylpyrimidine kinase, thiamine phosphate pyrophosphorylase also called thiamine synthase) and a monofunctional enzyme (hydroxyethylthiazole kinase) in the thiamine B1 synthesis pathway, respectively, are targeted for suppression in *Arabidopsis* reproductive tissue. RNA interference (RNAi) is used to degrade target AtThi2 and AtThi3 RNAs using the tissue-specific lacO promoter construct and the regulated lacI expression system of the present invention. In addition, TDCS can be achieved by sequestering thiamine in reproductive tissues by the overexpressing a mutant form of *Arabidopsis* pyruvate decarboxylase (PDC). The resulting plants with one or more of these transgenes are sterile under normal soil growth conditions, but fully fertile when supplemented with excess thiamine B1.

Thiamine (Vitamin B1) is an essential vitamin in mammals. Plants make their own thiamine, because it is an essential cofactor in metabolism. For example, pyruvate decarboxylase, xylulose transketolase, and acetolactate synthase (Chang and Duggleby, 1997), and other enzymes that convert carboxyl groups to aldehydes or ketones, require thiamine B1 (Bouvier et al., 1998). Thiamine biosynthesis can be ablated or thiamine can be sequestered in reproductive organs and tissues to create conditional auxotrophic sterile mutants ("knockdown lines") that require thiamine for fertility.

Figure 9:
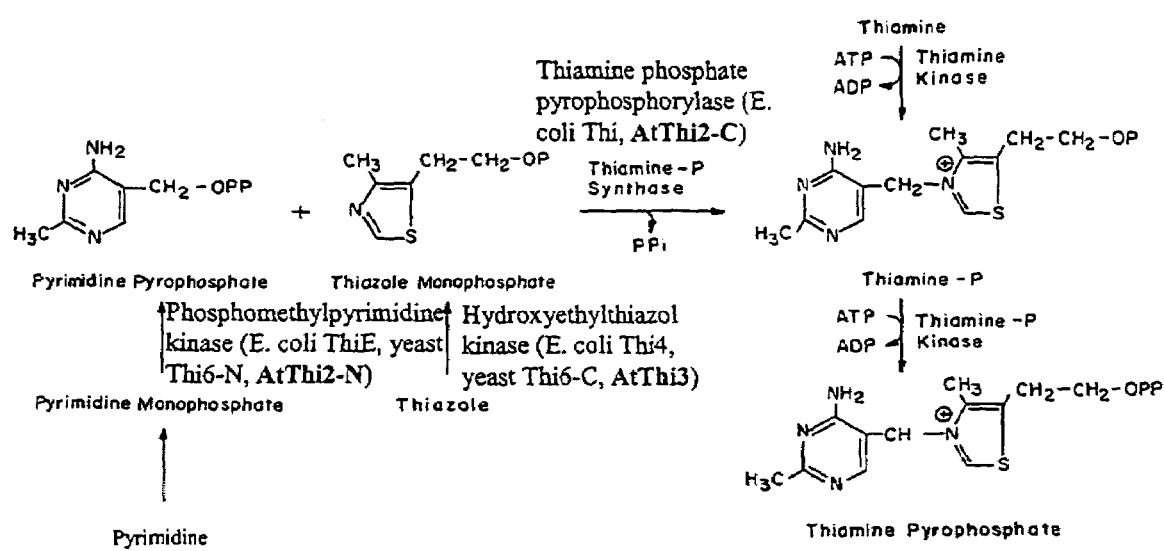
FIG. 9 summarizes the strategy for ROC-mediated conditional thiamine deficiency based male sterility in a plant.

*Arabidopsis* thiamine (B1) auxotrophic mutants grow well with exogenously added B1 in their growth medium (Li and Redei, 1969; Redei and Li, 1969; Ledoux et al., 1974). Plants appear to use a thiamine (B1) biosynthesis pathway similar to that described in bacteria and yeast, the final steps of which are shown in FIG. 9 (see also Brown and Williamson, 1987). Pyrimidine pyrophosphate and thiazole monophosphate are combined by the action of thiamine phosphate synthase to make thiamine phosphate. The pyrimidine and thiazole derived components are both made by poorly characterized biochemical pathways (Brown and Williamson, 1987). In the last decade several genes encoding enzymes or regulatory proteins in the thiamine pathway have been characterized in *Escherichia coli, Saccharomyces cerevisiae* and *Schizosaccharomyces pombe*.

We have identified genes involved in thiamine B1 synthesis in the *Arabidopsis* database. Using yeast, *S. pombe*, and *E. coli* query sequences, we found several genes encoding homologues to B1 synthesis enzymes. No attempt was made to identify DNA regulatory proteins involved in thiamine synthesis. Examples of the relevant *Arabidopsis* sequences identified with potential roles in thiamine synthesis or binding are listed in Table 1. This analysis reveals several gene sequence targets in the *Arabidopsis* genome that are believed essential for thiamine B1 biosynthesis, modification, and degradation. Many of them are single-copy or low-copy genes, which simplifies any strategy for blocking thiamine synthesis or sequestering available thiamine in plant cells.

Only one *Arabidopsis* gene (AtThi1) implicated in thiamine B1 synthesis (AtThi1) has been partially characterized for function (Machado et al., 1996; Machado et al., 1997; Chabregas et al., 2001). This gene complements *E. coli* mutations that affect DNA repair, such as uvrA. AtThi1 is also a sequence homologue of the B1 biosynthetic genes of yeast Thi4 and *S. pombe* Thi2. AtThi1 complements yeast mutants in the essential Thi4 gene, and it appears to complement both yeast cell viability and DNA repair activity as measured for mitochondrial DNA. Using either *S. pombe* Thi2 or yeast Thi4 protein as the query sequence, we detected a single *Arabidopsis* Thi1 sequence (NP200288). It has very strong homology over most of its length and 65% identity to the *S. pombe* Thi2 (Nmt2) protein (Table I, AtThi1). Thus, AtThi1 appears to be a single copy gene. AtThi1 is synthesized in the cytoplasm and then transported into to both the chloroplast and mitochondria by means of a dual N-terminal peptide targeting sequence (Chabregas et al., 2001). Because of this and other information on protein localization of other enzymes in thiamine synthesis, it appears that plant nuclear genes encode thiamine B1 synthesis enzymes. The transcripts are translated on cytoplasmic ribosomes, but thiamine B1 synthesis itself takes place primarily in organellar compartments. AtThi1 is only a secondary target for functional inactivation, because its complex biochemical activities are still poorly defined.

AtThi2 and AtThi3: Yeast Thi6 is a 540 amino acid bifunctional enzyme acting as both a phosphomethylpyrimidine kinase and a hydroxyethylthiazole kinase (FIG. 9). Its N-terminal half is homologous to *E. coli* ThiE, phosphomethylpyrimidine kinase (Table 1). The C-terminal half of yeast Thi6 is homologous to *E. coli* Thi4, a hydroxyethylthiazole kinase. Using the yeast Thi6 sequence as a query, we detected two proteins in *Arabidopsis*, NP_172707 and NP_189045, and found homology to the N-terminal and C-terminal halves of the Thi6 query (see Table 1), respectively. We have named these sequences AtThi2 and AtThi3, respectively. AtThi2 and AtThi3 are very different in length (525 and 276 amino acids) and are not homologous to each other. AtThi2 is about the same length as yeast Thi6, but only has homology in its N-terminal half. Using the C-terminal 250 amino acids of AtThi2 as a query against all sequences, we found a thiamine phosphate pyrophosphorylase sequence (thiE, NP_579063) from *Pyrococcus furiosus* as the most homologous of many non-plant sequences that are significantly related to this *Arabidopsis* query (E-value=e-35). In addition, using the yeast thiamine phosphate pyrophosphorylase Thi22 (Goffeau et al., 1996), we found a single *Arabidopsis* homologue, and it was again the C-terminal, 250 amino acid end of AtThi2 (NP_173707, Table 1, and see below). Without wishing to be bound by any particular theory, we have concluded that AtThi2 is a different bifunctional enzyme than yeast Thi6. AtThi2 combines an N-terminal phosphomethylpyrimidine kinase with a C-terminal thiamine phosphate pyrophosphorylase (thiamine synthase). Similarly, and again without wishing to be bound by theory, we have concluded that AtThi3 is a mono-functional hydroxyethylthiazole kinase, corresponding to the C-terminal portion of the bifunctional yeast Thi6.

TABLE 1

Arabidopsis sequence targets to block thiamine B1 biosynthesis

| Thi sequence query[a]/ Organism | Ath homolog[b] Accession # Length a.a. | (# seq.) E value | % ID | Length hom. a.a./ query | Comments/Reference |
|---|---|---|---|---|---|
| Thi2 (nmt2) NP_596642 S. pombe | NP_200288 349 a.a. AtThi1 | (1)3e-93 | 65% | 266/328 | (Manetti et al., 1994) Thi1 Ath (Machado et al., 1996; Machado et al., 1997; Chabregas et al., 2001) |
| Thi4 S25321 NP_011660 yeast | ARA6, Thi1, NP_200288 349 a.a. | 3e-77 | 50%- | 310-100/ 326 | thiamin biosynthesis protein thi4, thiozole biosyn. |
| Thi2p NP_009799 yeast | No sig. homologue | >0.2 | | 450 | Ts activator of Thi B1 genes |
| Thi6 NP_015110 N-terminal domain C-terminal domain yeast | NP_173707 525 a.a. AtThi2 C-terminus NP_189045 276 a.a. AtThi3 | (1)7e-28 (1)2e-20 | 37% 30% | 225/540 240/540 | Phosphomethypyrimidine kinase. Homology to a.a. 9-233 of query hydroxyethylthiazole kinase, putative, Homology to a.a. 255-523 of query |
| ThiE NP_312943 E. coli | NP_173707 525 a.a. AtThi2 C-term | 2e-11 | 33% | 185/211 | Phosphomethypyrimidine kinase |
| Thi4 NP_416607 E. coli | NP_189045 276 a.a. AtThi3 | 9e-43 | 42% | 240/262 | hydroxyethylthiazole kinase |
| Thi22, NP_015446 yeast. (S. pombe Pho4) | NP_173707 525 a.a. AtThi2 N-terminus | (1) e-35 | 33% | 274/572 C-term | See AtThi2 above, Also Brassica BTH1 thiamine phosphate pyrophosphorylase |
| THI80 P35202 yeast | NP_563669 264 a.a. AtThi5 | (4) 2e-17:4e-8 | 26% | 270/319 a.a. | Thiamine pyrophoshokinase (TPK) Thiamine kinase, unknown |
| Thi3 BAA04886 & Thi3p NP_010203 yeast | B1 binding motif | (12) 3e-65:5e-9 | 29-22% | (8) 550/568 & 609 | Yeast: Thiamine positive regulatory factor, Thiamine binding motif. Arabidopsis pyruvate decarboxylase (Nishimura et al., 1992) |
| Pyruvate decarboxylase PO6169 yeast | NP_195752 | (12) 4e-78:7e-7 | 33%-31% | 560/563 | Pyruvate decarboxylase, oxal-CoA decarboxylase |

[a]Protein sequence from E. coli, S. cerevisiae, or S. pombe used as a query of the Arabidopsis genomic sequences.
[b]Predicted Arabidopsis protein sequence with homology detected in gDNA database (Arabidopsis Genome Initiative, 2000). For the purpose of clarity in identification of the Arabidopsis sequences, we will use Ath as a precursor to all Arabidopsis gene names.
[c]Number of predicted and distinct protein sequences with clear homology (N) followed by the range in E-values.

AtThi5: Thiamine pyrophosphate kinase (TPK, thiamine kinase) makes the pyrophosphate modified form of thiamine B1. Using the yeast gene THI80 (TPK) as a query, four Arabidopsis sequences with significant sequence homology were detected (Table 1). All four sequences may encode nearly identical proteins with truncations at the N-terminus. These proteins are believed to represent the products of a single gene, that we call AtThi5, with multiple allelic cDNAs. We have not yet confirmed whether all four sequences are in the same chromosomal location (same gene) or if they have significant silent nucleotide substitution differences and represent different genes. Yeast thi80 mutants have less thiamine, but are viable (Nishimura et al., 1991; Nosaka et al., 1993). However, because Thi80 is not an essential gene in yeast, the Arabidopsis homologue(s) has not been chosen as a target for functional inactivation.

AtPDC2: There are alternative or supplementary methods of creating TDCS in addition to blocking the synthesis of thiamine biosynthetic enzymes. Thiamine B1 can be sequestered in reproductive tissue, similar to the strategy using avidin to sequester biotin and thus create biotin-deficiency based male sterility (Albertsen and Howard, 1999). Although there is no precedent for generating sufficient thiamine sequestration capacity with a binding protein to create a deficiency, this concept is straightforward, as described herein. There is a thiamine binding protein activity found in plant seeds (Watanabe et al., 1998; Rapala-Kozik et al., 1999), but the genes and proteins for this activity are not identified. The well-characterized enzyme pyruvate decarboxylase (PDC) contains a strong thiamine B1 binding site. Three-dimensional models are available for PDCs from bacteria, fungi, and plants (Konig et al., 1998; Lu et al., 2000). PDC binds its thiamine B1 cofactor at the interface between two homodimeric subunits. Thiamine binding and subunit assembly appear to require the substrate pyruvate or an analogue. However, we believe that expression of large amounts of active PDC enzyme damages the efficiency of central metabolism. Thus, expression of an altered form of PDC that binds thiamine, but is enzymatically inactive, in plant reproductive tissue results in a sterile phenotype. The thiamine binding site is immediately adjacent to the pyruvate binding site. Mutant analysis of the bacterial enzyme from *Zymomonas mobilis* has yielded relevant and exciting results. Chang et al., 1999 have characterized several mutant active site mutant enzymes with a lower $K_m$ for substrate, most of which exhibit a lower affinity for thiamine. One PDC2 mutant with a single E473Q amino acid change lowers the specific activity to 0.025% of wild-type PDC levels (i.e., a 4000 fold reduction in activity), but appears to have an even tighter binding to thiamine than wild-type enzyme. Wild-type PDC has a $k_c$ for thiamine of 1.97 µM, while the release rate of thiamine from mutant enzyme $PDC_{E473Q}$ was too low to be measured. The affinity of $PDC_{E473Q}$ for thiamine is believed to be comparable to that of avidin for biotin. There is a strong sequence identity between the bacterial PDC and AtPDC2 in the region of bacterial residue $E_{473}$. Thus, thiamine sequestration results from the tissue specific expression of a catalytically inactive, thiamine binding mutant AtPDC2 (E517Q) to achieve TDCS. Thiamine sequestration based-sterility can stand alone or be used to supplement to genetic means for inactivating thiamine synthesis, for example, using interference RNA or antisense.

Interference RNA (RNAi) can be used to suppress a gene activity by targeting an mRNA for efficient degradation (Chuang and Meyerowitz, 2000). A single RNA transcript is constructed so that the double stranded mRNA stem of its stem-loop structured RNA product is homologous to part of the target mRNA to be suppressed. This sets up a cycle of efficient target mRNA degradation.

Pollen and ovule tissue-specific expression with the actin promoters and the lacO system can be engineered. The tissue specific expression patterns of the specifically exemplified regulated LacIn and RNAi (or other deleterious gene) constructs are cloned into vectors for transfer to plant cells. These constructs inactivate thiamine B1 biosynthesis in the relevant tissue, for example pollen producing tissue, producing a conditionally sterile phenotype in the absence of repressor synthesis.

TABLE 2

Promoters for reproductive and vegetative tissue-specific expression.

| Vector | Major tissue-specific expression | Origin |
| --- | --- | --- |
| ACT11pt | Most reproductive tissues- embryo, ovule, seed, silique, mature pollen | Arabidopsis ACT11 actin gene |
| ACT12pt | Mature pollen | Arabidopsis ACT12 actin gene |

ACT12 is the most tightly regulated of the *Arabidopsis* actin genes. It is expressed almost exclusively late in pollen development (Huang et al., 1996). The Act12pt, ACT12::lacIn, Act12pot (isolate 5) and ACT12pot::GUS vectors are shown in Tables 4, 5, 6 and 7; see also SEQ ID NO:17, SEQ ID NO:18, SEQ ID NO:19, SEQ ID NO:20 and SEQ ID NO:21, respectively. Primers used in the modification of A12pt to produce A12pot include

```
Act12p-LacO1S
G AAA TTT TTG AAA CCC AAT TTC AGG      (SEQ ID NO:21)

GCA gtg gaa ttg tga gcg gat aac aat t TCT AGA TCT ACG TAA ATT CAT CAG

GTA and

Act12p-LacO1S
TGC CCT GAA ATT GGG TTT CAA AAA TTT    (SEQ ID NO:22)

C aat tgt tat ccg ctc aca att cca c

TTA ATA TCG TTC ATA CAC GGG TCT.
```

The sequence of Act 11pt is given in Table 8 and in SEQ ID NO:23.

Thi2- and Thi3-RNAi constructs expressed from the ACT12pt vector prevent the growth of mature pollen and block fertilization. Another suitable pollen-specific promoter is the Lat52p (Preuss et al., 1994). The constitutive ACT2 actin promoter cassette ACT2pt is used as a control to express the RNAi constructs in all vegetative tissues to make plants that do not grow at all without added thiamine.

The Thi-RNAi (or other deleterious gene) constructs are transformed or cotransformed into *Arabidopsis* via vacuum infiltration of each regulated RNAi construct subcloned into an *Agrobacterium* T-DNA plasmid (Bariola et al., 1999). The construct is subcloned into pCambia1300 (or other suitable plant vector) with a hygromycin or other selectable marker. pCAMBIA 1300 and numerous other vectors for cloning and stable introduction of transgenes into plants are available from CAMBIA (Black Mountain, ACT, Australia) and other sources. Where pBIN10 is used, selection is for kanamycin resistance. The Thi3-RNAi construct is subcloned into the pBIN19 vector with a kanamycin drug marker for plant selection (Bevan, 1984). A basta selection system can also be used. With such transformations, progeny show between 0.1 and 2% of the seed to be transformed based on Hyg or Kan drug selection, and no non-transformed seeds escaped selection and grow. Plants doubly transformed with mixtures of *Agrobacterium* strains containing independent KanR and HygR plasmids are co-transformed at a rate of about 60%. When two different *Agrobacterium* populations carrying different T-DNAs are mixed and vacuum infiltrated together, their T-DNA transgenes are efficiently co-transformed into the same plants. Co-transformation saves three months over transforming the two genes in two successive separate rounds of transformation. The T1 generation of vacuum infiltrated transformed seed from the single and double Thi gene transformations are plated on media containing MS salts, the appropriate drugs for selection, and thiamine. Plants with one or both drug markers, expressing Thi2-RNAi, Thi3-RNAi or both Thi2-RNAi and Thi3-RNAi constructs, and/or the LacIn construct, are characterized further for TDCS phenotypes.

The molecular model for Thi-RNAi suppression in these experiments is that the AtThi2 and AtThi3 mRNAs are degraded in reproductive tissues in which the LacI or LacIn repressor protein is not expressed. RNA degradation results from the dsRNA structure of the transcript initiating a cycle of target mRNA degradation into small 23-24 nt RNA fragments, as described for several example cases (Hamilton and Baulcombe, 1999). AtThi2 and AtThi3 activities are functionally inactivated by this RNAi approach in a tissue specific fashion. One reason we are producing doubly suppressed lines for AtThi2 and AtThi3 is that the efficiency of blocking the thiamine biosynthesis is then be the multiple of the two phenotypes. In other words, the suppressed phenotype is stronger if two genes are inactivated instead of just one. In addition, AtThi2 encodes a bifunctional enzyme, further strengthening the suppression of thiamine synthesis. If each of the three enzymes are suppressed to 10% of normal levels then the thiamine pathway is blocked to 0.1% of normal levels (i.e., $f=(0.1)^3=0.001$).

AtThi2, AtThi3, and AtPDC2 are soluble enzymes that are sequence homologues of bacterial sequences. Their mRNAs are translated in the cytoplasm and are specifically targeted to the prokaryotic environments (e.g., chloroplast and mitochondria). Therefore, they are efficiently expressed as native proteins in E. coli. A PCR amplified cDNA sequence is cloned which encodes Arabidopsis AtThi2 and AtThi3 without their organellar target peptides of 20 and 21 amino acids that are removed during organellar transport in plants. ATPDC2 cDNA is amplified from Arabidopsis total plant cDNA. The three sequences are given in SEQ ID NO:24, 25 and 26.

Commercially available pBluescript and pET expression vectors are used. Appropriate bacterial stop codons (for LacZ), Shine-Delgarno sequences and cloning sites are added during PCR as described in publications including Kandasamy et al., 1999; McKinney et al., 2001; and McKinney et al., 2002.

We have identified two Arabidopsis targets, AtThi2 and AtThi3, to suppress thiamine biosynthesis and one protein product $PDC_{E473Q}$ to sequester thiamine. Together the two Thi genes determine three essential enzymatic steps in thiamine synthesis. The genes are inactivated individually or together by an RNAi strategy using a tissue-specific lac-regulated promoter system. In bacteria and yeast, the mutant form of the enzyme $PDC_{E473Q}$ has lost 99% of its enzyme activity but has greatly enhanced binding capacity for thiamine. This strong binding should sequester any thiamine present in these cells, including any that is transported in from adjacent tissues. Thiamine-deficient plants are shown to have a male-female sterile or male-sterile TDCS phenotypes depending upon the promoter used. The TDCS phenotypes are rescued by direct application of thiamine to the plants or their soil. This system can be applied to TDCS trees, shrubs, and grasses to enhance there use in phytoremediation of toxic elements and organics such as our previously described mercury and arsenic resistant plants (Meagher, 2000; Meagher et al., 2000; Bizily et al., 2002; Dhankher et al., 2002). This flexible system of TDCS is also easily applied to forestry for more efficient wood or fiber production and to the hybrid seed industry as well.

Targeted gene suppression in plants can be achieved through the induction of RNA interference (RNAi), also known as post-transcriptional gene silencing. This is accomplished through in vivo production of an RNA species containing a double stranded region composed of sequence homologous to a segment of the mRNA to be targeted. Production of this dsRNA leads to the induction of RNAi and subsequence degradation of the corresponding mRNA.

The amino acids which occur in the various amino acid sequences referred to in the specification have their usual three- and one-letter abbreviations routinely used in the art: A, Ala, Alanine; C, Cys, Cysteine; D, Asp, Aspartic Acid; E, Glu, Glutamic Acid; F, Phe, Phenylalanine; G, Gly, Glycine; H, His, Histidine; I, Ile, Isoleucine; K, Lys, Lysine; L, Leu, Leucine; M, Met, Methionine; N, Asn, Asparagine; P, Pro, Proline; Q, Gln, Glutamine; R, Arg, Arginine; S, Ser, Serine; T, Thr, Threonine; V, Val, Valine; W, Try, Tryptophan; Y, Tyr, Tyrosine.

A protein is considered an isolated protein if it is a protein isolated from a host cell in which it is recombinantly produced. It can be purified or it can simply be free of other proteins and biological materials with which it is associated in nature.

An isolated nucleic acid is a nucleic acid the structure of which is not identical to that of any naturally occurring nucleic acid or to that of any fragment of a naturally occurring genomic nucleic acid spanning more than three separate genes. The term therefore covers, for example, a DNA which has the sequence of part of a naturally occurring genomic DNA molecule but is not flanked by both of the coding or noncoding sequences that flank that part of the molecule in the genome of the organism in which it naturally occurs; a nucleic acid incorporated into a vector or into the genomic DNA of a prokaryote or eukaryote in a manner such that the resulting molecule is not identical to any naturally occurring vector or genomic DNA; a separate molecule such as a cDNA, a genomic fragment, a fragment produced by polymerase chain reaction (PCR), or a restriction fragment; and a recombinant nucleotide sequence that is part of a hybrid gene, i.e., a gene encoding a fusion protein. Specifically excluded from this definition are nucleic acids present in mixtures of DNA molecules, transformed or transfected cells, and cell clones, e.g., as these occur in a DNA library such as a cDNA or genomic DNA library.

As used herein expression directed by a particular sequence is the transcription of an associated downstream target sequence. If appropriate and desired for the associated target sequence, there the term expression also encompasses translation (protein synthesis) of the transcribed target RNA. When expression of a target sequence of interest is up-regulated, the expression is increased. With reference to up-regulation of expression of a target sequence of interest operably linked to a transcription regulatory sequence, expression is increased. Down regulation refers to decreased expression or a coding or other functional sequence of interest.

A coding sequence is one which when transcribed, directs the translation of a protein of interest. A functional sequence (other than a coding sequence) is one which after transcription has a particular activity. A ribozyme cuts an RNA molecule, an antisense RNA or interfering RNA lowers expression of a protein of interest, for example.

In the present context, a promoter is a DNA region, which includes sequences sufficient to cause transcription of an associated (downstream) sequence. The promoter may be regulated, i.e., constitutively acting to cause transcription of the associated target sequence in all not plant tissues. If inducible, there are sequences present which mediate regulation of expression so that the associated target sequence is transcribed only when an inducer molecule is present in the medium in or on which the organism is cultivated. In the present context, a transcription regulatory sequence includes a promoter sequence and can further include cis-active sequences for regulated expression of an associated target sequence (or the Lac or LacIn repressor) in response to environmental signals. Tissue- and/or organ-specific transcription regulatory sequences can be associated with the repressor coding sequence so as to determine the parts of the plant in which the repressor is expressed, thus preventing expression of the target sequence in those tissues or organs.

One DNA portion or sequence is downstream of second DNA portion or sequence when it is located 3' of the second sequence. One DNA portion or sequence is upstream of a second DNA portion or sequence when it is located 5' of that sequence.

One DNA molecule or sequence and another are heterologous to another if the two are not derived from the same ultimate natural source. The sequences may be natural sequences, or at least one sequence can be designed by man, as in the case of a multiple cloning site region. The two sequences can be derived from two different species or one sequence can be produced by chemical synthesis provided that the nucleotide sequence of the synthesized portion was not derived from the same organism as the other sequence.

An isolated or substantially pure nucleic acid molecule or polynucleotide is a polynucleotide which is substantially separated from other polynucleotide sequences which naturally accompany a native transcription regulatory sequence. The term embraces a polynucleotide sequence which has been removed from its naturally occurring environment, and includes recombinant or cloned DNA isolates, chemically synthesized analogues and analogues biologically synthesized by heterologous systems.

A polynucleotide is said to encode a polypeptide if, in its native state or when manipulated by methods known to those skilled in the art, it can be transcribed and/or translated to produce the polypeptide or a fragment thereof. The anti-sense strand of such a polynucleotide is also said to encode the sequence.

A nucleotide sequence is operably linked when it is placed into a functional relationship with another nucleotide sequence. For instance, a promoter is operably linked to a coding sequence if the promoter effects its transcription or expression. Generally, operably linked means that the sequences being linked are contiguous and, where necessary to join two protein coding regions, contiguous and in reading frame. However, it is well known that certain genetic elements, such as enhancers, may be operably linked even at a distance, i.e., even if not contiguous.

The term recombinant (or chimeric) polynucleotide refers to a polynucleotide which is made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

Polynucleotide probes include an isolated polynucleotide attached to a label or reporter molecule and may be used to identify and isolate other sequences. Probes comprising synthetic oligonucleotides or other polynucleotides may be derived from naturally occurring or recombinant single or double stranded nucleic acids or chemically synthesized. Polynucleotide probes may be labeled by any of the methods known in the art, e.g., random hexamer labeling, nick translation, or the Klenow fill-in reaction.

Large amounts of the polynucleotides may be produced by replication in a suitable host cell. Natural or synthetic DNA fragments coding for a protein of interest are incorporated into recombinant polynucleotide constructs, typically DNA constructs, capable of introduction into and replication in a prokaryotic or eukaryotic cell. Usually the construct is suitable for replication in a unicellular host, such as *S. cerevisiae* or a bacterium, but a multicellular eukaryotic host may also be appropriate, with or without integration within the genome of the host cell. Commonly used prokaryotic hosts include strains of *Escherichia coli*, although other prokaryotes, such as *Bacillus subtilis* or a pseudomonad, may also be used. Eukaryotic host cells include yeast, filamentous fungi, plant, insect, amphibian and avian species.

The polynucleotides may also be produced by chemical synthesis, e.g., by the phosphoramidite method described by Beaucage and Caruthers (1981) Tetra. Letts., 22: 1859-1862 or the triester method according to Matteuci et al. (1981) J. Am. Chem. Soc., 103: 3185, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

A coding sequence is one which, when transcribed, directs the translational expression of a polypeptide. There is a translation start codon, usually ATG or AUG, at the 5' end and a translation termination codon at the 3' end of the sequence, usually, TAG, UAG, TGA, UGA, TAA, or UAA.

As used in the present context, a functional sequence is one with biological activity after transcription. The transcribed RNA can have the function of antisense, interference or suppressing RNA, among others.

DNA constructs prepared for introduction into a prokaryotic or eukaryotic host will typically comprise a replication system (i.e. vector) recognized by the host, including the intended DNA fragment encoding the desired polypeptide, and will preferably also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included where appropriate from secreted polypeptides of the same or related species, which allow the protein to cross and/or lodge in cell membranes or be secreted from the cell.

An appropriate promoter and other necessary vector sequences are selected so as to be functional in the host. Examples of workable combinations of cell lines and expression vectors are described in Sambrook et al. (1989) vide infra; Ausubel et al. (Eds.) (1995) Current Protocols in Molecular Biology, Greene Publishing and Wiley Interscience, New York; and Metzger et al. (1988) Nature, 334: 31-36. Many useful vectors for expression in bacteria, yeast, fungal, mammalian, insect, plant or other cells are well known in the art and may be obtained such vendors as Stratagene, New England Biolabs, Promega Biotech, and others. In addition, the construct may be joined to an amplifiable gene (e.g., DHFR) so that multiple copies of the gene may be made. For appropriate enhancer and other expression control sequences, see also Enhancers and Eukaryotic Gene Expression, Cold Spring Harbor Press, NY (1983). While such expression vectors may replicate autonomously, they may less preferably replicate by being inserted into the genome of the host cell.

Expression and cloning vectors usually contain a selectable marker, that is, a gene encoding a protein necessary for the survival or growth of a host cell transformed with the vector. Although such a marker gene may be carried on another polynucleotide sequence co-introduced into the host cell, it is most often contained on the cloning vector. Only those host cells into which the marker gene has been introduced will survive and/or grow under selective conditions. Typical selection genes encode proteins that confer resistance to antibiotics or other toxic substances, e.g., ampicillin, neomycin, methotrexate, etc.; complement auxotrophic deficiencies; or supply critical nutrients not available from complex media. The choice of the proper selectable marker will depend on the host cell; appropriate markers for different hosts are known in the art.

Recombinant host cells, in the present context, are those which have been genetically modified to contain an isolated DNA molecule of the instant invention. The DNA can be introduced by any means known to the art, which is appropriate for the particular type of cell, including without limitation, transformation, lipofection or electroporation.

It is recognized by those skilled in the art that the DNA sequences may vary due to the degeneracy of the genetic code and codon usage. As known in the art, a synonymous coding sequence can be designed where codons are chosen for optimum translational efficiency in a particular host cell. See, e.g., Murray et al. (1989) Nucl. Acids Res. 17:477-484.

Additionally, it will be recognized by those skilled in the art that allelic variations may occur in the DNA sequences which will not significantly change activity of the amino acid sequences of the peptides which the DNA sequences encode. All such equivalent DNA sequences are included within the scope of this invention and the definition of the regulated promoter region. The skilled artisan will understand that the sequence of the exemplified sequence can be used to identify and isolate additional, nonexemplified nucleotide sequences which are functionally equivalent to the sequences given.

Hybridization procedures are useful for identifying polynucleotides with sufficient homology to the subject regulatory sequences to be useful as taught herein. The particular hybridization techniques is not essential to the subject invention. As improvements are made in hybridization techniques, they can be readily applied by one of ordinary skill in the art.

A probe and sample are combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting. As is well known in the art, if the probe molecule and nucleic acid sample hybridize by forming a strong non-covalent bond between the two molecules, it can be reasonably assumed that the probe and sample are essentially identical, or completely complementary if the annealing and washing steps are carried out under conditions of high stringency. The probe's detectable label provides a means for determining whether hybridization has occurred. Detection can be effected using a chromophore or fluorescent moiety bound to or incorporated within the probe, primer or amplification product, as well known in the art. Alternatively, a ligand for a detectable molecule bound in a subsequent reaction can also be employed.

In the use of the oligonucleotides or polynucleotides as probes, the particular probe is labeled with any suitable label known to those skilled in the art, including radioactive and non-radioactive labels. Typical radioactive labels include $^{32}P$, $^{35}S$, or the like. Non-radioactive labels include, for example, ligands such as biotin or thyroxine, as well as enzymes such as hydrolases or peroxidases, or a chemiluminescer such as luciferin, or fluorescent compounds like fluorescein and its derivatives. Alternatively, the probes can be made inherently fluorescent as described in WO 93/16094.

Various degrees of stringency of hybridization can be employed. The more stringent the conditions, the greater the complementarity that is required for duplex formation. Stringency can be controlled by temperature, probe concentration, probe length, ionic strength, time, and the like. Preferably, hybridization is conducted under moderate to high stringency conditions by techniques well know in the art, as described, for example in Keller, G. H., M. M. Manak (1987) DNA Probes, Stockton Press, New York, N.Y., pp. 169-170, hereby incorporated by reference.

As used herein, moderate to high stringency conditions for hybridization are conditions which achieve the same, or about the same, degree of specificity of hybridization as the conditions employed by the current inventors. An example of high stringency conditions are hybridizing at 68° C. in 5×SSC/5× Denhardt's solution/0.1% SDS, and washing in 0.2×SSC/0.1% SDS at room temperature. An example of conditions of moderate stringency are hybridizing at 68° C. in 5×SSC/5× Denhardt's solution/0.1% SDS and washing at 42° C. in 3×SSC. The parameters of temperature and salt concentration can be varied to achieve the desired level of sequence identity between probe and target nucleic acid. See, e.g., Sambrook et al. (1989) vide infra or Ausubel et al. (1995) Current Protocols in Molecular Biology, John Wiley & Sons, NY, N.Y., for further guidance on hybridization conditions.

Specifically, hybridization of immobilized DNA in Southern blots with $^{32}P$-labeled gene specific probes was performed by standard methods (Maniatis et al.) In general, hybridization and subsequent washes were carried out under moderate to high stringency conditions that allowed for detection of target sequences with homology to the exemplified sequences. For double-stranded DNA gene probes, hybridization can be carried out overnight at 20-25° C. below the melting temperature (Tm) of the DNA hybrid in 6×SSPE 5× Denhardt's solution, 0.1% SDS, 0.1 mg/ml denatured DNA. The melting temperature is described by the following formula (Beltz, G. A., Jacobe, T. H., Rickbush, P. T., Chorbas, and F. C. Kafatos [1983] Methods of Enzymology, R. Wu, L, Grossman and K Moldave [eds] Academic Press, New York 100:266-285).

Tm=81.5° C.+16.6 Log [Na+]+0.41(+G+C)−0.61(% formamide)−600/length of duplex in base pairs.

Washes are typically carried out as follows: twice at room temperature for 15 minutes in 1×SSPE, 0.1% SDS (low stringency wash), and once at TM−20° C. for 15 minutes in 0.2×SSPE, 0.1% SDS (moderate stringency wash).

For oligonucleotide probes, hybridization was carried out overnight at 10-20° C. below the melting temperature (Tm) of the hybrid 6×SSPE, 5× Denhardt's solution, 0.1% SDS, 0.1 mg/ml denatured DNA. Tm for oligonucleotide probes was determined by the following formula: TM(° C.)=2(number T/A base pairs +4(number G/C base pairs) [Suggs, S. V., T. Miyake, E. H., Kawashime, M. J. Johnson, K. Itakura, and R. B. Wallace (1981) ICB-UCLA Symp. Dev. Biol. Using Purified Genes, D. D. Brown (ed.), Academic Press, New York, 23:683-693].

Washes were typically carried out as follows: twice at room temperature for 15 minutes 1×SSPE, 0.1% SDS (low stringency wash), and once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used: Low, 1 or 2×SSPE, room temperature; Low, 1 or 2×SSPE, 42° C.; Moderate, 0.2× or 1×SSPE, 65° C.; and High, 0.1×SSPE, 65° C.

Duplex formation and stability depend on substantial complementarity between the two strands of a hybrid, and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and those methods are known to an ordinarily skilled artisan. Other methods may become known in the future.

Mutational, insertional, and deletional variants of the disclosed nucleotide and protein sequences can be readily prepared by methods which are well known to those skilled in the art. These variants can be used in the same manner as the exemplified polynucleotide and protein sequences so long as the variants have substantial sequence identity with the original sequence. As used herein, substantial sequence identity refers to identity (sometimes termed homology) which is sufficient to enable the variant polynucleotide or protein to function in the same capacity as the polynucleotide or protein from which the variant was derived. Preferably, this identity is greater than 80%, more preferably, this identity is greater than 85%, even more preferably this identity is greater than 90%, and most preferably, this identity is greater than 95%. The degree of identity needed for the variant to function in its intended capacity depends upon the intended use of the sequence. It is well within the skill of a person trained in this art to make mutational, insertional, and deletional mutations which are equivalent in function or are designed to improve the function of the sequence or otherwise provide a methodological advantage. Methods for confirming promoter activity, organ specificity or tissue specificity and regulation are known in the art. Algorithms for calculating sequence identity are well known to the art.

Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki et al. (1985) Science 230:1350-1354). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA template produced in the previous cycle. This results in the exponential accumulation of the specific target fragment, up to several million-fold in a few hours. By using a thermostable DNA polymerase such as the Taq polymerase, which is isolated from the thermophilic bacterium *Thermus aquaticus*, the amplification process can be completely automated. Other enzymes which can be used are known to those skilled in the art.

A DNA construct carrying a plant-expressible gene or other DNA of interest can be inserted into the genome of a plant by any suitable method. Such methods may involve, for example, the use of liposomes, electroporation, diffusion, particle bombardment, microinjection, gene gun, chemicals that increase free DNA uptake, e.g., calcium phosphate coprecipitation, viral vectors, and other techniques practiced in the art. Suitable plant transformation vectors include those derived from a Ti plasmid of *Agrobacterium tumefaciens*, such as those disclosed by Herrera-Estrella (1983), Bevan (1983), Klee (1985) and EPO publication 120,516 (Schilperoort et al.). In addition to plant transformation vectors derived from the Ti or root-inducing (Ri) plasmids of *Agrobacterium*, alternative methods can be used to insert the DNA constructs of this invention into plant cells.

The choice of vector in which the DNA of interest is operatively linked depends directly, as is well known in the art, on the functional properties desired, e.g., replication, protein expression, and the host cell to be transformed, these being limitations inherent in the art of constructing recombinant DNA molecules. The vector desirably includes a prokaryotic replicon, i.e., a DNA sequence having the ability to direct autonomous replication and maintenance of the recombinant DNA molecule extra-chromosomally when introduced into a prokaryotic host cell, such as a bacterial host cell. Such replicons are well known in the art. In addition, preferred embodiments that include a prokaryotic replicon also include a gene whose expression confers a selective advantage, such as a drug resistance, to the bacterial host cell when introduced into those transformed cells. Typical bacterial drug resistance genes are those that confer resistance to ampicillin or tetracycline, among other selective agents. The neomycin phosphotransferase gene has the advantage that it is expressed in eukaryotic as well as prokaryotic cells.

Those vectors that include a prokaryotic replicon also typically include convenient restriction sites for insertion of a recombinant DNA molecule of the present invention. Typical of such vector plasmids are pUC8, pUC9, pBR322, and pBR329 available from BioRad Laboratories (Richmond, Calif.) and pPL, pK and K223 available from Pharmacia (Piscataway, N.J.), and pBLUESCRIPT and pBS available from Stratagene (La Jolla, Calif.). A vector of the present invention may also be a Lambda phage vector including those Lambda vectors described in Molecular Cloning: A Laboratory Manual, Second Edition, Maniatis et al., eds., Cold Spring Harbor Press (1989) and the Lambda ZAP vectors available from Stratagene (La Jolla, Calif.). Other exemplary vectors include pCMU [Nilsson et al. (1989) Cell 58:707]. Other appropriate vectors may also be synthesized, according to known methods; for example, vectors pCMU/$K^b$ and pCMUII used in various applications herein are modifications of pCMUIV (Nilson et al., supra).

Typical expression vectors capable of expressing a recombinant nucleic acid sequence in plant cells and capable of directing stable integration within the host plant cell include vectors derived from the tumor-inducing (Ti) plasmid of *Agrobacterium tumefaciens* described by Rogers et al. (1987) Meth. in Enzymol. 153:253-277, and several other expression vector systems known to function in plants. See for example, Verma et al., No. WO87/00551; Cocking and Davey (1987) Science 236:1259-1262.

A transgenic plant can be produced by any means known to the art, including but not limited to *Agrobacterium tumefaciens*-mediated DNA transfer, preferably with a disarmed T-DNA vector, electroporation, direct DNA transfer, and particle bombardment (See Davey et al. (1989) Plant Mol. Biol. 13:275; Walden and Schell (1990) Eur. J. Biochem. 192:563; Joersbo and Burnstedt (1991) Physiol. Plant. 81:256; Potrykus (1991) Annu. Rev. Plant Physiol. Plant Mol. Biol. 42:205; Gasser and Fraley (1989) Science 244:1293; Leemans (1993) Bio-Technology 11:522; Beck et al. (1993) Bio/Technology 11:1524; Koziel et al. (1993) Bio/Technology 11:194; and Vasil et al. (1993) Bio/Technology 11:1533.). Techniques are well-known to the art for the introduction of DNA into monocots as well as dicots, as are the techniques for culturing such plant tissues and regenerating those tissues.

Techniques and agents for introducing and selecting for the presence of heterologous DNA in plant cells and/or tissue are well-known. Genetic markers allowing for the selection of heterologous DNA in plant cells are well-known, e.g., genes carrying resistance to an antibiotic such as kanamycin, hygromycin, gentamicin, or bleomycin. The marker allows for selection of successfully transformed plant cells growing in the medium containing the appropriate antibiotic because they will carry the corresponding resistance gene. In most cases the heterologous DNA which is inserted into plant cells contains a gene which encodes a selectable marker such as an antibiotic resistance marker, but this is not mandatory. An exemplary drug resistance marker is the gene whose expression results in kanamycin resistance, i.e., the chimeric gene containing nopaline synthetase promoter, Tn5 neomycin phosphotransferase II and nopaline synthetase 3' non-translated region described by Rogers et al., Methods for Plant Molecular Biology, A. Weissbach and H. Weissbach, eds., Academic Press, Inc., San Diego, Calif. (1988).

Techniques for genetically engineering plant cells and/or tissue with an expression cassette comprising an inducible promoter or chimeric promoter fused to a heterologous coding sequence and a transcription termination sequence are to be introduced into the plant cell or tissue by Agrobacterium-mediated transformation, electroporation, microinjection, particle bombardment or other techniques known to the art. The expression cassette advantageously further contains a marker allowing selection of the heterologous DNA in the plant cell, e.g., a gene carrying resistance to an antibiotic such as kanamycin, hygromycin, gentamicin, or bleomycin.

Monoclonal or polyclonal antibodies, preferably monoclonal, specifically reacting with a polypeptide or protein of interest may be made by methods known in the art. See, e.g., Harlow and Lane (1988) Antibodies: A Laboratory Manual, Cold Spring Harbor Laboratories; Goding (1986) Monoclonal Antibodies: Principles and Practice, 2d ed., Academic Press, New York; and Ausubel et al. (1993) Current Protocols in Molecular Biology, Wiley Interscience, New York, N.Y.

Many of the procedures useful for practicing the present invention, whether or not described herein in detail, are well known to those skilled in the art of plant molecular biology. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) Molecular Cloning, Second Edition, Cold Spring Harbor Laboratory, Plainview, N.Y.; Maniatis et al. (1982) Molecular Cloning, Cold Spring Harbor Laboratory, Plainview, N.Y.; Wu (ed.) (1993) Meth. Enzymol. 218, Part I; Wu (ed.) (1979) Meth. Enzymol. 68; Wu et al. (eds.) (1983) Meth. Enzymol. 100 and 101; Grossman and Moldave (eds.) Meth. Enzymol. 65; Miller (ed.) (1972) Experiments in Molecular Genetics, Cold Spring Harbor Laboratory, Cold Spring Harbor, N.Y.; Old and Primrose (1981) Principles of Gene Manipulation, University of California Press, Berkeley; Schleif and Wensink (1982) Practical Methods in Molecular Biology; Glover (ed.) (1985) DNA Cloning Vol. I and II, IRL Press, Oxford, UK; Hames and Higgins (eds.) (1985) Nucleic Acid Hybridization, IRL Press, Oxford, UK; and Setlow and Hollaender (1979) Genetic Engineering: Principles and Methods, Vols. 1-4, Plenum Press, New York, Kaufman (1987) in Genetic Engineering Principles and Methods, J. K. Setlow, ed., Plenum Press, NY, pp. 155-198; Fitchen et al. (1993) Annu. Rev. Microbiol. 47:739-764; Tolstoshev et al. (1993) in Genomic Research in Molecular Medicine and Virology, Academic Press. Abbreviations and nomenclature, where employed, are deemed standard in the field and commonly used in professional journals such as those cited herein.

Each reference cited herein is incorporated by reference herein to the extent that there is no inconsistency with the present disclosure.

The following examples are provided for illustrative purposes, and are not intended to limit the scope of the invention as claimed herein. Any variations in the exemplified articles which occur to the skilled artisan are intended to fall within the scope of the present invention.

EXAMPLES

Example 1

Plant and Bacterial Growth Conditions

Plants were grown on agar media with MS salts or in soil with 16 h light and 8 h darkness. Agar media was supplemented with various concentrations of mercury chloride ($HgCl_2$) as indicated.

Example 2

Cloning the Bacterial lacI Gene for Plant Expression

A 1072 bp lacI gene coding sequence (GenBank Accession No. AY042185) was PCR amplified from plasmid pSK9118 (pMS421) (Grana et al., 1988). The sense primer LacIs-NcoXho introduced sequences for XhoI and NcoI sites at the AUG initiation codon on the 5' end, and the antisense primer LacIa-NLSBamHind introduced codons for the NLS followed by a translation stop codon and BamHI and HindIII sites at the 3' end of the lacI sequence. This artificial NLS was designed to comprise NLS sequences from the SV40 T-antigen (PKKKRKV, SEQ ID NO:14) (Goldfarb et al., 1986) and ARP7 (SVVHRK, SEQ ID NO:15) (Kandasamy et al., 2003) separated from LacI by helix-breaking SS residues. The amplified LacIn fragment was cleaved by XhoI and HindIII and ligated into the compatible replacement region of pBluescript-SKII (Stratagene) to make the plasmid pLacIn. For plant expression, the lacIn coding sequence was subcloned into the NcoI-HindIII replacement region of the pS1pt plasmid to make S1pt::LacIn. The pS1pt vector contains sequences derived from the soybean light-induced ribulose bisphosphate carboxylase small subunit SRS1 gene, including the promoter, 5' UTR, 3' UTR, and polyadenylation elements and a multilinker for target gene expression. The entire cassette containing the LacIn encoding sequence and SRSI flanking sequences was subcloned into the KpnI and SacI replacement region of pCambia (Hajdukiewicz et al., 1994).

Example 3

Lac-Regulated Actin Promoter Vector

The actin promoter cassette A2pt is composed of the promoter, leader intron, 5' UTR, 3' UTR, and polyadenylation elements from the Arabidopsis ACT2 gene (An et al., 1996; Kandasamy et al., 2002). Two copies of the 25 bp wildtype bacterial lac operator sequence 5'GTGGMTTGT GAGCGGATAA CAATT (SEQ ID NO:16) were substituted for sequences in the ACT2 gene promoter: one immediately following the TATA box and the other following the transcriptional start site as shown in FIG. 2. A two fragment overlap extension PCR mutagenesis strategy was used to assemble the modified ACT2 promoter sequence and replace the corresponding sequences of A2pt. The first round PCR paired sense primer ACT2p-KpnS with antisense primer Act2p-LacO1A and sense primer Act2p-LacO2S with antisense primer ACT2p-1100A. The resulting 814 and 310 bp fragments, respectively, were purified on a 1% agarose gel and assembled in a second round of PCR using the same flanking primers, ACT2p-KpnS and ACT2p-1100A. This fragment was digested with KpnI and EcoRI and cloned into the corresponding replacement region of ACT2pt cassette in pBluescript, creating pA2pot.

Both the GUS and merA sequences were cloned into the new A2pot cassette to make the A2pot::GUS and A2pot::merA genes. The 1800 bp GUS sequence was PCR amplified from pBI221 (Tanaka et al., 1990) using the sense primer GUS-S to add a XbaI site and a NcoI site at the ATG codon and using the antisense primer GUS-A to add XhoI, SacI and BamHI sites (Table I). A modified version of the bacterial merA gene, merA77, was used. The wild-type 1695 bp bacterial merA gene is composed of 68% GC nucleotides and has 213 CpG dinucleotides and was not well suited for transgenic plant expression (Rugh et al., 1998b). The merA77 sequence encodes a wild type MerA protein, but contains 77% synthetic DNA sequences (77% of the coding region was replaced with synthetic sequence to make a gene with only about 50% GC and about 108 CpG dinucleotides) as compared to the 213 CpG dinucleotides in the wildtype merA gene sequence. Overlap extension PCR was used to assemble the merA77 sequence as described for the merA9 sequence (Rugh et al., 1996; Rugh et al., 1998b) but carried out more extensively to make merA77. The merA77 sequence was cloned as a NcoI-BamHI fragment into the corresponding replacement region of the A2pot vector. The KpnI-SacI fragments from both the A2pot::merA and A2pot::GUS clones were moved into the replacement region of pBIN19. merA77 is more consistently expressed at high levels in transgenic plants and is less subject to cosuppression than wild type merA.

The A2pot::GUS, A2pot::MerA, and S1pt::LacIn constructs were introduced alone and together into *Arabidopsis thaliana* (ecotype Columbia) by *Agrobacterium* mediated transformation using the vacuum infiltration procedure (Ye et al., 1999). $T_1$ generation plants were selected for kanamycin resistance encoded by pBIN clones and hygromycin resistance encoded by the pCambia clone of S1pt::LacIn. Plates generally contained 50 to 60 µM kanamycin and 30 µM hygromycin. Selection was carried out in MS media on agar plates for seven days after plating seeds. $T_1$ generation seedlings were then move to nonselective media for two weeks and then transplanted to soil. $T_2$ and $T_3$ generation plants were examined for the phenotypes described herein.

LacI and MerA proteins were assayed on Western blots using polyclonal antibody (Stratagene) and monoclonal antibody (Rugh et al., 1998b), respectively. A GUS protein standard was obtained from Sigma Chemical Co., St. Louis, Mo. Total protein levels in plant extracts were determined as described previously (Kandasamy et al., 1999). β-glucuronidase activity was assayed using 5-chloro-4-bromo-3-indolyl-β-D-glucuronide (x-Gluc, Sigma) and methylumbelliferyl (MUG, Sigma) substrates for visible and fluorescence microscopy, respectively. (See Jefferson et al., 1987; An et al., 1996.) The GUS staining protocol was modified from overnight (16 hr) at 37° C. to only 6 hr to better quantify the extremely high levels of A2pot::GUS expression.

Example 4

Mercury Extraction and Quantification

In order to examine mercury accumulation, three-week-old seedlings are grown on mesh platforms with their roots in hydroponic media containing one half strength MS salts with various levels of mercury. Leaves and roots are harvested separately, washed 3 to 4 times with deionized water, and frozen in liquid nitrogen. The plant samples are lyophilized at −70° C. for 72 h and digested in a mixture of nitric and perchloric acids (7:1 v/v) using standard methods (Suszcynsky and Shann, 1995), and are analyzed for mercury content using Inductively Coupled Plasma-Mass Spectrometry (ICP-MS). In addition, reagent blanks and internal standards were used, where appropriate, to ensure accuracy and precision in the analysis.

Example 5

ROC-Mediated Plant Sterility

A two-gene repressor-operator gene complex (ROC) is combined with the technology enabling thiamine-deficiency based sterility to make conditional male-sterile plants. These plants are useful for hybrid seed production. The ROC for male-sterility is very similar in design to that described herein above for a root-specific ROC expression system.

To construct the male-sterile ROC, the well-characterized actin A12pt pollen specific regulatory vector is modified to contain two lac operator sequences (lacO) to make A12pot. The two approximately 25 bp lacO operators follow the TATA box and flank the transcription start sites, analogous to what was already done to make the actin A2pot vector. The lacO operators replace sequence which was poorly conserved in comparison with the ACT3 promoter region. Essentially any pollen-specific promoter can be modified in this way, provided there is sufficient knowledge about conserved regulatory motifs and non-essential non-conserved sequences.

The A12pot vector is used to express Thi2 and/or Thi3 RNA interference (RNAi) sequences. These vectors make stem loop transcripts in which the double stranded stem target the Thi2 and/or Thi3 transcripts for degradation, leading to male sterility. For example, transformation of A12pot::Thi3Ri into the $A_2A_2$ genome generates hemizygous $A_1A_2$ plants in which thiamine metabolism is disrupted in pollen (see FIG. 8). The T1 generation A12pot::Thi3Ri plants are selected with a linked basta marker that can be sprayed directly on young seedlings germinated in soil. The $A_1A_2$ T1 generation plants are male sterile (i.e., plants expressing A12pt::Thi3). The A12pot::Thi3Ri gene is repressible by LacIn repressor, but no repressor is present in the $A_1A_2$ genomes. Elite line $A_1A_2$ is maintained by crossing it with the fully-fertile $A_2A_2$ parent, and spraying the offspring seedlings with basta to select for $A_1A_2$ hybrids and to kill $A_2A_2$ progeny (see FIG. 8). Any linked herbicide resistance transgene can be used in place of the basta selectable marker.

The second inbred elite line $B_1B_1$ expresses the LacIn repressor from A12pt promoter (A12pt::lacIn). A12pt::lacIn plants synthesize repressor in pollen. Any pollen specific promoter can be used. This line is homozygous for the repressor gene so that all offspring from crosses with $B_1B_1$ make repressor (i.e., both genomes contain the A12pt::lacIn gene). Elite line $B_1B_1$ are fully fertile, because there is no transgene suppressing pollen production. When the two elite lines, $A_1A_2$ and $B_1B_1$, are crossed the resulting hybrids, $A_1B_1$ and $A_2B_1$, are fully-fertile (FIG. 8). The $A_2B_1$ line is naturally fertile. The $A_1B_1$ line is fertile, because the A12pot::Thi3Ri male-sterility transgene directing expression of the RNAi transcript is repressed by the activity of the A12pt::lacIn gene making repressor LacIn protein.

This combination of TDS with a ROC is a cost effective substitute for existing male-sterilty systems like barnstar/barnase. However, this male-sterile ROC system is more widely applicable and can be modified to target any essential gene, not just genes involved in thiamine biosynthesis. For example, one can make a variety of RNAi transgenes that target transcripts in other vitamin, purine, or amino acid biosynthetic pathways, or it can target the 3' end of 18S ribosomal RNA for degradation and hence effect gene silencing. Genetic configurations expressing any of these RNAi transgenes from the A12pot vector, or any pollen specific vector with appropriately placed lac operators, produce male-sterile plants. Fertility is restored by genetically crossing in pollen-specific LacIn expression.

BIBLIOGRAPHY

An, Y.-Q., McDowell, J. M., Huang, S., McKinney, E. C., Chambliss, S., and Meagher, R. B. (1996). Strong, constitutive expression of the *Arabidopsis* ACT2/ACT8 actin subclass in vegetative tissues. Plant J. 10, 107-121.

Anjaiah, V., Cornelis, P., and Koedam, N. (2003). Effect of genotype and root colonization in biological control of *fusarium* wilts in pigeonpea and chickpea by *Pseudomonas aeruginosa* PNA1. Can J Microbiol 49, 85-91.

Betz, J. L., Sasmor, H. M., Buck, F., Insley, M. Y., and Caruthers, M. H. (1986). Base substitution mutants of the lac operator: in vivo and in vitro affinities for lac repressor. Gene 50, 123-132.

Bizily, S. (2001). Genetic engineering of plants with the bacterial genes merA and merB for the phytoremediation of methylmercury contaminated sediments. In Genetics Department (Athens, Ga.: University of Georgia), pp. 145.

Bizily, S., Rugh, C. L., and Meagher, R. B. (2000). Phytodetoxification of hazardous organomercurials by genetically engineered plants. Nat Biotechnol 18, 213-217.

Bizily, S., Rugh, C. L., Summers, A. O., and Meagher, R. B. (1999). Phytoremediation of methylmercury pollution: merB expression in *Arabidopsis thaliana* confers resistance to organomercurials. Proc Natl Acad Sci USA 96, 6808-6813.

Bizily, S., Kim, T., Kandasamy, M. K., and Meagher, R. B. (2003). Subcellular targeting of methylmercury lyase enhances its specific activity for organic mercury detoxification in plants. Plant Physiol 131, 463-471.

Bouvier, F., d'Harlingue, A., Suire, C., Backhaus, R. A., and Camara, B. (1998). Dedicated roles of plastid transketolases during the early onset of isoprenoid biogenesis in pepper fruits 1. Plant Physiol. 117:1423-1431.

Brown, G., and Williamson, J. (1987). 34. Biosynthesis of folic acid, riboflavin, thiamine, and pantothenic acid. In: *Escherichia coli* and *Salmonella typhimurium*, 1, F. Neidhardt, eds (Washington, D.C.: American Society for Microbiology), pp. 521-538.

Chabregas, S. M., Luche, D. D., Farias, L. P., Ribeiro, A. F., van Sluys, M. A., Menck, C. F., and Silva-Filho, M. C. (2001). Dual targeting properties of the N-terminal signal sequence of *Arabidopsis thaliana* THI1 protein to mitochondria and chloroplasts. Plant Mol. Biol. 46:639-650.

Chang, A. K., and Duggleby, R. G. (1997). Expression, purification and characterization of *Arabidopsis thaliana* acetohydroxyacid synthase. Biochem. J. 327:161-169.

Conkling, M. A., Cheng, C.-I., Yamamoto, Y. T., and Goodman, H. M. (1990). Isolation of transcriptionally regulated root-specific genes from tobacco. Plant Physiol. 93, 1203-1211.

Dhankher, O. P., Li, Y., Rosen, B. P., Shi, J., Salt, D., Senecoff, J. F., Sashti, N. A., and Meagher, R. B. (2002). Engineering tolerance and hyperaccumulation of arsenic in plants by combining arsenate reductase and gamma-glutamylcysteine synthetase expression. Nat Biotechnol 20, 1140-1145.

Falcon, C. M., and Matthews, K. S. (2000). Operator DNA sequence variation enhances high affinity binding by hinge helix mutants of lactose repressor protein. Biochemistry 39, 11074-11083.

Fuerst, T. R., Fernandez, M. P., and Moss, B. (1989). Transfer of the inducible lac repressor/operator system from *Escherichia coli* to a vaccinia virus expression vector. Proc Natl Acad Sci USA 86, 2549-2553.

Gao, A. G., Hakimi, S. M., Mittanck, C. A., Wu, Y., Woerner, B. M., Stark, D. M., Shah, D. M., Liang, J., and Rommens, C. M. (2000). Fungal pathogen protection in potato by expression of a plant defensin peptide. Nat Biotechnol 18, 1307-1310.

Giblin-Davis, R. M., Williams, D. S., Bekal, S., Dickson, D. W., Brito, J. A., Becker, J. O., and Preston, J. F. (2003). '*Candidatus pasteuria usgae*' sp. nov., an obligate endoparasite of the phytoparasitic nematode Belonolaimus longicaudatus. Int J Syst Evol Microbiol 53, 197-200.

Goddemeier, M. L., Wulff, D., and Feix, G. (1998). Root-specific expression of a *Zea mays* gene encoding a novel glycine-rich protein, zmGRP3. Plant Mol. Biol. 36, 799-802.

Goffeau, A., Barrell, B. G., Bussey, H., Davis, R. W., Dujon, B., Feldmann, H., Galibert, F., Hoheisel, J. D., Jacq, C., Johnston, M., Louis, E. J., Mewes, H. W., Murakami, Y., Philippsen, P., Tettelin, H., and Oliver, S. G. (1996). Life with 6000 genes. Science 274:546, 563-567.

Goldfarb, D. S., Gariepy, J., Schoolnik, G., and Kornberg, R. D. (1986). Synthetic peptides as nuclear localization signals. Nature 322, 641-644.

Grana, D., Gardella, T., and Susskind, M. M. (1988). The effects of mutations in the ant promoter of phage P22 depend on context. Genetics 120, 319-327. Guerinot, M. L. (2001). Improving rice yields—ironing out the details. Nat Biotechnol 19, 417-418.

Guerinot, M. L., and Eidè, D. (1999). Zeroing in on zinc uptake in yeast and plants. Curr Opin Plant Biol 2, 244-249.

Gutteridge, R. J., Bateman, G. L., and Todd, A. D. (2003). Variation in the effects of take-all disease on grain yield and quality of winter cereals in field experiments. Pest Manag Sci 59, 215-224.

Hajdukiewicz, P., Svab, Z., and Maliga, P. (1994). The small, versatile pPZP family of *Agrobacterium* binary vectors for plant transformation. Plant Mol Biol 25, 989-994.

Halbach, S., Ballatori, N., and Clarkson, T. W. (1988). Mercury vapor uptake and hydrogen peroxide detoxification in human and mouse red blood cells. Toxicol Appl Pharmacol 96, 517-524.

Heaton, A. C. P., Rugh, C. L., Wang, N.-J., and Meagher, R. B. (1998). Phytoremediation of mercury and methylmercury polluted soils using genetically engineered plants. J. Soil Contam. 7, 497-509.

Held, B. M., Wang, H., John, I., Wurtele, E. S., and Colbert, J. T. (1993). An mRNA putatively coding for an O-methyltransferase accumulates preferentially in maize roots and is located predominantly in the region of the endodermis. Plant Physiol 102, 1001-1008.

Held, B. M., John, I., Wang, H., Moragoda, L., Tirimanne, T. S., Wurtele, E. S., and Colbert, J. T. (1997). Zrp2: a novel maize gene whose mRNA accumulates in the root cortex and mature stems. Plant Mol Biol 35, 367-375.

Hu, M. C., and Davidson, N. (1990). A combination of derepression of the lac operator-repressor system with positive induction by glucocorticoid and metal ions provides a high-level-inducible gene expression system based on the human metallothionein-IIA promoter. Mol Cell Biol 10, 6141-6151.

Iqbal, J., Afzal, J., Yaegashi, S., Ruben, E., Triwitayakorn, K., Njiti, N., Ahsan, R., Wood, J., and Lightfoot, A. (2002). A pyramid of loci for partial resistance to *Fusarium solani* f. sp. glycines maintains Myo-inositol-1-phosphate synthase expression in soybean roots. Theor Appl Genet 105, 1115-1123.

Jefferson, R. A., Kavanagh, T. A., and Bevan, M. W. (1987). GUS fusions: b-glucuronidase as a sensitive and versatile gene fusion marker in higher plants. EMBO J. 6, 3901-3907.

Kandasamy, M. K., McKinney, E. C., and Meagher, R. B. (1999). The late pollen-specific actins in angiosperms. Plant J 18, 681-691.

Kandasamy, M. K., McKinney, E. C., and Meagher, R. B. (2002). Functional non-equivalency of actin isovariants in *Arabidopsis*. Mol Biol Cell 13, 251-261.

Kandasamy, M. K., McKinney, E. C., and Meagher, R. B. (2003). Cell cycle-dependent association of *Arabidopsis* actin-related proteins AtARP4 and AtARP7 with the nucleus. Plant J 33, 939-948.

Lauter, F.-R. (1996). Root-specific expression of the LeRse-1 gene in tomato is induced by exposure of the shoot to light. Mol. Gen. Genet. 252, 751-754.

Ledoux, L., Huart, R., and Jacobs, M. (1974). DNA-mediated genetic correction of thiamineless *Arabidopsis thaliana*. Nature 249:17-21.

Lewers, K., Heinz, R., Beard, H., Marek, L., and Matthews, B. (2002). A physical map of a gene-dense region in soybean linkage group A2 near the black seed coat and Rhg (4) loci. Theor Appl Genet 104, 254-260.

Li, S. L., and Redei, G. P. (1969). Thiamine mutants of the crucifer, *Arabidopsis*. Biochem. Genet. 3:163-170.

Lievens, B., Brouwer, M., Vanachter, A. C., Levesque, C. A., Cammue, B. P., and Thomma, B. P. (2003). Design and development of a DNA array for rapid detection and identification of multiple tomato vascular wilt pathogens. FEMS Microbiol Lett 223, 113-122.

Machado, C. R., de Oliveira, R. L., Boiteux, S., Praekelt, U. M., Meacock, P. A., and Menck, C. F. (1996). Thi1, a thiamine biosynthetic gene in *Arabidopsis thaliana*, complements bacterial defects in DNA repair. Plant Mol. Biol. 31:585-593.

Machado, C. R., Praekelt, U. M., de Oliveira, R. C., Barbosa, A. C., Byrne, K. L., Meacock, P. A., and Menck, C. F. (1997). Dual role for the yeast THI4 gene in thiamine biosynthesis and DNA damage tolerance. J. Mol. Biol. 273:114-121

Meagher, R. B. (2000). Phytoremediation of toxic elemental and organic pollutants. Curr Opin Plant Biol 3, 153-162.

Meagher, R. B., and Rugh, C. L. (1996). Phytoremediation of heavy metal pollution: Ionic and methyl mercury. In OECD Biotechnology for Water Use and Conservation Workshop (Cocoyoc, Mexico: Organization for Economic Co-Operation and Development), pp. 305-321.

Meagher, R. B., and Fechheimer, M. (2002). The Cytoskeletal Proteome of *Arabidopsis*. In *Arabidopsis*, E. Meyerowitz and C. Somerville, eds (invited publication).

Nitz, I., Berkefeld, H., Puzio, P. S., and Grundler, F. M. (2001). Pyk10, a seedling and root specific gene and promoter from *Arabidopsis thaliana*. Plant Sci 161, 337-346.

Ogata, M., and Aikoh, H. (1984). Mechanism of metallic mercury oxidation in vitro by catalase and peroxidase. Biochem Pharmacol 33, 490-493.

Pfahl, M. (1979). Tight-binding repressors of the lac operon: selection system and in vitro analysis. J Bacteriol 137, 137-145.

Redei, G., and Li, S. (1969). Effects of x rays and ethyl methanesulfonate on the chlorophyll B locus in the soma and on the thiamine loci in the germline of *Arabidopsis*. Genetics 61:453-459

Rugh, C. L., Gragson, G. M., and Meagher, R. B. (1998a). Toxic mercury reduction and remediation using transgenic plants with a modified bacterial gene. Hort. Sci. 33, 12-15.

Rugh, C. L., Senecoff, J. F., Meagher, R. B., and Merkle, S. A. (1998b). Development of transgenic yellow poplar for mercury phytoremediation. Nat Biotechnol 16, 925-928.

Rugh, C. L., Wilde, D., Stack, N. M., Thompson, D. M., Summers, A. O., and Meagher, R. B. (1996). Mercuric ion reduction and resistance in transgenic *Arabidopsis thaliana* plants expressing a modified bacterial merA gene. Proc Natl Acad Sci USA 93, 3182-3187.

Sabatini, S., Heidstra, R., Wildwater, M., and Scheres, B. (2003). SCARECROW is involved in positioning the stem cell niche in the *Arabidopsis* root meristem. Genes Dev 17, 354-358.

Shirley, B. W. (1989). Analysis of the transcriptional and post-transcriptional regulation of the ribulose-1,5-bisphosphate carboxylase small subunit gene family in soybean (*Glycine max*). In Genetics (Athens, Ga.: University of Georgia), pp. 1-206.

Shirley, B. W., Berry-Lowe, S. L., Rogers, S. G., Flick, J. S., Horsch, R., Fraley, R. T., and Meagher, R. B. (1987). 5' proximal sequences of a soybean ribulose-1,5-bisphosphate carboxylase small subunit gene direct light and phytochrome controlled transcription. Nucleic Acids Res 15, 6501-6514.

Smith, T., Pitts, K., McGarvey, J. A., and Summers, A. O. (1998). Bacterial oxidation of mercury metal vapor, Hg(0). Appl Environ Microbiol 64, 1328-1332.

Suszcynsky, E. M., and Shann, J. R. (1995). Phytotoxicity and accumulation of mercury subjected to different exposure routes. Envir. Toxicol. and Chem. 14, 61-67.

Tanaka, A., Mita, S., Ohta, S., Kyozuka, J., Shimamoto, K., and Nakamura, K. (1990). Enhancement of foreign gene expression by a dicot intron in rice but not in tobacco is correlated with an increased level of mRNA and an efficient splicing of the intron. Nucleic Acids Res 18, 6767-6770.

Ulmasov, B., Capone, J., and Folk, W. (1997). Regulated expression of plant tRNA genes by the prokaryotic tet and lac repressors. Plant Mol Biol 35, 417-424.

Waldron, L. J., and Terry, N. (1975). Effect of mercury vapor on sugar beets. J. Environ. Qual. 4, 58-60.

Whitson, P. A., Olson, J. S., and Matthews, K. S. (1986). Thermodynamic analysis of the lactose repressor-operator DNA interaction. Biochemistry 25, 3852-3858.

Yamamoto, Y. T., Cheng, C. L., and Conkling, M. A. (1990). Root-specific genes from tobacco and *Arabidopsis* homologous to an evolutionarily conserved gene family of membrane channel proteins. Nucleic Acids Res 18, 7449.

Yamamoto, Y. T., Taylor, C. G., Acedo, G. N., Cheng, C. L., and Conkling, M. A. (1991). Characterization of cis-acting sequences regulating root-specific gene expression in tobacco. Plant Cell 3, 371-382.

Ye, G.-N., Stone, D., Pang, S.-Z., Creely, W., Gonzalez, K., and Hinchee, M. (1999). *Arabidopsis* ovule is the target for *Agrobacterium* in planta vacuum infiltration transformation. Plant J. 19, 249-257.

TABLE 3

Oligonucleotides

| Name | Orientation | Sequence 5'→3' | |
|---|---|---|---|
| LacIs-NcoXho | sense | TAGTAAGGAGGAACCACCTCGAGGCCATGGGT AAACCAGTAACGTTATACGAT | (SEQ ID NO:1) |
| LacIa-NLSBamHind | antisense | ATGTAAGCTTGGATCCTCAAACCTTTCTCTTCTT CTTAGGATGAACAACAGAAGACTGCCCGCTTTC CAGTCGGGAAA | (SEQ ID NO:2) |
| ACT2p-KpnS | sense | clamp GGTACCTGATCTCAAATACATTGATA | (SEQ ID NO:3) |
| Act2p-LacO1A | antisense | GCCGGAGATT CAAAACGGCT GATGAAAGTG AGGAGGACAA CGAGACAATT CAATTGTTAT CCGCTCACAA TTCCACTTAT ATAGGCGGGT TTATCTCTT | (SEQ ID NO:4) |
| Act2p-LacO2S | sense | AGCCGTTTTG AATCTCCGGC GACTTGACAG AGAAGAACAA GGATGTGGAA TTGTGAGCGG ATAACAATTT AATCCAGGAG ATTCATTCTC CGTTTTGAA | (SEQ ID NO:5) |
| ACT2p-1100A | antisense | TAGCTATAATCGAGCTAACTGAT | (SEQ ID NO:6) |
| GUS-S | sense | TAGAGTTCTA GAATAAAGGA GGAAAAACCG GTACCCCATG GGATTACGTCCTG TAGAAACCCC AA | (SEQ ID NO:7) |
| GUS-A | antisense | TTC GAT CTC GAG GAG CTC GGA TCC TCA TTG TTT GCC TCC CTG CTG CGG TT | (SEQ ID NO:8) |

TABLE 4

A12pt derived from the *Arabidoipsis thaliana* Actin ACT12 gene length; promoter cloned into SalI/PstI of ACT12term Bluescript Ks. See also SEQ ID NO:17.

```
    KpnI   ApaI    XhoI   SalI
  1 GGTACCGGGCCCCCCCTCGAGGTCGACATTTCTCTATAA ATTACTAATT

51 TTCTTGTGAA ATTTTGAATA TTTTTCAACT ATTATATTTT CACGGATTGA

101 ATATACGAAT TTTTACGGAT ATAGTGGTCA CTTTTTTGCT GTAGTTGGTG

151 ACATTTTTGG GGTGTCATAG AAGAACAAAA TTGTTAATGC ATTTATAATT

201 TTGGATTTAG TGATAATTGA AGAATTAAAA AGGTTTTATA CCTCTATCTC

251 TCTAATCATG CAAGAAAATA TTTTAAAAAG AAAAATTAAA AATAGTTCAA

301 CTGGACAACG AAATTATCCT AAAATAGTTA TTTCTTTTGA TCTAATCCTT

351 CTTCTTTTAA ACTTTTTTTT ACTTGTTTCT ACTCTACATG TTTCTTGTTA

401 TTAGGTAAAG TATTAGGCTC TTTTTTTAAA AAAAATGCTT AATCCTCTGG

KpnI
451 GTACCTCGAA AAGGGAATAA TACTCTAGTT AGATAAGTGC AGCGATCAAC

501 ATGACAAAAT GAATGAATGT TTGCTTTAAT TGGTGGCTAA AAGCTAAATA

551 CACAGAAAAG TCAAAATTCA ATCTCAAAAT CAACCCCTCT GTCTCCAATG

601 TCCCTAATCT ATACCAAAAT GTCAATTTAT TTTCTTGATC ATATATTCCA

651 CTAATTAAAA ATAAATCCTT CTCTAATGAA ATTTGTCAAG GCCTTGGAAG

701 CCTAGTTTTA AATATTAAAT GGAAACTATT TCTTCAACAA TCACACTGTT

751 ATTTAGTATT GTTGTATGTT GTTCACTACT TTCTTCATTT GTTTTGTAAG

801 AAACTATAAT AAGCAAAAAC ACATAATAAA GTCTCATGTC AAATAATGAA

851 TCTTATGCAC ATGCTTGATT ATTTTACTTG CACATATCCC TATCATCATT

901 ATCACATTTG TCAATTACCG TTATCATCAT TACTCTCATT CTTCCCAGAA
```

TABLE 4-continued

A12pt derived from the *Arabidoipsis thaliana* Actin ACT12 gene length; promoter cloned into SalI/PstI of ACT12term Bluescript Ks. See also SEQ ID NO:17.

```
 951 CTTTTTCAGC AATTTCCATA CCTCACCCAC TAAGATCTTT TACCCTTTTT

1001 CTTAATTATA GTTTGGATAG CACTCTTTTA CATAGCACTG AAATTTCGGT

1051 TGAACACATA AATTACTAGA AACTAGAAGG AAATGTTACT GAAATTTCAC

1101 TGATTGTCTA AAATTGAATA ATCTAAAGAA AATGGCCTTT TAACCTTTTT

1151 CTTAGGCCCA AATGGGCTCA TTACCACTCA TGCTTGTTCG GTGACCCGAT

1201 TCTTCCGGTA AAACAGAGCC TAAACCGTAT TTTCAGGTTA GGCTGGTGTT

1251 TTCTTAATTC TCCAACCTAA AAATAGATGG ACACGTGTCT ATAGAGGCTG

1301 AGATATTGGT CTCAATGAAG AAAACTAACG GCTCAGACCC GTGTATGAAC

1351 GATATTAAGG GCCAAAGTTG CTTCTGTTTT CCAGAAATTT TTGAAACCCA
                                            XbaI    BgIII
1401 ATTTCAGGGC ACGATTCCAC AACCTCTTTC TTTTCTTCTA GATCTACGTA

1451 AATTCATCAG GTACATGTTA TTTTTTTTGT TTATTTGATG TCAAAATTTT

1501 GATCACAAGG AGGCAAAACC AATATAAATG TAACGCTAAT GCGTTTGATT

1551 ATGGTATACG TAACGAATTA GATTTAATGG TTACATTTTA TTGTTTTAGA

1601 TTTAGTTATG AGATTGGCAT TAATTATTGG TGTTTCCTTT GAATTTGCTA
                                           NcoI    ApaI
1651 TGTTTCTTAT GTTGATGTAA TCAGCTAGAG ATTGAACCATGGGGGCCC

SphI    PstI SmaI BamHI SpeI   XbaI
1701 GCATGC CTGCAGCCCGGGGGATCCACTAGTTCTAGATCAAAAGTCA

EcoRV
1751 CCAAGTAAAA CAAGAGCGGT AAAAATTTTGA TATCAGTTT TCACCCTGA

1801 AGCCATTTGCT ATAATTACTC ACAACTTCTC TATTTGTGTT CTTTTATTCT

1851 TGTCCCTCAT TGTTCATTTT AATCTCTCTT TTGCAACAAA GCAACTTAAA

1901 AAAACAGATC AGTCATTAAC AGAATGTTAT TATTATATGT ATACATATTA

1951 GTATACACCC ATTATCTTCT TCTGAGTTTC CTCTCTGTCT CTGCTTAGTT

HindIII
2001 TTTTTCAAGC TTGGACCTCG ATTCATTTA AATCTTTTAT CATATAAGC

2051 ATAGGATTCT ATACATCGAT ATATATTTAT TTTGTTGACA CTATTCAGCAC

2101 ATGCGTATGT CTTATCTTGT TAGTATATGT AACCAAAGAC AAAGAAAAGA

2151 TGCTACAAAT TGTTTTCTCT GATGCAGAAA TTCAATCTTA AAATTGTTTT

2201 TTTTTTCAAT TGCACAAAAA ATCATGTAGT TGTAAATTT TCTAAACAAT

SacI
2251 TTTGATGATC TTTGAGCTC
```

TABLE 5

ACT12pt::LacIn. The LacI gene with an N-terminal nuclear localization signal (nls) was cloned into the NcoI and BamHI sites of the ACT12pt vector in Bluescript KS. See also SEQ ID NO:18.

```
   KpnI    ApaI     XhoI    SalI
  1 GGTACCGGGCCCCCCCTCGAGGTCGACATTTCTCTATAAAATTACTAATT

51 TTCTTGTGAA ATTTTGAATA TTTTTCAACT ATTATATTTT CACGGATTGA
```

TABLE 5-continued

ACT12pt::LacIn. The LacI gene with an N-terminal nuclear localization signal (nls) was cloned into the NcoI and BamHI sites of the ACT12pt vector in Bluescript KS. See also SEQ ID NO:18.

```
 101 ATATACGAAT TTTTACGGAT ATAGTGGTCA CTTTTTTGCT GTAGTTGGTG

151 ACATTTTTGG GGTGTCATAG AAGAACAAAA TTGTTAATGC ATTTATAATT

201 TTGGATTTAG TGATAATTGA AGAATTAAAA AGGTTTTATA CCTCTATCTC

251 TCTAATCATG CAAGAAAATA TTTTAAAAAG AAAAATTAAA AATAGTTCAA

301 CTGGACAACG AAATTATCCT AAAATAGTTA TTTCTTTTGA TCTAATCCTT

351 CTTCTTTTAA ACTTTTTTTT ACTTGTTTCT ACTCTACATG TTTCTTGTTA

401 TTAGGTAAAG TATTAGGCTC TTTTTTTAAA AAAAATGCTT AATCCTCTGG
     KpnI
 451 GTACCTCGAA AAGGGAATAA TACTCTAGTT AGATAAGTGC AGCGATCAAC

501 ATGACAAAAT GAATGAATGT TGCTTTAAT TGGTGGCTAA AAGCTAAATA

551 CACAGAAAAG TCAAAATTCA ATCTCAAAAT CAACCCCTCT GTCTCCAATG

601 TCCCTAATCT ATACCAAAAT GTCAATTTAT TTTCTTGATC ATATATTCCA

651 CTAATTAAAA ATAAATCCTT CTCTAATGAA ATTTGTCAAG GCCTTGGAAG

701 CCTAGTTTTA ATATTAAAT GGAAACTATT TCTTCAACAA TCACACTGTT

751 ATTTAGTATT GTTGTATGTT GTTCACTACT TTCTTCATTT GTTTTGTAAG

801 AAACTATAAT AAGCAAAAAC ACATAATAAA GTCTCATGTC AAATAATGAA

851 TCTTATGCAC ATGCTTGATT ATTTTACTTG CACATATCCC TATCATCATT

901 ATCACATTTG TCAATTACCG TTATCATCAT TACTCTCATT CTTCCCAGAA

951 CTTTTTCAGC AATTTCCATA CCTCACCCAC TAAGATCTTT TACCCTTTTT

1001 CTTAATTATA GTTTGGATAG CACTCTTTTA CATAGCACTG AAATTTCGGT

1051 TGAACACATA AATTACTAGA AACTAGAAGG AAATGTTACT GAAATTTCAC

1101 TGATTGTCTA AAATTGAATA ATCTAAAGAA AATGGCCTTT TAACCTTTTT

1151 CTTAGGCCCA AATGGGCTCA TTACCACTCA TGCTTGTTCG GTGACCCGAT

1201 TCTTCCGGTA AAACAGAGCC TAAACCGTAT TTTCAGGTTA GGCTGGTGTT

1251 TTCTTAATTC TCCAACCTAA AAATAGATGG ACACGTGTCT ATAGAGGCTG

1301 AGATATTGGT CTCAATGAAG AAAACTAACG GCTCAGACCC GTGTATGAAC

1351 GATATTAAGG GCCAAAGTTG CTTCTGTTTT CCAGAAATTT TGAAACCCA
                                         XbaI   BglII
1401 ATTTCAGGGC ACGATTCCAC AACCTCTTTCTTTTCTTCTA GATCTACGTA

1451 AATTCATCAG GTACATGTTA TTTTTTTTGT TTATTTGATG TCAAAATTTT

1501 GATCACAAGG AGGCAAAACC AATATAAATG TAACGCTAAT GCGTTTGATT

1551 ATGGTATACG TAACGAATTA GATTTAATGG TTACATTTTA TTGTTTTAGA

1601 TTTAGTTATG AGATTGGCAT TAATTATTGG TGTTTCCTTT GAATTTGCTA
                                NcoI
1651 TGTTTCTTAT GTTGATGTAA TCAGCTAGAG ATTGAACCATGGGTAAACCA

1701 GTAACGTTAT ACGATGTCGC AGAGTATGCC GGTGTCTCTT ATCAGACCGT

1751 TTCCCGCGTG GTGAACCAGG CCAGCCACGT TTCTGCGAAA ACGCGGGAAA

1801 AAGTGGAAGC GGCGATGGCG GAGCTGAATT ACATTCCCAA CCGCGTGGCA
```

TABLE 5-continued

ACT12pt::LacIn. The LacI gene with an N-terminal nuclear localization signal (nls) was cloned into the NcoI and BamHI sites of the ACT12pt vector in Bluescript KS. See also SEQ ID NO:18.

```
1851 CAACAACTGG CGGGCAAACA GTCGTTGCTG ATTGGCGTTG CCACCTCCAG

1901 TCTGGCCCTG CACGCGCCGT CGCAAATTGT CGCGGCGATT AAATCTCGCG

1951 CCGATCAACT GGGTGCCAGC GTGGTGGTGT CGATGGTAGA ACGAAGCGGC

2001 GTCGAAGCCT GTAAAGCGGC GGTGCACAAT CTTCTCGCGC AACGCGTCAG

2051 TGGGCTGATC ATTAACTATC CGCTGGATGA CCAGGATGCC ATTGCTGTGG

2101 AAGCTGCCTG CACTAATGTT CCGGCGTTAT TTCTTGATGT CTCTGACCAG

2151 ACACCCATCA ACAGTATTAT TTTCTCCCAT GAAGACGGTA CGCGACTGGG

ApaI
2201 CGTGGAGCAT CTGGTCGCAT GGGTCACCA GCAAATCGCG CTGTTAGCGG

2251 GCCCATTAAG TTCTGTCTCG GCGCGTCTGC GTCTGGCTGG CTGGCATAAA

2301 TATCTCACTC GCAATCAAAT TCAGCCGATA GCGGAACGGG AAGGCGACTG

2351 GAGTGCCATG TCCGGTTTTC AACAAACCAT GCAAATGCTG AATGAGGGCA

2401 TCGTTCCCAC TGCGATGCTG GTTGCCAACG ATCAGATGGC GCTGGGCGCA

EcoRV
2451 ATGCGCGCCA TTACCGAGTC CGGGCTGCGC GTTGGTGCGG ATATCTCGGT

2501 AGTGGGATAC GACGATACCG AAGACAGCTC ATGTTATATC CGCCGTTAA

2551 CCACCATCAA ACAGGATTTT CGCCTGCTGG GGCAAACCAG CGTGGACCGC

2601 TTGCTGCAAC TCTCTCAGGG CCAGGCGGTG AAGGGCAATC AGCTGTTGCC

2651 CGTCTCACTG GTGAAAAGAA AAACCACCCT GGCGCCCAAT ACGCAAACCG

2701 CCTCTCCCCG CGCGTTGGCC GATTCATTAA TGCAGCTGGC ACGACAGGTT

2751 TCCCGACTGG AAAGCGGGCA GTCTTCTGTT GTTCATCCTA AGAAGAAGAG

BamHI SpeI  XbaI
2801 AAAGGTTTGAGGATCCACTAGTTCTAGATCAAAAGTCAC AAGTAAAACA

EcoRV
2851 AGAGCGGTAA AAATTTTGATATCAGTTTTT CACCCTGAAG CCATTTGCTA

2901 TAATTACTCA CAACTTCTCT ATTTGTGTTC TTTTATTCTT GTCCCTCATT

2951 GTTCATTTTA ATCTCTCTTT TGCAACAAAG CAACTTAAAA AAACAGATCA

3001 GTCATTAACA GAATGTTATT ATTATATGTA TACATATTAG TATACACCCA

HindIII
3051 TTATCTTCTT CTGAGTTTCC TCTCTGTCTC TGCTTAGTTT TTTTCAAGCT

3101 TGGACCTCGA TTTCATTTAA ATCTTTTATC ATATAAGCAT AGGATTCTAT

3151 ACATCGATAT ATATTTATTT TGTTGACACT ATTCAGCACA TGCGTATGTC

3201 TTATCTTGTT AGTATATGTA ACCAAAGACA AGAAAAGAT GCTACAAATT

3251 GTTTTCTCTG ATGCAGAAAT TCAATCTTAA AATTGTTTTT TTTTTCAATT

3301 GCACAAAAAA TCATGTAGTT TGTAAATTTT CTAAACAATT TTGATGATCT

SacI
3351 TTGAGCTC
```

TABLE 6

Sequence of ACT12pot vector clone #5 in Bluescript,.
See also SEQ ID NO:19.
put together with t3,t7,1180s,seqnseqs2
3 base changes, 2 in leader intron 1469 & 1480, 1 in term
2022 which is 292 bp past stop
292 bp past stop
2 copies LacO at 1359 & 1411
Act12pot#5.seq

```
     KpnI   ApaIXhoI  SalI
   1 GGTACCGGGC CCCCCCTCGA GGTCGAC ATT TCTCTATAAA ATTACTAATT

51 TTCTTGTGAA ATTTTGAATA TTTTTCAACT ATTATATTTT CACGGATTGA

101 ATATACGAAT TTTTACGGAT ATaGTGGTCA CTTTTTTGCT GTAGTTGGTG

151 ACATTTTTGG GGTGTCATAG AAGAACAAAA TTGTTAATGC ATTTATAATT

201 TTGGATTTAG TGATAATTGA AGAATTAAAA AGGTTTTATA CCTCTATCTC

251 TCTAATCATG CAAGAAAATA TTTTAAAAAG AAAAATTAAA AATAGTTCAA

301 CTGGACAACG AAATTATCCT AAAATAGTTA TTTCTTTTGA TCTAATCCTT

351 CTTCTTTTAA ACTTTTTTTT ACTTGTTTCT ACTCTACATG TTTCTTGTTA

401 TTAGGTAAAG TATTAGGCTC TTTTTTTAAA AAAATGCTT AATCCTCTGG

KpnI
 451 GTACCTCGAA AAGGGAATAA TACTCTAGTT AGATAAGTGC AGCGATCAAC

501 ATGACAAAAT GAATGAATGT TGCTTTAAT TGGTGGCTAA AAGCTAAATA

551 CACAGAAAAG TCAAAATTCA ATCTCAAAAT CAACCCCTCT GTCTCCAATG

601 TCCCTAATCT ATACCAAAAT GTCAATTTAT TTTCTTGATC ATATATTCCA

651 CTAATTAAAA ATAAATCCTT CTCTAATGAA ATTTGTCAAG GCCTTGGAAG

701 CCTAGTTTTA AATATTAAAT GGAAACTATT TCTTCAACAA TCACACTGTT

751 ATTTAGTATT GTTGTATGTT GTTCACTACT TTCTTCATTT GTTTTGTAAG

801 AAACTATAAT AAGCAAAAAC ACATAATAAA GTCTCATGTC AAATAATGAA

851 TCTTATGCAC ATGCTTGATT ATTTTACTTG CACATATCCC TATCATCATT

901 ATCACATTTG TCAATTACCG TTATCATCAT TACTCTCATT CTTCCCAGAA

951 CTTTTTCAGC AATTTCCATA CCTCACCCAC TAAGATCTTT TACCCTTTTT

1001 CTTAATTATA GTTGGATAG CACTCTTTTA CATAGCACTG AAATTTCGGT

1051 TAAACACATA AATTACTAGA AACTAGAAGG AAATGTTACT GAAATTTCAC

1101 TGATTGTCTA AAATTGAATA ATCTAAAGAA AATGGCCTTT TAACCTTTTT

1151 CTTAGGCCCA AATGGGCTCA TTACCACTCA TGCTTGTTCG GTGACCCGAT

1201 TCTTCCGGTA AAACAGAGCC TAAACCGTAT TTTCAGGTTA GGCTGGTGTT

1251 TTCTTAATTC TCCAACCTAA AAATAGATGG ACACGTGTCT ATAGAGGCTG

1301 AGATATTGGT CTCAATGAAG AAAACTAACG GCTCAGACCC GTGTATGAAC

LacO
1351 GATATTAAGT GGAATTGTGA GCGGATAACA ATTGAAATTT TGAAACCCA

LacO                    XbaI    BgIII
1401 ATTTCAGGGC AGTGGAATTG TGAGCGGATA ACAATTTCTA GATCTACGTA

1451 AATTCATCAG GTACATGTCA TTTTTTTTGC TTATTTGATG TCAAAATTTT

1501 GATCACAAGG AGGCAAAACC AATATAAATG TAACGCTAAT GCGTTTGATT

1551 ATGGTATACG TAACGAATTA GATTTAATGG TTACATTTTA TTGTTTTAGA
```

TABLE 6-continued

Sequence of ACT12pot vector clone #5 in Bluescript,.
See also SEQ ID NO:19.
put together with t3,t7,1180s,seqnseqs2
3 base changes, 2 in leader intron 1469 & 1480, 1 in term
2022 which is 292 bp past stop
292 bp past stop
2 copies LacO at 1359 & 1411
Act12pot#5.seq

```
1601 TTTAGTTATG AGATTGGCAT TAATTATTGG TGTTTCCTTT GAATTTGCTA

NcoI  ApaI
1651 TGTTTCTTAT GTTGATGTAA TCAGCTAGAG ATTGAACCATGGGGGCCCGC

SphI PstI SmaI BamHI SpeI XbaI
1701 ATGCCTGCAGCCCGGGGATCCACTAGTTCTAGATCAAAAGTCACCAAGT

EcoRV
1751 AAAACAAGAG CGGTAAAAAT TTTGATATCA GTTTTTCACC CTGAAGCCAT

1801 TTGCTATAAT TACTCACAAC TTCTCTATTT GTGTTCTTTT ATTCTTGTCC

1851 CTCATTGTTC ATTTTAATCT CTCTTTTGCA ACAAAGCAAC TTAAAAAAAC

1901 AGATCAGTCA TTAACAGAAT GTTATTATTA TATGTATACA TATTAGTATA

1951 CACCCATTAT CTTCTTCTGA GTTTCCTCTC TGTCTCTGCT TAGTTTTTTT

HindIII
2001 CAAGCTTGGA CCTCGATTTC ACTTAAATCT TTTATCATAT AAGCACAGGA

2051 TTCTATACAT CGATATATAT TTATTTTGTT GACACTATTC AGCACATGCG

2101 TATGTCTTAT CTTGTTAGTA TATGTAACCA AAGACAAAGA AAAGATGCTA

2151 CAAATTGTTT TCTCTGATGC AGAAATTCAA TCTTAAAATT GTTTTTTTT

2201 TCAATTGCAC AAAAAATCAT TTGTAAATTT CTAAACAAT

SacI
2251 TTTGATGATC TTTGAGCTC
```

TABLE 7

A12pot::GUS in Bluescript KS. See also SEQ ID NO:20.
Gus is cloned into the NcoI and BamHI sites
of the ACT12 derived vector A12pot

```
    KpnI    ApaIXhoI  SalI
   1 GGTACCGGGC CCCCCCTCGA GGTCGACATT TCTCTATAAA ATTACTAATT

51 TTCTTGTGAA ATTTTGAATA TTTTTCAACT ATTATATTTT CACGGATTGA

101 ATATACGAAT TTTTACGGAT ATAGTGGTCA CTTTTTTGCT GTAGTTGGTG

151 ACATTTTTGG GGTGTCATAG AAGAACAAAA TTGTTAATGC ATTTATAATT

201 TTGGATTTAG TGATAATTGA AGAATTAAAA AGGTTTTATA CCTCTATCTC

251 TCTAATCATG CAAGAAAATA TTTTAAAAAG AAAAATTAAA AATAGTTCAA

301 CTGGACAACG AAATTATCCT AAAATAGTTA TTTCTTTTGA TCTAATCCTT

351 CTTCTTTTAA ACTTTTTTTT ACTTGTTTCT ACTCTACATG TTTCTTGTTA

401 TTAGGTAAAG TATTAGGCTC TTTTTTTAAA AAAAATGCTT AATCCTCTGG

KpnI
 451 GTACCTCGAA AAGGGAATAA TACTCTAGTT AGATAAGTGC AGCGATCAAC

501 ATGACAAAAT GAATGAATGT TTGCTTTAAT TGGTGGCTAA AAGCTAAATA

551 CACAGAAAAG TCAAAATTCA ATCTCAAAAT CAACCCCTCT GTCTCCAATG

601 TCCCTAATCT ATACCAAAAT GTCAATTTAT TTTCTTGATC ATATATTCCA
```

TABLE 7-continued

A12pot::GUS in Bluescript KS. See also SEQ ID NO:20.
Gus is cloned into the NcoI and BamHI sites
of the ACT12 derived vector A12pot

```
 651 CTAATTAAAA ATAAATCCTT CTCTAATGAA ATTTGTCAAG GCCTTGGAAG
 701 CCTAGTTTTA AATATTAAAT GGAAACTATT TCTTCAACAA TCACACTGTT
 751 ATTTAGTATT GTTGTATGTT GTTCACTACT TTCTTCATTT GTTTTGTAAG
 801 AAACTATAAT AAGCAAAAAC ACATAATAAA GTCTCATGTC AAATAATGAA
 851 TCTTATGCAC ATGCTTGATT ATTTTACTTG CACATATCCC TATCATCATT
 901 ATCACATTTG TCAATTACCG TTATCATCAT TACTCTCATT CTTCCCAGAA
 951 CTTTTTCAGC AATTTCCATA CCTCACCCAC TAAGATCTTT TACCCTTTTT
1001 CTTAATTATA GTTTGGATAG CACTCTTTTA CATAGCACTG AAATTTCGGT
1051 TGAACACATA AATTACTAGA AACTAGAAGG AAATGTTACT GAAATTTCAC
1101 TGATTGTCTA AAATTGAATA ATCTAAAGAA AATGGCCTTT TAACCTTTTT
1151 CTTAGGCCCA AATGGGCTCA TTACCACTCA TGCTTGTTCG GTGACCCGAT
1201 TCTTCCGGTA AAACAGAGCC TAAACCGTAT TTTCAGGTTA GGCTGGTGTT
1251 TTCTTAATTC TCCAACCTAA AAATAGATGG ACACGTGTCT ATAGAGGCTG
1301 AGATATTGGT CTCAATGAAG AAAACTAACG GCTCAGACCC GTGTATGAAC
                 LacO
1351 GATATTAAGT GGAATTGTGA GCGGATAACA ATTGAAATTT TGAAACCCA
                 LacO                XbaI    BglII
1401 ATTTCAGGGC AGTGGAATTG TGAGCGGATA ACAATTTCTA GATCTACGTA
1451 AATTCATCAG GTACATGTCA TTTTTTTTGC TTATTTGATG TCAAAATTTT
1501 GATCACAAGG AGGCAAAACC AATATAAATG TAACGCTAAT GCGTTTGATT
1551 ATGGTATACG TAACGAATTA GATTTAATGG TTACATTTTA TTGTTTTAGA
1601 TTTAGTTATG AGATTGGCAT TAATTATTGG TGTTTCCTTT GAATTTGCTA
                                             NcoI
1651 TGTTTCTTAT GTTGATGTAA TCAGCTAGAG ATTGAACCAT GGGATTACGT
1701 CCTGTAGAAA CCCCAACCCG TGAAATCAAA AACTCGACG GCCTGTGGGC
1751 ATTCAGTCTG GATCGCGAAA ACTGTGGAAT TGATCAGCGT TGGTGGGAAA
1801 GCGCGTTACA AGAAAGCCGG GCAATTGCTG TGCCAGGCAG TTTTAACGAT
1851 CAGTTCGCCG ATGCAGATAT TCGTAATTAT GCGGGCAACG TCTGGTATCA
1901 GCGCGAAGTC TTTATACCGA AAGGTTGGGC AGGCCAGCGT ATCGTGCTGC
1951 GTTTCGATGC GGTCACTCAT TACGGCAAAG TGTGGGTCAA TAATCAGGAA
2001 GTGATGGAGC ATCAGGGCGG CTATACGCCA TTTGAAGCCG ATGTCACGCC
2051 GTATGTTATT GCCGGGAAAA GTGTACGTAT CACCGTTTGT GTGAACAACG
2101 AACTGAACTG GCAGACTATC CCGCCGGGAA TGGTGATTAC CGACGAAAAC
2151 GGCAAGAAAA AGCAGTCTTA CTTCCATGAT TTCTTTAACT ATGCCGGAAT
                                       EcoRV
2201 CCATCGCAGC GTAATGCTCT ACACCACGCC GAACACCTGG GTGGACGATA
2251 TCACCGTGGT GACGCATGTC GCGCAAGACT GTAACCACGC GTCTGTTGAC
2301 TGGCAGGTGG TGGCCAATGG TGATGTCAGC GTTGAACTGC GTGATGCGGA
```

TABLE 7-continued

A12pot::GUS in Bluescript KS. See also SEQ ID NO:20.
Gus is cloned into the NcoI and BamHI sites
of the ACT12 derived vector A12pot

```
2351 TCAACAGGTG GTTGCAACTG GACAAGGCAC TAGCGGGACT TTGCAAGTGG

2401 TGAATCCGCA CCTCTGGCAA CCGGGTGAAG GTTATCTCTA TGAACTGTGC

EcoRV
2451 GTCACAGCCA AAAGCCAGAC AGAGTGTGAT ATCTACCCGC TTCGCGTCGG

2501 CATCCGGTCA GTGGCAGTGA AGGGCGAACA GTTCCTGATT AACCACAAAC

2551 CGTTCTACTT TACTGGCTTT GGTCGTCATG AAGATGCGGA CTTGCGTGGC

2601 AAAGGATTCG ATAACGTGCT GATGGTGCAC GACCACGCAT TAATGGACTG

2651 GATTGGGGCC AACTCCTACC GTACCTCGCA TTACCCTTAC GCTGAAGAGA

2701 TGCTCGACTG GGCAGATGAA CATGGCATCG TGGTGATTGA TGAAACTGCT

2751 GCTGTCGGCT TTAACCTCTC TTTAGGCATT GGTTTCGAAG CGGGCAACAA

2801 GCCGAAAGAA CTGTACAGCG AAGAGGCAGT CAACGGGGAA ACTCAGCAAG

2851 CGCACTTACA GGCGATTAAA GAGCTGATAG CGCGTGACAA AAACCACCCA

2901 AGCGTGGTGA TGTGGAGTAT TGCCAACGAA CCGGATACCC GTCCGCAAGG

2951 TGCACGGGAA TATTTCGCGC CACTGGCGGA AGCAACGCGT AAACTCGACC

3001 CGACGCGTCC GATCACCTGC GTCAATGTAA TGTTCTGCGA CGCTCACACC

3051 GATACCATCA GCGATCTCTT TGATGTGCTG TGCCTGAACC GTTATTACGG

3101 ATGGTATGTC CAAAGCGGCG ATTTGGAAAC GGCAGAGAAG GTACTGGAAA

3151 AGAACTTCT GGCCTGGCAG GAGAAACTGC ATCAGCCGAT TATCATCACC

3201 GAATACGGCG TGGATACGTT AGCCGGGCTG CACTCAATGT ACACCGACAT

3251 GTGGAGTGAA GAGTATCAGT GTGCATGGCT GGATATGTAT CACCGCGTCT

3301 TTGATCGCGT CAGCGCCGTC GTCGGTGAAC AGGTATGGAA TTTCGCCGAT

3351 TTTGCGACCT CGCAAGGCAT ATTGCGCGTT GGCGGTAACA AGAAAGGGAT

3401 CTTCACTCGC GACCGCAAAC CGAAGTCGGC GGCTTTTCTG CTGCAAAAAC

3451 GCTGGACTGG CATGAACTTC GGTGAAAAAC CGCAGCAGGG AGGCAAACAA

BamHI SpeI XbaI
3501 TGAGGATCCACTAGTTCTAGATCAAAAGTCACCAAGTAAAACAAGAGCGG

EcoRV
3551 TAAAAATTTT GATATCAGTT TTTCACCCTG AAGCCATTTG CTATAATTAC

3601 TCACAACTTC TCTATTTGTG TTCTTTTATT CTTGTCCCTC ATTGTTCATT

3651 TTAATCTCTC TTTTGCAACA AAGCAACTTA AAAAAACAGA TCAGTCATTA

3701 ACAGAATGTT ATTATTATAT GTATACATAT TAGTATACAC CCATTATCTT

HindIII
3751 CTTCTGAGTT TCCTCTCTGT CTCTGCTTAG TTTTTTTCAA GCTTGGACCT

3801 CGATTTCATT TAAATCTTTT ATCATATAAG CATAGGATTC TATACATCGA

3851 TATATATTTA TTTTGTTGAC ACTATTCAGC ACATGCGTAT GTCTTATCTT

3901 GTTAGTATAT GTAACCAAAG ACAAAGAAAA GATGCTACAA ATTGTTTTCT

3951 CTGATGCAGA AATTCAATCT TAAAATTGTT TTTTTTTCA ATTGCACAAA

SacI
4001 AAATCATGTA GTTTGTAAAT TTTCTAAACA ATTTTGATGA TCTTTGAGCT

4051 C
```

TABLE 8

*Arabidopsis* actin 11 promoter terminator sequence.
See also SEQ ID NO:23.

```
   1 gagctcgaat tctgttgtag aatacaacac attaagcgca attagcagaa
  51 acagtctctt catctgccga tttccacttg tcactactcc aaaaacctcc
 101 caaaccattt ccaaaacaga cacttttgcc atgtctacat ctttcccttc
 151 cccgaaaaac atcacttc catcaacgga gtaaatatcc ggcggcatat
 201 cgatgctcga gaccgtccta tcgagaaaag gcttagccgc ttccgtgacc
 251 gccggcgttc gtggaccgtg agattgctga acgagcgag aataagcaag
 301 cctccgatca ttagcagcat atccgacatc gctgctccga tcatcaggga
 351 gctcgttatc gcctcgagga ttaaaggaaa tggatctctc cattttcttc
 401 tttgatctta aagttccaac ttcggcaaat actaaaatca acagtcagtc
 451 gtacaaagaa actctgctta tacagtaaag tcaatgggcc actgttctaa
 501 gcccatatat aattttagaa gcccatagaa tacaaaagag tcaagaagca
 551 ttgaccgcac aagaaaaaaa caattgttaa aaagggttgg ttagtgtgta
 601 tgtatatatg aaatgcaaca acattatac agcccattaa atatggttgt
 651 tataggtaga tgtccccatt aaggaacttt atccagccca ttaaattact
 701 ttacagagta aagagagag agaagattta cagttacgtt accaaatttt
 751 cgaaatgatt taattagtaa taaataaata attaaatgtc agttactctc
 801 tttagaaagc taaataagac agctgtttcc accaacaacg tgactggtcg
 851 tggggtcctc cttcgttcaa agtgatattc agaaatcaac ggctgagatc
 901 ttctccatca atatttatta cgggcctatt ccttcctttt ttaaacttca
 951 attctccggc tcacattctc ttcttcattc gctccgtttc tctctcaaaa
1001 actacacacc cgtaccacac caccaccctc ctcgtttcct cagagatccc
1051 ctctctaact tctaaggtaa tcacatttcc ataacgttcc atcgtcattg
1101 attcttcatt agtatgcgtt tatgaagctt tttcaattta attctctttg
1151 gtagatctta agattcctct gtttcttgca aaataaaggg ttcaattatg
1201 ctaatatttt ttatatcaat tttgacagga tatagaccat ggtctagaac
1251 tagtggatcc cccgggctgc aggattaagc tcaaatcaaa gtgatgaatg
1301 attgttctgt attggtaaag ccttttgttc atcgactttg ttgcaaaata
1351 ttcttttgtt ttctatgttt cttcaccact acattacatt tctttcttgt
1401 tgttatcctc ttttggtgtt tctgctatta atcgaaaaag aaattttctt
1451 ttcttagttt ctttttctc ctcttcttaa ttctgtgaag ataaaaaga
1501 aggatgaaac cagtggccag tgggcattgg atttggcttt ttattttagg
1551 caaaagacaa gcttggtacc caattc
```

TABLE 9

*Arabidopsis* phosphomethylpyrimidine kinase (AtThi2) gene and protein
sequence
AT1G22940.1. See also SEQ ID NO:24 (DNA) and SEQ ID NO:27 (protein).

```
  1  accaaaccaaaccactcggtaaacttgtatagcctcttgtatatattatgatatatca      60
 61  ataataattacacgtgtaatgtaagatgcattttgatttgaagatgcattatgctgattt    120
```

TABLE 9-continued

*Arabidopsis* phosphomethylpyrimidine kinase (AtThi2) gene and protein sequence
AT1G22940.1. See also SEQ ID NO:24 (DNA) and SEQ ID NO:27 (protein).

```
121  gtaaaacataaacggctttggtccctttttagtgtgtccgaatgaataaggtgttcaaaa   180
181  tagcgtgtgatttgtaatttgtaatttgtaattagtctgaaacgttgtatatatgaatat   240
241  tcttcaattatataaaagcttgctttcaaatatatcaatttatctatcttttgattatat   300
301  tgtcccttttcgtggaccacaagtattaacttatctcatacaaataattcgtgcttaag   360
361  tttggtgttaaaattattgaaaattgatttacattgaattttttcgcggtaattgataa   420
421  ttcatgaaaatcgatgaaatttactaattttatttcacattaaagtcaataaaatgggaa   480
481  aatatttgatgagaataaaataaaataaaataaagagaagggacgagaaATGAATAGCTT   540
```

Boxed targeting sequence removed for bacterial expression and to eliminate
a unwanted restriction site Gly codon added to create NcoI site

```
541  AGGAGGAATTAGGAGTTGGCCGGCGAATTGGAGAAGTACGACGGCGTCAATGGGAACGAC   600
                                                     M  G  T  T
```

A→T To remove unwanted KpnI site

```
601  GACGGAGAGCGTTAGAAAGGTTCCGCAAGTTTTAACAGTGGCGGGATCAGATTCCGGCGC   660
      T  E  S  V  R  K  V  P  Q  V  L  T  V  A  G  S  D  S  G  A

661  CGGAGCTGGAATTCAAGCCGACCTTAAAGTCTGCGCAGCTCGTGGTGTGTATTGCGCTTC   720
      G  A  G  I  Q  A  D  L  K  V  C  A  A  R  G  V  Y  C  A  S

721  CGTCATAACCGCAGTCACTGCTCAGAACACTCGAGGAGTTCAATCTGTTCATCTTCTTCC   780
      V  I  T  A  V  T  A  Q  N  T  R  G  V  Q  S  V  H  L  L  P

781  TCCGGAATTTATCTCTGAACAGCTCAAATCCGTCCTCTCTGACTTCGAATTCGACGTCGT   840
      P  E  F  I  S  E  Q  L  K  S  V  L  S  D  F  E  F  D  V  V

841  GAAGACTGGGATGCTTCCTTCTACTGAGATCGTTGAGGTTCTTCTTCAAAATCTATCAGA   900
      K  T  G  M  L  P  S  T  E  I  V  E  V  L  L  Q  N  L  S  D

901  TTTTCCAGTTCGTGGTAGAGATTACCTCGCTTTGTTCTCTTTGGTTGTTGATCCTGTGAT   960
      F  P  V  R  G  R  D  Y  L  A  L  F  S  L  V  V  D  P  V  N

961  GGTATCTACTAGTGGTCACGTTTTGGCTGGTTCTTCTATTCTCTCTATCTTTAGAGAGAG   1020
      V  S  T  S  G  H  V  L  A  G  S  S  I  L  S  I  F  R  E  R

1021 ATTACTACCAATTGCTGACATAATTACCCCAAATGTGAAAGAGGCTTCTGCTTTACTTGA   1080
      L  L  P  I  A  D  I  I  T  P  N  V  K  E  A  S  A  L  L  D

1081 TGGTTTTCGGATTGAGACTGTTGCAGAAATGCGGTCTGCAGCAAAGTCGTTGCATGAAAT   1140
      G  F  R  I  E  T  V  A  E  M  R  S  A  A  K  S  L  H  E  M

1141 GGGTCCTAGATTCGTACTTGTTAAAGGTGGTGATCTTCCTGACTCATCAGATTCAGTAGA   1200
      G  P  R  F  V  L  V  K  G  G  D  L  P  D  S  S  D  S  V  D

1201 TGTTTACTTTGATGGCAAGGAGTTTCATGAACTCCGTTCTCCTCGCATAGCTACAAGAAA   1260
      V  Y  F  D  G  K  E  F  H  E  L  R  S  P  R  I  A  T  R  N

1261 TACTCATGGGACTGGTTGCACTTTGGCTTCCTGTATTGCAGCTGAGCTTGCAAAAGGCTC   1320
      T  H  G  T  G  C  T  L  A  S  C  I  A  A  E  L  A  K  G  S

1321 TTCCATGCTCTCAGCCGTCAAGGTGGCTAAACGCTTTGTCGATAATGCCCTAGATTACAG   1380
      S  M  L  S  A  V  K  V  A  K  R  F  V  D  N  A  L  D  Y  S

1381 CAAAGATATTGTCATTGGCAGTGGGATGCAAGGACCTTTTGACCATTTTTTTGGTCTTAA   1440
      K  D  I  V  I  G  S  M  Q  G  P  F  D  H  F  F  G  L  K

1441 GAAGGATCCTCAAAGTTCTCGATGCAGCATATTCAATCCAGATGACCTGTTTCTATATGC   1500
      K  D  P  Q  S  S  R  C  S  I  F  N  P  D  D  L  F  L  Y  A

1501 TGTTACAGATTCTAGAATGAACAAAAAATGGAACCGTTCCATTGTGGATGCCTTGAAAGC   1560
      V  T  D  S  R  M  N  K  K  W  N  R  S  I  V  D  A  L  K  A

1561 TGCTATAGAGGGAGGGGCCACCATCATACAACTGAGGTTTGATCATTTTCTTGAAGAAGC   1620
      A  I  E  G  G  A  T  I  I  Q  L  R  F  D  H  F  L  E  E  A
```

TABLE 9-continued

Arabidopsis phosphomethylpyrimidine kinase (AtThi2) gene and protein sequence
AT1G22940.1. See also SEQ ID NO:24 (DNA) and SEQ ID NO:27 (protein).

```
1621 AAAAGCATGCATTGATATATGCCGGTCCCATGGAGTTAGTTTGCTGATAAACGACAGGAT   1680
      K  A  C  I  D  I  C  R  S  H  G  V  S  L  L  I  N  D  R  I

1681 CGACATTGCCCTTGCTTGTGATGCTGATGGAGTCCATGTTGGTCAATCCGACATGCCGGT   1740
      D  I  A  L  A  C  D  A  D  G  V  H  V  G  Q  S  D  M  P  V

1741 TGATCTAGTTCGGTCTCTTCTTGGCCCGGACAAGATCATAGGGGTCTCATGTAAGACACC   1800
      D  L  V  R  S  L  L  G  P  D  K  I  I  G  V  S  C  K  T  P

1801 AGAACAAGCTCATCAAGCATGGAAAGATGGTGCGGACTACATTGGGTCAGGAGGAGTTTT   1860
      E  Q  A  H  Q  A  W  K  D  G  A  D  Y  I  G  S  G  G  V  F

1861 TCCAACGAACACTAAGGCCAACAATCGTACCATAGGACTTGATGGGCTAAAAGAAGTATG   1920
      P  T  N  T  K  A  N  N  R  T  I  G  L  D  G  L  K  E  V  C

1921 TGAAGCATCAAAATTACCGGTTGTTGCAATCGGAGGCATAGGGATCTCAAATGCTGGGTC   1980
      E  A  S  K  L  P  V  V  A  I  G  G  I  G  I  S  N  A  G  S

1981 TGTTATGCAGATCGATGCACCGAACCTAAAAGGTGTAGCAGTTGTGTCAGCTTTGTTCGA   2040
      V  M  Q  I  D  A  P  N  L  K  G  V  A  V  V  S  A  L  F  D

2041 CCAAGATTGTGTTTTGACTCAAGCTAAGAAGTTGCATAAAACGCTTAAAGAGAGCAAAAG   2100
      Q  D  C  V  L  T  Q  A  K  K  L  H  K  T  L  K  E  S  K  R
```

Boxed region used in Thi2-Ri construct

```
2101 GGGAATTTGAaccaaaaggtgttttagttttgttttaggtgcttacaaaatgttgtaaa    2160
      G  I
```

```
2161 cctttacttctttacttgatgtatttttttttttttgagaaagccagaaaagataa       2220
```

2221 Lower case letters part of 3'UTR, upper case is CDS             2280
```
     atagtaatgattgctacaaacattttacttccaaaaacttccaacattctcaaattctc
```

```
2281 caagagataacatttgtgtatttcatttgccttcactcctctaagaaatttattgttaca  2340

2341 ggcagcaatctgaaaaatggaacaaaatttacctttgacaaaggtatctaatgcttgctt  2400

2401 acaaacaaacgatttaacttgcctctctatatacacatagccactggaatggtacaaaga  2460

2461 agatgaggtatttgacatattcttgttttgt                                2492
```

Capital letters are coding region
Small letters are UTRs
Boxed area with thin line is deleted region
Boxed area with thick line is 3'UTR used for RNAi construction
Boxed area with dotted line is inserted region
Boxed area with black background and white letters are start/stop codon
Outlined letter is mutated site (A → T)

TABLE 10

Arabidopsis hydoxyethylthiazole kinase (AtThi3) DNA and protein sequence. See also SEQ ID NO:25 (DNA) and SEQ ID NO:28 (protein)

```
  1 tcggatgatcctcaccgcactttcaatagagtaaatagttgtccaagacacgaagaagat   60

61 aacggtactttatgcttctgtatctttagagagagttccacttctacattgtaacctgtg  120

121 actttgagagtgtttgttccattgttgttgtagaaaaaccatctcaaagctgagaaatga  180
```

TABLE 10-continued

*Arabidopsis* hydoxyethylthiazole kinase (AtThi3) DNA and protein sequence. See also SEQ ID NO:25 (DNA) and SEQ ID NO:28 (protein)

```
 181   aacgactcggttcattggttgaagtctaaaccggtatataaaatcccggttttaatctaatc   240

241   tagaccaaaccgtgtttcttatatatatttgaatccgtgatttacgcacgactggttaaa    300

T -change to eliminate SacI
site
 301   gcaga ATG GAATCAAAATCAGAACAAAACGAGTGGAGCTCCGGCGTGTGGCTCACTTAA    360
             M   E  S  K  S  E  Q  N  E  W  S  S  G  V  W  A  H  L  T 361   CCGCCGTACGGCAACAATCGCCGCTTGTTCAGTGCATCACCAACTTCGTCTCGATGGATC    420
        A  V  R  Q  Q  S  P  L  V  Q  C  I  T  N  F  V  S  M  D  L 421   TCGTTGCCAACACGCTTTTATCCGCCGGTGCATCTCCAGCGATGGTCCATTCCGTCGTTG    480
        V  A  N  T  L  L  S  A  G  A  S  P  A  M  V  H  S  V  V  E 481   AGATTCCTGATTTCACTCCTCATATTCACGCGCTCTGCGTCAACGTCGGAACACTTACAC    540
        I  P  D  F  T  P  H  I  H  A  L  C  V  N  V  G  T  L  T  P 541   CTGACTGGCTTCCGTCAATGAAAGCTGCCGCTGAACTCGCTTCTCAGCTCCGAAAGCCTT    600
        D  W  L  P  S  M  K  A  A  A  E  L  A  S  Q  L  R  K  P  W 601   GGGTTCTTGATCCCGCCGCCGTGAGTTGCTCCGGATTCCGATTAAAAGCGTGTTTGGAGC    660
        V  L  D  P  A  A  V  S  C  S  G  F  R  L  K  A  C  L  E  L 661   TCATCGAGCTAAAACCTACTGTAATCAAAGGAAACGGTTCTGAGATTATTGCTCTCTCCT    720
        I  E  L  K  P  T  V  I  K  G  N  G  S  E  I  I  A  L  S  S 721   CTGCTTCACGTGGACAAACTAAGGGTGCTGATAGCTCACATGAATCAACAGACGCTATAG    780
        A  S  R  G  Q  T  K  G  A  D  S  S  H  E  S  T  D  A  I  E 781   AAGCTGCAAAGTCATTAGCGATGTCAAGTGGTGCTGTTGTTGCAGTGTCAGGAGCTGTTG    840
        A  A  K  S  L  A  M  S  S  G  A  V  V  A  V  S  G  A  V  D 841   ATATTGTTACTGATGGGAAACAGGTTATTGGTGTTCACAACGGGACGAAGATGATGCAAC    900
        I  V  T  D  G  K  Q  V  I  G  V  H  N  G  T  K  M  M  Q  Q 901   AGATTACTGCAACTGGTTGTTCTCTAGCTGGTTTGATTGTAGCGTTTCTTGCTATTGATT    960
        I  T  A  T  G  C  S  L  A  G  L  I  V  A  F  L  A  I  D  S 962   CATCACGGGTACTGGAAGCTACGGTTTCCGCTATGGCTGTCTTTGGCATTGCAGGTGAGT   1020
        S  R  V  L  E  A  T  V  S  A  M  A  V  F  G  I  A  G  E  L 1021   TGGGTGAAGCGATGGCGAATGGTCCAGCGTCATTGAGAATGCATTTGATAGATTGTCTTT   1080
        G  E  A  M  A  N  G  P  A  S  L  R  M  H  L  I  D  C  L  Y 1081   ATGGGTTGGATGAAACCACAGTGCTTAAACGTGTGAATGTGACCAGGTTGGGT TGA tgta  1140
        G  L  D  E  T  T  V  L  K  R  V  N  V  T  R  L  G 1141   catgaatcatcttctttgaataaagtttcttaagatatctctgcaatttcttgatcatt            1200

1201      Boxed sequence used to make Thi3-Ri construct                      1260
          agtatatcgtccagcttcaggtagataggagtgtcatggttatatagcttttgtggtcac 1261   catcttagactttaaggcaatgttcaaaaattacacttttaacaatcttagaagtttcat            1320

1321   ggctttggatgatttg ctttcgatcaataactgttacatacaacaacaaaagaacattca         1380

1381   cacacacgcacacatgtagaaatttgaaatctttttggtaaggctacttttgggttttgt           1439
```

TABLE 11

*Arabidopsis* pyruvate decarboxylase 2 (AtPDC2) coding and protein sequence. See also SEQ ID NO:26 (DNA) and SEQ ID NO:29 (protein).

```
   1 ATGGACACTAAGATCGGATCTATCGACGCGTGTAACCCGACCAACCACGATATCGGCGGT    60
     M   D   T   K   I   G   S   I   D   A   C   N   P   T   N   H   D   I   G   G

61 CCTCCAAACGGCGGAGTCTCCACCGTTCAAAACACAAGTCCACTTCACTCCACCACCGTC   120
     P   P   N   C   G   V   S   T   V   Q   N   T   S   P   L   H   S   T   T   V

121 AGCCCCTGCGACGCGACTCTTGGCCGTTACCTAGCAAGACGGTTAGTCGAAATCGGCGTC   180
     S   P   C   D   A   T   L   G   R   Y   L   A   R   R   L   V   E   I   G   V

181 ACCGATCTCTTCTCCGTTCCTGGTGATTTCAACCTGACGCTTCTCGATCACCTAATCGCC   240
     T   D   V   F   S   V   P   G   D   F   N   L   T   L   L   D   H   L   I   A

241 GAACCAAACCTCAAGCTGATCGGTTGCTGCAACGAGCTTAACGCCGGATACGCTGCTGAC   300
     E   P   N   L   K   L   I   G   C   C   N   E   L   N   A   G   Y   A   A   D

301 GGTTACGCTAGATCTCGCGGTGTTGGTGCGTGCGTCGTTACGTTCACCGTCGGTGGATTG   360
     G   Y   A   R   S   R   G   V   G   A   C   V   V   T   F   T   V   G   G   L

361 AGTGTTCTGAATGCGATCGCCGGTGCTTACAGTGAGAATCTGCCTCTGATTTGCATCGTC   420
     S   V   L   N   A   I   A   G   A   Y   S   E   N   L   P   L   I   C   I   V

421 GGTGGTCCAAACTCCAACGATTACGGTACCAATAGGATTCTTCATCATACAATTGGTTTA   480
     G   G   P   N   S   N   D   Y   G   T   N   R   I   L   H   H   T   I   G   L

481 CCTGATTTCACTCAACACCTTAGGTGTTTTCAAGCTGTTACTTGTTTTCAACCTGTGATT   540
     P   D   F   T   Q   E   L   R   C   F   Q   A   V   T   C   F   Q   A   V   I

541 AATAACTTAGAAGAGGCTCATGAACTTATCGATACTGCGATTTCAACTGCTTTGAAAGAA   600
     N   N   L   E   E   A   H   E   L   I   D   T   A   I   S   T   A   L   K   E

601 AGCAAACCTGTTTATATCAGTATCAGCTGTAATTTACCGGCGATTCCTCTTCCGACGTTT   660
     S   K   P   V   Y   I   S   I   S   C   N   L   P   A   I   P   L   P   T   F

661 AGTCGTCATCCTGTTCCGTTCATGCTTCCGATGAAGGTTAGCAATCAGATTGGTTTAGAT   720
     S   R   H   P   V   P   F   M   L   P   M   K   V   S   N   Q   I   G   L   D

721 GCGGCGGTGGAGGCAGCTGCTGAGTTCTTGAACAAAGCTGTGAAGCCAGTTCTTGTTGGT   780
     A   A   V   E   A   A   A   E   F   L   N   K   A   V   K   P   V   L   V   G

781 GGGCCGAAAATGCGGGTTGCGAAAGCCGCGGATGCTTTTGTTGAGCTTGCTGATGCTTCT   840
     G   P   K   M   R   V   A   K   A   A   D   A   F   V   E   L   A   D   A   S

841 GGCTATGGTCTTGCTGTGATGCCTTCTGCTAAAGGACAAGTACCTGAGCATCACAAGCAT   900
     G   Y   G   L   A   V   M   P   S   A   K   G   Q   V   P   E   H   H   K   H

901 TTTATAGGGACGTATTGGGGAGCTGTGAGTACAGCTTTTTGTGCTGAAATCGTTGAATCT   960
     F   I   G   T   Y   W   G   A   V   S   T   A   F   C   A   E   I   V   E   S

961 GCGGATGCTTATCTGTTTGCAGGTCCGATTTTCAACGATTACAGTTCTGTTGGGTATTCT  1020
     A   D   A   Y   L   F   A   G   P   I   F   N   D   Y   S   S   V   G   Y   S

1021 CTGCTTCTCAAGAAGGAGAAGGCAATCATCGTTCAGCCTGATCGGGTTACTATCGGTAAC  1080
     L   L   L   K   K   E   K   A   I   I   V   Q   P   D   R   V   T   I   G   N

1081 GGACCTGCGTTTGGATGTGTTCTTATGAAGGATTTTCTAAGCGAGTTGGCTAAACGAATT  1140
     G   P   A   F   G   C   V   L   M   K   D   F   L   S   E   L   A   K   R   I

1141 AAGCACAACAACACTTCTTATGAGAATTATCACAGGATCTATGTCCCAGAAGGAAAGCCT  1200
     K   H   N   N   T   S   Y   E   N   Y   H   R   I   Y   V   P   E   G   K   P

1201 TTGAGAGATAACCCGAATGAGTCTTTGAGGGTTAATGTACTGTTCCAACACATTCAGAAT  1260
     L   R   D   N   P   N   E   S   L   R   V   N   V   L   F   Q   H   I   Q   N

1261 ATGCTCTCTTCTGAGTCTGCTGTGCTTGCTGAGACAGGAGATTCCTGGTTCAACTGTCAG  1320
     M   L   S   S   E   S   A   V   L   A   E   T   G   D   S   W   F   N   C   Q

1321 AAGCTGAAGCTCCCTGAAGCATGCGGTTACGAATTCCAAATGCAGTACGCATCAATTGGC  1380
     K   L   K   L   P   E   G   C   G   Y   E   F   Q   M   Q   Y   G   S   I   G

1381 TGGTCAGTGCGTGCTACTCTAGGCTATGCTCAAGCCATGCCAAACAGGCGTGTCATTGCT  1440
     W   S   V   G   A   T   L   G   Y   A   Q   A   M   P   N   R   R   V   I   A

1441 TGTATTGGAGATGGTAGTTTCCAGGTAACCCCACAGGATGTATCTACGATGATACGGTGT  1500
     C   I   G   D   G   S   F   Q   V   T   A   Q   D   V   S   T   M   I   R   C
```

TABLE 11-continued

*Arabidopsis* pyruvate decarboxylase 2 (AtPDC2) coding and protein sequence. See also SEQ ID NO:26 (DNA) and SEQ ID NO:29 (protein).

```
1501 GGGCAAAAGACCATAATCTTCCTCATCAACAACGGAGGCTACACCATTcaaGTGGAAATT  1560
       G  Q  K  T  I  I  F  L  I  N  N  G  G  Y  T  I  Q  V  E  I 1561 CACGATGGTCCTTACAATGTCATAAAGAACTGGAACTACACAGCTTTTGTTGAGGCCATA  1620
       H  D  G  P  Y  N  V  I  K  N  W  N  Y  T  A  F  V  E  A  I 1621 CACAATGGAGAAGGAAAATGCTGGACTGCCAAGGTGAGATGCGAGGAGGAGTTAGTGAAA  1680
       H  N  G  E  G  K  C  W  T  A  K  V  R  C  E  E  E  L  V  K 1681 GCAATCAACACGGCAACCAATGAGGAAAAAGAGAGCTTTTGTTTCATTGAAGTGATAGTG  1740
       A  I  N  T  A  T  N  E  E  K  E  S  F  C  F  I  E  V  I  V 1741 CACAAAGACGATACAAGCAAGGAACTTTTGGAGTGGGGCTCTAGAGTCTCTGCTGCTAAT  1800
       H  K  D  D  T  S  K  E  L  L  E  W  G  S  R  V  S  A  A  N 1801 AGTCGTCCCCCAAATCCGCAGTAG                                       1824
       S  R  P  P  N  P  Q  *
```

What is claimed is:

1. A plant tissue-specific transcriptional regulatory system comprising a repressor protein coding sequence operably linked to a light activated aboveground plant tissue specific promoter, wherein the repressor protein comprises a nuclear translocation signal, and a functional sequence operably linked to a promoter sequence modified to comprise at least one operator sequence to which the repressor protein binds, such that the function sequence is expressed only in root tissue in which the repressor protein is not expressed, provided that the system comprises at least one sequence selected from the group consisting of the nuclear translocation sequence set forth in SEQ ID NO:9, the repressor protein set forth in SEQ ID NO:11, the regulated promoter sequence set forth in SEQ ID NO:12 and the mercury reductase coding sequence set forth in SEQ ID NO:13.

2. The plant tissue specific transcriptional regulatory system of claim 1, wherein said operator is a lac operator sequence, wherein said repressor protein is a lac repressor protein, and wherein the lac repressor protein binds to the operator sequence.

3. The tissue-specific transcriptional regulatory system of claim 1, wherein the nuclear localization signal has the amino acid sequence set forth in SEQ ID NO:9.

4. The tissue-specific transcriptional regulatory system of claim 2, wherein the repressor protein comprises the amino acid sequence set forth in SEQ ID NO:11.

5. The tissue-specific transcriptional regulatory system of claim 2, wherein the promoter is an Actin2 promoter from *Arabidopsis thaliana* and the lac operator sequence comprises the nucleotide sequence 5'-GTGGAATTGTGAGCGGATAACAATT-3' (SEQ ID NO:16).

6. The tissue-specific transcriptional regulatory system of claim 2, wherein the sequence of the regulated promoter is set forth in SEQ ID NO:12.

7. the tissue-specific transcriptional regulatory system of claim 1, wherein the functional sequence is a mercury reductase coding sequence.

8. The tissue specific transcriptional regulatory system of claim 7, wherein the mercury reductase coding sequence is as set forth in SEQ ID NO:13.

9. A transgenic plant, transgenic plant tissue, tranagenic plant cell or tranagenic seed comprising within its genome the transcriptional regulatory system of claim 1.

10. The transgenic plant, tranagenic plant tissue or tranagenic plant cell or transgenic plant seed of claim 9, wherein the functional sequence encodes a zinc transporter protein or a phosphate transporter protein.

11. The transgenic plant, transgenic plant tissue, tranagenic plant cell or transgenic seed of claim 9, wherein the functional sequence is a mercury reductase coding sequence.

12. The transgenic plant or seed or progeny thereof of claim 9, wherein said functional sequence confers resistance to a fungus, bacterium, virus or a nematode, thereby protecting said plant from infection by said fungus, bacterium, virus or nematode.

* * * * *

SEQUENCE LISTING

<160> NUMBER OF SEQ ID NOS: 29

<210> SEQ ID NO 1
<211> LENGTH: 53
<212> TYPE: DNA
<213> ORGANISM: Artificial
<220> FEATURE:
<223> OTHER INFORMATION: Oligonucleotide useful as a primer.

<400> SEQUENCE: 1
tagtaaggag gaaccacctc gaggccatgg gtaaaccagt aacgttatac gat        53

<210> SEQ ID NO 2
<211> LENGTH: 78
<212> TYPE: DNA
<213> ORGANISM: Artificial
<220> FEATURE:
<223> OTHER INFORMATION: Oligonucleotide useful as a primer.

<400> SEQUENCE: 2
atgtaagctt ggatcctcaa acctttctct tcttcttagg atgaacaaca gaagactgcc    60
cgctttccag tcgggaaa                                                  78

<210> SEQ ID NO 3
<211> LENGTH: 26
<212> TYPE: DNA
<213> ORGANISM: Artificial
<220> FEATURE:
<223> OTHER INFORMATION: Oligonucleotide used as a "clamp".

<400> SEQUENCE: 3
ggtacctgat ctcaaataca ttgata                                         26

<210> SEQ ID NO 4
<211> LENGTH: 99
<212> TYPE: DNA
<213> ORGANISM: Artificial
<220> FEATURE:
<223> OTHER INFORMATION: Oligonucleotide useful as a primer.

<400> SEQUENCE: 4
gccggagatt caaaacggct gatgaaagtg aggaggacaa cgagacaatt caattgttat    60
ccgctcacaa ttccacttat ataggcgggt ttatctctt                          99

<210> SEQ ID NO 5
<211> LENGTH: 99
<212> TYPE: DNA
<213> ORGANISM: Artificial
<220> FEATURE:
<223> OTHER INFORMATION: Oligonucleotide useful as a primer.

<400> SEQUENCE: 5
agccgttttg aatctccggc gacttgacag agaagaacaa ggatgtggaa ttgtgagcgg    60
ataacaattt aatccaggag attcattctc cgttttgaa                          99

<210> SEQ ID NO 6
<211> LENGTH: 23
<212> TYPE: DNA
<213> ORGANISM: Artificial
<220> FEATURE:
<223> OTHER INFORMATION: Oligonucleotide useful as a primer.

<400> SEQUENCE: 6
tagctataat cgagctaact gat                                           23

<210> SEQ ID NO 7
<211> LENGTH: 65
<212> TYPE: DNA
<213> ORGANISM: Artificial
<220> FEATURE:
<223> OTHER INFORMATION: Oliognucleotide useful as a primer.

<400> SEQUENCE: 7
tagagttcta gaataaagga ggaaaaaccg gtaccccatg ggattacgtc ctgtagaaac    60
cccaa                                                               65

<210> SEQ ID NO 8
<211> LENGTH: 50
<212> TYPE: DNA
<213> ORGANISM: Artificial
<220> FEATURE:
<223> OTHER INFORMATION: Oligonucleotide useful as a primer.

<400> SEQUENCE: 8
ttcgatctcg aggagctcgg atcctcattg tttgcctccc tgctgcggtt              50

<210> SEQ ID NO 9
<211> LENGTH: 12
<212> TYPE: PRT
<213> ORGANISM: Artificial
<220> FEATURE:
<223> OTHER INFORMATION: Amino acid sequence of nuclear localization
      signal.

<400> SEQUENCE: 9

Ser Ser Val Val His Pro Lys Lys Lys Arg Lys Val
1               5                   10

<210> SEQ ID NO 10
<211> LENGTH: 1122
<212> TYPE: DNA
<213> ORGANISM: Artificial
<220> FEATURE:
<223> OTHER INFORMATION: Sequence encoding LacIn repressor protein.

```
<400> SEQUENCE: 10
atgggtaaac cagtaacgtt atacgatgtc gcagagtatg ccggtgtctc ttatcagacc      60
gtttcccgcg tggtgaacca ggccagccac gtttctgcga aaacgcggga aaaagtggaa     120
gcggcgatgg cggagctgaa ttacattccc aaccgcgtgg cacaacaact ggcgggcaaa     180
cagtcgttgc tgattggcgt tgccacctcc agtctggccc tgcacgcgcc gtcgcaaatt     240
gtcgcggcga ttaaatctcg cgccgatcaa ctgggtgcca cgtggtggt gtcgatggta      300 gaacgaagcg gcgtcgaagc ctgtaaagcg gcggtgcaca atcttctcgc gaacgcgtc      360 agtgggctga tcattaacta tccgctggat gaccaggatg ccattgctgt ggaagctgcc     420
tgcactaatg ttccggcgtt atttcttgat gtctctgacc agacacccat caacagtatt     480
attttctccc atgaagacgg tacgcgactg gcgtggagc atctggtcgc attgggtcac      540
cagcaaatcg cgctgttagc gggcccatta agttctgtct cggcgcgtct cgtctggct      600 ggctggcata aatatctcac tcgcaatcaa attcagccga tagcggaacg ggaaggcgac     660
tggagtgcca tgtccggttt caacaaacc atgcaaatgc tgaatgaggg catcgttccc      720
actgcgatgc tggttgccaa cgatcagatg gcgctgggcg caatgcgcgc cattaccgag     780
tccgggctgc gcgttggtgc ggatatctcg gtagtgggat acgacgatac cgaagacagc     840
tcatgttata tcccgccgtt aaccaccatc aaacaggatt tcgcctgct ggggcaaacc      900 agcgtggacc gcttgctgca actctctcag gccaggcgg tgaagggcaa tcagctgttg      960
cccgtctcac tggtgaaaag aaaaaccacc ctggcgccca atacgcaaac cgcctctccc    1020
cgcgcgttgg ccgattcatt aatgcagctg gcacgacagg tttcccgact ggaaagcggg    1080
cagtcttctg ttgttcatcc taagaagaag agaaaggttt ga                        1122

<210> SEQ ID NO 11
<211> LENGTH: 373
<212> TYPE: PRT
<213> ORGANISM: Artificial
<220> FEATURE:
<223> OTHER INFORMATION: LacIn repressor protein.

<400> SEQUENCE: 11

Met Gly Lys Pro Val Thr Leu Tyr Asp Val Ala Glu Tyr Ala Gly Val
1               5                   10                  15

Ser Tyr Gln Thr Val Ser Arg Val Val Asn Gln Ala Ser His Val Ser
                20                  25                  30

Ala Lys Thr Arg Glu Lys Val Glu Ala Ala Met Ala Glu Leu Asn Tyr
            35                  40                  45

Ile Pro Asn Arg Val Ala Gln Gln Leu Ala Gly Lys Gln Ser Leu Leu
        50                  55                  60

Ile Gly Val Ala Thr Ser Ser Leu Ala Leu His Ala Pro Ser Gln Ile
65                  70                  75                  80

Val Ala Ala Ile Lys Ser Arg Ala Asp Gln Leu Gly Ala Ser Val Val
                85                  90                  95

Val Ser Met Val Glu Arg Ser Gly Val Glu Ala Cys Lys Ala Ala Val
            100                 105                 110

His Asn Leu Leu Ala Gln Arg Val Ser Gly Leu Ile Ile Asn Tyr Pro
        115                 120                 125

Leu Asp Asp Gln Asp Ala Ile Ala Val Glu Ala Ala Cys Thr Asn Val
    130                 135                 140

Pro Ala Leu Phe Leu Asp Val Ser Asp Gln Thr Pro Ile Asn Ser Ile
145                 150                 155                 160
```

```
Ile Phe Ser His Glu Asp Gly Thr Arg Leu Gly Val Glu His Leu Val
            165                 170                 175
Ala Leu Gly His Gln Gln Ile Ala Leu Leu Ala Gly Pro Leu Ser Ser
        180                 185                 190
Val Ser Ala Arg Leu Arg Leu Ala Gly Trp His Lys Tyr Leu Thr Arg
    195                 200                 205
Asn Gln Ile Gln Pro Ile Ala Glu Arg Glu Gly Asp Trp Ser Ala Met
210                 215                 220
Ser Gly Phe Gln Gln Thr Met Gln Met Leu Asn Glu Gly Ile Val Pro
225                 230                 235                 240
Thr Ala Met Leu Val Ala Asn Asp Gln Met Ala Leu Gly Ala Met Arg
                245                 250                 255
Ala Ile Thr Glu Ser Gly Leu Arg Val Gly Ala Asp Ile Ser Val Val
            260                 265                 270
Gly Tyr Asp Asp Thr Glu Asp Ser Ser Cys Tyr Ile Pro Pro Leu Thr
        275                 280                 285
Thr Ile Lys Gln Asp Phe Arg Leu Leu Gly Gln Thr Ser Val Asp Arg
    290                 295                 300
Leu Leu Gln Leu Ser Gln Gly Gln Ala Val Lys Gly Asn Gln Leu Leu
305                 310                 315                 320
Pro Val Ser Leu Val Lys Arg Lys Thr Thr Leu Ala Pro Asn Thr Gln
                325                 330                 335
Thr Ala Ser Pro Arg Ala Leu Ala Asp Ser Leu Met Gln Leu Ala Arg
            340                 345                 350
Gln Val Ser Arg Leu Glu Ser Gly Gln Ser Ser Val Val His Pro Lys
        355                 360                 365
Lys Lys Arg Lys Val
    370

<210> SEQ ID NO 12
<211> LENGTH: 1938
<212> TYPE: DNA
<213> ORGANISM: Artificial
<220> FEATURE:
<223> OTHER INFORMATION: A2pot casette.

<400> SEQUENCE: 12
tcattatgta agaaagtttt gacgaatatg gcacgacaaa atggctagac tcgatgtaat      60
tggtatctca actcaacatt atacttatac caaacattag ttagacaaaa tttaaacaac     120 tatttttat gtatgcaaga gtcagcatat gtataattga ttcagaatcg ttttgacgag      180
ttcggatgta gtagtagcca ttatttaatg tacatactaa tcgtgaatag tgaatatgat     240
gaaacattgt atcttattgt ataaatatcc ataaacacat catgaaagac actttctttc     300
acggtctgaa ttaattatga tacaattcta atagaaaacg aattaaatta cgttgaattg     360
tatgaaatct aattgaacaa gccaaccacg acgacgacta acgttgcctg gattgactcg     420
gtttaagtta accactaaaa aaacggagct gtcatgtaac acgcggatcg agcaggtcac     480
agtcatgaag ccatcaaagc aaaagaacta atccaagggc tgagatgatt aattagttta     540
aaaattagtt aaaagaacta atccaagggc tgagatgatt aattagttta aaaattagtt     600
aacacgaggg aaaaggctgt ctgacagcca ggtcacgtta tctttacctg tggtcgaaat     660
gattcgtgtc tgtcgatttt aattattttt ttgaaaggcc gaaaataaag ttgtaagaga     720
taaacccgcc tatataagtg gaattgtgag cggataacaa ttgaattgtc tcgttgtcct     780
cctcactttc atcagccgtt tgaatctcc ggcgacttga cagagaagaa caaggatgtg     840
```

```
gaattgtgag cggataacaa tttaatccag gagattcatt ctccgttttg aatcttcctc      900
aatctcatct tcttccgctc tttctttcca aggtaatagg aactttctgg atctacttta      960
tttgctggat ctcgatcttg tttctcaat tccttgaga tctggaattc gtttaatttg      1020
gatctgtgaa cctccactaa atcttttggt tttactagaa tcgatctaag ttgaccgatc     1080
agttagctcg attatagcta ccagaatttg gcttgacctt gatggagaga tccatgttca     1140
tgttacctgg gaaatgattt gtatatgtga attgaaatct gaactgttga agttagattg     1200
aatctgaaca ctgtcaatgt tagattgaat ctgaacactg tttaaggtta gatgaagttt     1260
gtgtatagat tcttcgaaac tttaggattt gtagtgtcgt acgttgaaca gaaagctatt     1320
tctgattcaa tcagggttta tttgactgta ttgaactctt tttgtgtgtt tgcagctcat     1380
aaaccatggg ggcccctcga ggcatgcgtc gacaagcttg atatcccccgg gggatcctct     1440 agactcggag gctctcaaga tcaaaggctt aaaaagctgg ggttttatga atgggatcaa     1500
agtttctttt tttcttttat atttgcttct ccatttgttt gtttcatttc ccttttgtt      1560 ttcgtttcta tgatgcactt gtgtgtgaca aactctctgg gttttttactt acgtctgcgt     1620 ttcaaaaaaa aaaaccgctt tcgttttgcg ttttagtccc attgttttgt agctctgagt     1680
gatcgaattg atgcctcttt attccttttg ttccctataa tttctttcaa aactcagaag     1740
aaaaaccttg aaactctttg caatgttaat ataagtattg tataagattt ttattgattt     1800
ggttattagt cttacttttg ctacctccat cttcacttgg aactgatatt ctgaatagtt     1860
aaagcgttac atgtcttcca ttcacaaatg aacttaaact agcacaaagt cagatatttt     1920
aagaccgcgg tggagctc                                                    1938
```

<210> SEQ ID NO 13
<211> LENGTH: 1698
<212> TYPE: DNA
<213> ORGANISM: Artificial
<220> FEATURE:
<223> OTHER INFORMATION: merA77 coding sequence.

<400> SEQUENCE: 13

```
atgggtagca ctctcaagat cactggtatg acttgtgact cttgtgcagt gcatgtcaag       60
gatgcactgg agaaagttcc aggtgtgcaa tctgctgatg tgagctatgc aaagggctct      120
gccaaattgg ccattgaagt tggcacttct ccagatgcac ttactgctgc tgttgcaggt      180
ctgggctatc gtgctactct tgcagatgca ccatctgtgt ctactccagg tggtctgctt      240
gataagatgc gtgacctgct tggtcgtaat gacaagactg ggagctctgg tgcactccac      300
attgctgtga ttggctctgg tggtgcagca atggcagcag cacttaaagc tgttgaacaa      360
ggtgctcgtg tgactctgat tgaacgtggc actattggtg gcacttgtgt taatgttggt      420
tgtgtgccaa gcaagatcat gattcgtgct gctcacattg ctcatcttcg tcgtgaatct      480
ccatttgatg gtgcattgc tgcaaccact ccaaccattc aacgtactgc actccttgca      540
caacaacaag cacgtgttga tgaacttcgt catgcaaagt atgaaggtat tcttgaaggt      600
aacccagcca tcactgtgct tcatggctct gcacgtttca aggacaaccg taacctcatt      660
gttcaactta tgatggtgg tgaacgtgtg gtggcttttg accgctgtct cattgccact      720
ggtgcaagcc cagctgctcc accaattcct ggtctcaagg acactcctta ctggacttcc      780
actgaagcac tagtgtctga gaccattcca aagcgtcttg cagtcattgg ctcctctgtg      840
gtggctcttg aacttgccca ggcctttgca cgtcttggtc taaagtgac cattctcgca      900 cgctccactc tcttctttcg tgaagaccca gctgtaggtg aagctgttac tgctgcattt      960
```

-continued

```
cgcatggaag gtattgaagt gcgtgagcat actcaagcaa gccaagttgc ctatatcaat    1020
ggtgaaggtg atggtgaatt cgtccttacc actgctcatg gtgaacttcg tgcagacaaa    1080
ctccttgttg caactggtcg tgcaccaaac actcgcaaac tggcacttga tgcaactggt    1140
gtgaccctta ctccacaagg tgctattgtg attgatccag gtatgcgtac ctctgtggaa    1200
cacatctatg cagctggtga ttgcactgat caaccacaat ttgtgtatgt tgctgctgct    1260
gctggtacac gtgctgctat caacatgact ggtggcgatg ctgccctcaa cctgaccgcg    1320
atgccggccg tggtgttcac cgacccgcaa gtggcgaccg tgggctacag cgaggcggag    1380
gcgcaccatg acggcatcaa aactgatagt cgcacgctaa cgctggacaa cgtgccgcgc    1440
gcgctcgcca acttcgacac gcgcggcttc atcaaactgg tggttgaaga aggcagcgga    1500
cgactgatcg gcgtgcaggc agtggccccg gaagcgggcg aactgatcca gacggccgca    1560
ctggcgattc gcaaccggat gacggtgcag gaactggccg accagttatt cccctacctg    1620
acgatggtcg aagggttgaa gctcgcggcg cagaccttca acaaggatgt gaagcagctt    1680
tcctgctgcg ccgggtga                                                 1698
```

<210> SEQ ID NO 14
<211> LENGTH: 7
<212> TYPE: PRT
<213> ORGANISM: Artificial
<220> FEATURE:
<223> OTHER INFORMATION: Amino acid sequence of nuclear localization
      signal of SV40 T antigen used in designed proteins.

<400> SEQUENCE: 14

Pro Lys Lys Lys Arg Lys Val
1               5

<210> SEQ ID NO 15
<211> LENGTH: 6
<212> TYPE: PRT
<213> ORGANISM: Artificial
<220> FEATURE:
<223> OTHER INFORMATION: Amino acid sequence of nuclear localizatio
      signal from ARP7 protein, used in construction of designed
      proteins.

<400> SEQUENCE: 15

Ser Val Val His Arg Lys
1               5

<210> SEQ ID NO 16
<211> LENGTH: 25
<212> TYPE: DNA
<213> ORGANISM: Artificial
<220> FEATURE:
<223> OTHER INFORMATION: Oligonucleotide sequence derived from wild-type
      lac operator.

<400> SEQUENCE: 16
gtggaattgt gagcggataa caatt                                          25

<210> SEQ ID NO 17
<211> LENGTH: 2263
<212> TYPE: DNA
<213> ORGANISM: Artificial
<220> FEATURE:
<223> OTHER INFORMATION: A12pt derived from Arabidopsis thaliana cloned
      into SalI/PstI of ACT 12term Bluescript KC.

<400> SEQUENCE: 17

```
ggtaccgggc cccccctcga ggtcgacatt tctctataaa ttactaattt tcttgtgaaa      60
ttttgaatat ttttcaacta ttatattttc acggattgaa tatacgaatt tttacggata     120
tagtggtcac tttttgctg tagttggtga cattttggg gtgtcataga agaacaaaat       180
tgttaatgca tttataattt tggatttagt gataattgaa gaattaaaaa ggttttatac     240
ctctatctct ctaatcatgc aagaaaatat tttaaaaga aaaattaaaa atagttcaac      300
tggacaacga aattatccta aaatagttat ttcttttgat ctaatccttc ttcttttaaa     360
ctttttttta cttgtttcta ctctacatgt ttcttgttat taggtaaagt attaggctct     420
tttttaaaa aaaatgctta atcctctggg tacctcgaaa agggaataat actctagtta      480
gataagtgca gcgatcaaca tgacaaaatg aatgaatgtt tgctttaatt ggtggctaaa     540
agctaaatac acagaaaagt caaaattcaa tctcaaaatc aaccctctg tctccaatgt      600
ccctaatcta taccaaaatg tcaatttatt ttcttgatca tatattccac taattaaaaa    660
taaatccttc tctaatgaaa tttgtcaagg ccttggaagc ctagttttaa atattaaatg     720
gaaactattt cttcaacaat cacactgtta tttagtattg ttgtatgttg ttcactactt    780
tcttcatttg ttttgtaaga aactataata agcaaaaaca cataataaag tctcatgtca    840
aataatgaat cttatgcaca tgcttgatta ttttacttgc acatatccct atcatcatta    900
tcacatttgt caattaccgt tatcatcatt actctcattc ttcccagaac ttttttcagca   960
atttccatac ctcacccact aagatctttt acccttttc ttaattatag tttggatagc    1020
actcttttac atagcactga aatttcggtt gaacacataa attactagaa actagaagga   1080
aatgttactg aaatttcact gattgtctaa aattgaataa tctaaagaaa atggcctttt   1140
aaccttttc ttaggcccaa atgggctcat taccactcat gcttgttcgg tgacccgatt    1200
cttccggtaa aacagagcct aaaccgtatt ttcaggttag gctggtgttt tcttaattct   1260
ccaacctaaa aatagatgga cacgtgtcta tagaggctga gatattggtc tcaatgaaga   1320
aaactaacgg ctcagacccg tgtatgaacg atattaaggg ccaaagttgc ttctgttttc   1380
cagaaatttt tgaaacccaa tttcagggca cgattccaca acctctttct tttcttctag   1440
atctacgtaa attcatcagg tacatgttat tttttttgtt tatttgatgt caaaattttg   1500
atcacaagga ggcaaaacca atataaatgt aacgctaatg cgtttgatta tggtatacgt   1560
aacgaattag atttaatggt tacattttat tgttttagat ttagttatga gattggcatt   1620
aattattggt gtttcctttg aatttgctat gtttcttatg ttgatgtaat cagctagaga   1680
ttgaaccatg ggggcccgca tgcctgcagc ccggggatc cactagtcct agatcaaaag    1740
tcaccaagta aaacaagagc ggtaaaaatt ttgatatcag ttttttcaccc tgaagccatt   1800
tgctataatt actcacaact tctctatttg tgttcttta tcttgtccc tcattgttca     1860
ttttaatctc tcttttgcaa caaagcaact taaaaaaaca gatcagtcat taacagaatg   1920
ttattattat atgtatacat attagtatac acccattatc ttcttctgag tttcctctct   1980
gtctctgctt agtttttttc aagcttggac ctcgatttca tttaaatctt ttatcatata   2040
agcataggat tctatacatc gatatatatt tattttgttg acactattca gcacatgcgt   2100
atgtcttatc ttgttagtat atgtaaccaa agacaaagaa aagatgctac aaattgtttt   2160
ctctgatgca gaaattcaat cttaaaattg tttttttttt caattgcaca aaaaatcatg   2220
tagtttgtaa attttctaaa caattttgat gatctttgag ctc                      2263
```

<210> SEQ ID NO 18
<211> LENGTH: 3357
<212> TYPE: DNA
<213> ORGANISM: Artificial
<220> FEATURE:
<223> OTHER INFORMATION: Chimeric sequence including coding sequence for lac repressor protein with nuclear localization signal.

<400> SEQUENCE: 18

```
ggtaccgggc cccccctcga ggtcgacatt tctctataaa attactaatt ttcttgtgaa      60
attttgaata tttttcaact attatatttt cacggattga atatacgaat ttttacggat     120
atagtggtca ctttttttgct gtagttggtg acatttttgg ggtgtcatag aagaacaaaa    180
ttgttaatgc atttataatt ttggatttag tgataattga agaattaaaa aggttttata     240
cctctatctc tctaatcatg caagaaaata ttttaaaaag aaaaattaaa aatagttcaa     300
ctggacaacg aaattatcct aaaatagtta tttcttttga tctaatcctt cttcttttaa     360
actttttttt acttgtttct actctacatg tttcttgtta ttaggtaaag tattaggctc     420
ttttttttaaa aaaaatgctt aatcctctgg gtacctcgaa aagggaataa tactctagtt    480
agataagtgc agcgatcaac atgacaaaat gaatgaatgt ttgctttaat tggtggctaa     540
aagctaaata cacagaaaag tcaaaattca atctcaaaat caaccctct gtctccaatg      600
tccctaatct ataccaaaat gtcaatttat tttcttgatc atatattcca ctaattaaaa     660
ataaatcctt ctctaatgaa atttgtcaag gccttggaag cctagtttta aatattaaat     720
ggaaactatt tcttcaacaa tcacactgtt atttagtatt gttgtatgtt gttcactact     780
ttcttcattt gttttgtaag aaactataat aagcaaaaac acataataaa gtctcatgtc     840
aaataatgaa tcttatgcac atgcttgatt attttacttg cacatatccc tatcatcatt     900
atcacatttg tcaattaccg ttatcatcat tactctcatt cttcccagaa cttttcagc     960
aatttccata cctcacccac taagatcttt tacccttttt cttaattata gtttggatag    1020
cactctttta catagcactg aaatttcggt tgaacacata aattactaga aactagaagg    1080
aaatgttact gaaatttcac tgattgtcta aaattgaata atctaaagaa aatggccttt    1140
taacctttt cttaggccca aatgggctca ttaccactca tgcttgttcg gtgacccgat    1200
tcttccggta aaacagagcc taaaccgtat tttcaggtta ggctggtgtt ttcttaattc   1260
tccaacctaa aaatagatgg acacgtgtct atagaggctg agatattggt ctcaatgaag   1320
aaaactaacg gctcagaccc gtgtatgaac gatattaagg gccaaagttg cttctgtttt   1380
ccagaaattt ttgaaaccca atttcagggc acgattccac aacctctttc ttttcttcta    1440
gatctacgta aattcatcag gtacatgtta tttttttgt ttatttgatg tcaaaatttt    1500
gatcacaagg aggcaaaacc aatataaatg taacgctaat gcgtttgatt atggtatacg    1560
taacgaatta gatttaatgg ttacatttta ttgttttaga tttagttatg agattggcat    1620
taattattgg tgtttccttt gaatttgcta tgtttcttat gttgatgtaa tcagctagag   1680
attgaaccat gggtaaacca gtaacgttat acgatgtcgc agagtatgcc ggtgtctctt   1740
atcagaccgt ttcccgcgtg gtgaaccagg ccagccacgt ttctgcgaaa acgcgggaaa   1800
aagtggaagc ggcgatggcg gagctgaatt acattcccaa ccgcgtggca caacaactgg   1860
cgggcaaaca gtcgttgctg attggcgttg ccacctccag tctggccctg cacgcgccgt   1920
cgcaaattgt cgcggcgatt aaatctcgcg ccgatcaact gggtgccagc gtggtggtgt   1980
cgatggtaga acgaagcggc gtcgaagcct gtaaagcggc ggtgcacaat cttctcgcgc   2040
aacgcgtcag tgggctgatc attaactatc cgctggatga ccaggatgcc attgctgtgg   2100
```

-continued

```
aagctgcctg cactaatgtt ccggcgttat ttcttgatgt ctctgaccag acacccatca    2160
acagtattat tttctcccat gaagacggta cgcgactggg cgtggagcat ctggtcgcat    2220
tgggtcacca gcaaatcgcg ctgttagcgg gcccattaag ttctgtctcg gcgcgtctgc    2280
gtctggctgg ctggcataaa tatctcactc gcaatcaaat tcagccgata gcggaacggg    2340
aaggcgactg gagtgccatg tccggttttc aacaaaccat gcaaatgctg aatgagggca    2400
tcgttcccac tgcgatgctg gttgccaacg atcagatggc gctgggcgca atgcgcgcca    2460
ttaccgagtc cgggctgcgc gttggtgcgg atatctcggt agtgggatac gacgataccg    2520
aagacagctc atgttatatc cgccgttaa ccaccatcaa acaggatttt cgcctgctgg     2580
ggcaaaccag cgtggaccgc ttgctgcaac tctctcaggg ccaggcggtg aagggcaatc    2640
agctgttgcc cgtctcactg gtgaaaagaa aaccaccct ggcgcccaat acgcaaaccg     2700
cctctccccg cgcgttggcc gattcattaa tgcagctggc acgacaggtt tcccgactgg    2760
aaagcgggca gtcttctgtt gttcatccta agaagaagag aaaggtttga ggatccacta    2820
gttctagatc aaaagtcaca agtaaaacaa gagcggtaaa aattttgata tcagtttttc    2880
accctgaagc catttgctat aattactcac aacttctcta tttgtgttct tttattcttg    2940
tccctcattg ttcattttaa tctctctttt gcaacaaagc aacttaaaaa aacagatcag    3000
tcattaacag aatgttatta ttatatgtat acatattagt atacacccat tatcttcttc    3060
tgagtttcct ctctgtctct gcttagtttt tttcaagctt ggacctcgat ttcatttaaa    3120
tcttttatca tataagcata ggattctata catcgatata tatttatttt gttgacacta    3180
ttcagcacat gcgtatgtct tatcttgtta gtatatgtaa ccaaagacaa agaaaagatg    3240
ctacaaattg ttttctctga tgcagaaatt caatcttaaa attgtttttt ttttcaattg    3300
cacaaaaaat catgtagttt gtaaattttc taaacaattt tgatgatctt tgagctc      3357
```

<210> SEQ ID NO 19
<211> LENGTH: 2259
<212> TYPE: DNA
<213> ORGANISM: Artificial
<220> FEATURE:
<223> OTHER INFORMATION: ACT12pot vector clone #5.

<400> SEQUENCE: 19

```
ggtaccgggc cccccctcga ggtcgacatt tctctataaa attactaatt ttcttgtgaa      60
attttgaata tttttcaact attatatttt cacggattga atatacgaat ttttacggat     120
atagtggtca ctttttgct gtagttggtg acatttttgg ggtgtcatag aagaacaaaa      180
ttgttaatgc atttataatt ttggatttag tgataattga agaattaaaa aggttttata     240
cctctatctc tctaatcatg caagaaaata ttttaaaaag aaaaattaaa aatagttcaa     300
ctggacaacg aaattatcct aaaatagtta tttcttttga tctaatcctt cttcttttaa     360 acttttttt acttgtttct actctacatg tttcttgtta ttaggtaaag tattaggctc      420 ttttttaaa aaaatgctt aatcctctgg gtacctcgaa aagggaataa tactctagtt       480
agataagtgc agcgatcaac atgacaaaat gaatgaatgt ttgctttaat tggtggctaa     540
aagctaaata cacagaaaag tcaaaattca atctcaaaat caaccctctct gtctccaatg    600 tccctaatct ataccaaaat gtcaatttat ttcttgatc atatattcca ctaattaaaa      660
ataaatcctt ctctaatgaa atttgtcaag gccttggaag cctagttttta aatattaaat    720 ggaaactatt tcttcaacaa tcacactgtt atttagtatt gttgtatgtt gttcactact     780
ttcttcattt gttttgtaag aaactataat aagcaaaaac acataataaa gtctcatgtc    840
```

```
aaataatgaa tcttatgcac atgcttgatt attttacttg cacatatccc tatcatcatt      900
atcacatttg tcaattaccg ttatcatcat tactctcatt cttcccagaa cttttttcagc     960
aatttccata cctcacccac taagatcttt taccctttt cttaattata gtttggatag      1020
cactcttta catagcactg aaatttcggt taaacacata aattactaga aactagaagg      1080
aaatgttact gaaatttcac tgattgtcta aaattgaata atctaaagaa aatggccttt      1140
taacctttt cttaggccca aatgggctca ttaccactca tgcttgttcg gtgacccgat      1200
tcttccggta aaacagagcc taaaccgtat tttcaggtta ggctggtgtt ttcttaattc      1260
tccaacctaa aaatagatgg acacgtgtct atagaggctg agatattggt ctcaatgaag     1320
aaaactaacg gctcagaccc gtgtatgaac gatattaagt ggaattgtga gcggataaca     1380
attgaaattt ttgaaaccca atttcagggc agtggaattg tgagcggata acaatttcta     1440
gatctacgta aattcatcag gtacatgtca tttttttgc ttatttgatg tcaaaatttt     1500
gatcacaagg aggcaaaacc aatataaatg taacgctaat gcgtttgatt atggtatacg     1560
taacgaatta gatttaatgg ttacatttta ttgtttaga tttagttatg agattggcat     1620
taattattgg tgtttccttt gaatttgcta tgtttcttat gttgatgtaa tcagctagag      1680
attgaaccat ggggcccgc atgcctgcag cccgggggat ccactagttc tagatcaaaa      1740
gtcaccaagt aaaacaagag cggtaaaaat tttgatatca gttttcacc ctgaagccat     1800
ttgctataat tactcacaac ttctctattt gtgttctttt attcttgtcc ctcattgttc      1860
attttaatct ctcttttgca acaaagcaac ttaaaaaaac agatcagtca ttaacagaat     1920
gttattatta tatgtataca tattagtata cacccattat cttcttctga gtttcctctc      1980
tgtctctgct tagttttttt caagcttgga cctcgattc acttaaatct tttatcatat     2040
aagcacagga ttctatacat cgatatatat ttatttttgtt gacactattc agcacatgcg     2100
tatgtcttat cttgttagta tatgtaacca aagacaaaga aaagatgcta caaattgttt     2160
tctctgatgc agaaattcaa tcttaaaatt gttttttttt tcaattgcac aaaaaatcat     2220
ttgtaaattt tctaaacaat tttgatgatc tttgagctc                           2259
```

<210> SEQ ID NO 20
<211> LENGTH: 4051
<212> TYPE: DNA
<213> ORGANISM: Artificial
<220> FEATURE:
<223> OTHER INFORMATION: A12pot::GUS in Bluescript KS.

<400> SEQUENCE: 20

```
ggtaccgggc cccccctcga ggtcgacatt tctctataaa attactaatt ttcttgtgaa       60
attttgaata tttttcaact attatattttt cacggattga atatacgaat ttttacggat      120
atagtggtca ctttttttgct gtagttggtg acattttttgg ggtgtcatag aagaacaaaa     180
ttgttaatgc atttataatt ttggattag tgataattga agaattaaaa aggttttata        240
cctctatctc tctaatcatg caagaaaata ttttaaaaag aaaaattaaa aatagttcaa        300
ctggacaacg aaattatcct aaaatagtta tttcttttga tctaatcctt cttcttttaa       360
acttttttt acttgtttct actctacatg tttcttgtta ttaggtaaag tattaggctc       420
tttttttaaa aaaaatgctt aatcctctgg gtacctcgaa aagggaataa tactctagtt        480
agataagtgc agcgatcaac atgacaaaat gaatgaatgt ttgctttaat tggtggctaa      540
aagctaaata cacagaaaag tcaaaattca atctcaaaat caaccctct gtctccaatg        600
tccctaatct ataccaaaat gtcaattat ttcttgatc atatattcca ctaattaaaa       660
```

-continued

```
ataaatcctt ctctaatgaa atttgtcaag gccttggaag cctagtttta aatattaaat    720
ggaaactatt tcttcaacaa tcacactgtt atttagtatt gttgtatgtt gttcactact    780
ttcttcattt gttttgtaag aaactataat aagcaaaaac acataataaa gtctcatgtc    840
aaataatgaa tcttatgcac atgcttgatt attttacttg cacatatccc tatcatcatt    900
atcacatttg tcaattaccg ttatcatcat tactctcatt cttcccagaa ctttttcagc    960
aatttccata cctcacccac taagatcttt tacccttttt cttaattata gtttggatag   1020
cactctttta catagcactg aaatttcggt tgaacacata aattactaga aactagaagg   1080
aaatgttact gaaatttcac tgattgtcta aaattgaata atctaaagaa aatggccttt   1140
taacctttt cttaggccca aatgggctca ttaccactca tgcttgttcg gtgacccgat    1200
tcttccggta aaacagagcc taaaccgtat tttcaggtta ggctggtgtt ttcttaattc   1260
tccaacctaa aaatagatgg acacgtgtct atagaggctg agatattggt ctcaatgaag   1320
aaaactaacg gctcagaccc gtgtatgaac gatattaagt ggaattgtga gcggataaca   1380
attgaaattt ttgaaaccca atttcagggc agtggaattg tgagcggata acaatttcta   1440
gatctacgta aattcatcag gtacatgtca ttttttttgc ttatttgatg tcaaaatttt   1500
gatcacaagg aggcaaaacc aatataaatg taacgctaat gcgtttgatt atggtatacg   1560
taacgaatta gatttaatgg ttacatttta ttgttttaga tttagttatg agattggcat   1620
taattattgg tgtttccttt gaatttgcta tgtttcttat gttgatgtaa tcagctagag   1680
attgaaccat gggattacgt cctgtagaaa ccccaacccg tgaaatcaaa aaactcgacg   1740
gcctgtgggc attcagtctg gatcgcgaaa actgtggaat tgatcagcgt tggtgggaaa   1800
gcgcgttaca agaaagccgg gcaattgctg tgccaggcag ttttaacgat cagttcgccg   1860
atgcagatat tcgtaattat gcgggcaacg tctggtatca gcgcgaagtc tttataccga   1920
aaggttgggc aggccagcgt atcgtgctgc gtttcgatgc ggtcactcat tacggcaaag   1980
tgtgggtcaa taatcaggaa gtgatggagc atcagggcgg ctatacgcca tttgaagccg   2040
atgtcacgcc gtatgttatt gccgggaaaa gtgtacgtat caccgtttgt gtgaacaacg   2100
aactgaactg gcagactatc ccgccgggaa tggtgattac cgacgaaaac ggcaagaaaa   2160
agcagtctta cttccatgat ttctttaact atgccggaat ccatcgcagc gtaatgctct   2220
acaccacgcc gaacacctgg gtggacgata tcaccgtggt gacgcatgtc gcgcaagact   2280
gtaaccacgc gtctgttgac tggcaggtgg tggccaatgg tgatgtcagc gttgaactgc   2340
gtgatgcgga tcaacaggtg gttgcaactg gacaaggcac tagcgggact tgcaagtgg    2400
tgaatccgca cctctggcaa ccgggtgaag gttatctcta tgaactgtgc gtcacagcca   2460
aaagccagac agagtgtgat atctacccgc ttcgcgtcgg catccggtca gtggcagtga   2520
agggcgaaca gttcctgatt aaccacaaac cgttctactt tactggcttt ggtcgtcatg   2580
aagatgcgga cttgcgtggc aaaggattcg ataacgtgct gatggtgcac gaccacgcat   2640
taatggactg gattggggcc aactcctacc gtacctcgca ttacccttac gctgaagaga   2700
tgctcgactg gcagatgaa catggcatcg tggtgattga tgaaactgct gctgtcggct    2760
ttaacctctc tttaggcatt ggtttcgaag cgggcaacaa gccgaaagaa ctgtacagcg   2820
aagaggcagt caacggggaa actcagcaag cgcacttaca ggcgattaaa gagctgatag   2880
cgcgtgacaa aaaccaccca agcgtggtga tgtggagtat tgccaacgaa ccggatccc    2940
gtccgcaagg tgcacgggaa tatttcgcgc cactggcgga agcaacgcgt aaactcgacc   3000
cgacgcgtcc gatcacctgc gtcaatgtaa tgttctgcga cgctcacacc gataccatca   3060
```

```
gcgatctctt tgatgtgctg tgcctgaacc gttattacgg atggtatgtc caaagcggcg    3120
atttggaaac ggcagagaag gtactggaaa agaacttct ggcctggcag agaaactgc     3180 atcagccgat tatcatcacc gaatacggcg tggatacgtt agccgggctg cactcaatgt    3240
acaccgacat gtggagtgaa gagtatcagt gtgcatggct ggatatgtat caccgcgtct    3300
ttgatcgcgt cagcgccgtc gtcggtgaac aggtatggaa tttcgccgat tttgcgacct    3360
cgcaaggcat attgcgcgtt ggcggtaaca agaaagggat cttcactcgc gaccgcaaac    3420
cgaagtcggc ggcttttctg ctgcaaaaac gctggactgg catgaacttc ggtgaaaaac    3480
cgcagcaggg aggcaaacaa tgaggatcca ctagttctag atcaaaagtc accaagtaaa    3540
acaagagcgg taaaaatttt gatatcagtt tttcaccctg aagccatttg ctataattac    3600
tcacaacttc tctatttgtg ttcttttatt cttgtccctc attgttcatt ttaatctctc    3660
ttttgcaaca aagcaactta aaaaaacaga tcagtcatta acagaatgtt attattatat    3720
gtatacatat tagtatacac ccattatctt cttctgagtt tcctctctgt ctctgcttag    3780
tttttttcaa gcttggacct cgatttcatt taaatctttt atcatataag cataggattc    3840
tatacatcga tatatattta ttttgttgac actattcagc acatgcgtat gtcttatctt    3900
gttagtatat gtaaccaaag acaaagaaaa gatgctacaa attgttttct ctgatgcaga    3960
aattcaatct taaaattgtt ttttttttca attgcacaaa aaatcatgta gtttgtaaat    4020
tttctaaaca attttgatga tctttgagct c                                   4051

<210> SEQ ID NO 21
<211> LENGTH: 80
<212> TYPE: DNA
<213> ORGANISM: Artificial
<220> FEATURE:
<223> OTHER INFORMATION: Oligonucleotide useful as a primer.

<400> SEQUENCE: 21 gaaattttg aaacccaatt tcagggcagt ggaattgtga gcggataaca atttctagat      60
ctacgtaaat tcatcaggta                                                 80

<210> SEQ ID NO 22
<211> LENGTH: 77
<212> TYPE: DNA
<213> ORGANISM: Artificial
<220> FEATURE:
<223> OTHER INFORMATION: Oligonucleotide useful as a primer.

<400> SEQUENCE: 22
tgccctgaaa ttgggtttca aaaatttcaa ttgttatccg ctcacaattc cacttaatat      60
cgttcataca cgggtct                                                    77

<210> SEQ ID NO 23
<211> LENGTH: 1576
<212> TYPE: DNA
<213> ORGANISM: Artificial
<220> FEATURE:
<223> OTHER INFORMATION: Actin 11 promoter terminator sequence.

<400> SEQUENCE: 23
gagctcgaat tctgttgtag aatacaacac attaagcgca attagcagaa acagtctctt      60
catctgccga tttccacttg tcactactcc aaaaacctcc caaccatttt ccaaaacaga    120
cacttttgcc atgtctacat ctttcccttc cccgaaaaac acatcacttc catcaacgga    180
gtaaatatcc ggcggcatat cgatgctcga gaccgtccta tcgagaaaag gcttagccgc    240
```

```
ttccgtgacc gccggcgttc gtggaccgtg agattgctga aacgagcgag aataagcaag      300
cctccgatca ttagcagcat atccgacatc gctgctccga tcatcaggga gctcgttatc      360
gcctcgagga ttaaaggaaa tggatctctc cattttcttc tttgatctta aagttccaac      420
ttcggcaaat actaaaatca acagtcagtc gtacaaagaa actctgctta tacagtaaag      480
tcaatgggcc actgttctaa gcccatatat aattttagaa gcccatagaa tacaaaagag      540
tcaagaagca ttgaccgcac aagaaaaaaa caattgttaa aaagggttgg ttagtgtgta      600
tgtatatatg aaatgcaaca acattatac agcccattaa atatggttgt tataggtaga       660
tgtccccatt aaggaacttt atccagccca ttaaattact ttacagagta aaagagagag      720
agaagattta cagttacgtt accaaatttt cgaaatgatt taattagtaa taaataaata      780
attaaatgtc agttactctc tttagaaagc taaataagac agctgtttcc accaacaacg      840
tgactggtcg tggggtcctc cttcgttcaa agtgatattc agaaatcaac ggctgagatc      900
ttctccatca atatttatta cgggcctatt ccttcctttt ttaaacttca attctccggc      960
tcacattctc ttcttcattc gctccgtttc tctctcaaaa actacacacc cgtaccacac     1020
caccaccctc ctcgtttcct cagagatccc ctctctaact tctaaggtaa tcacatttcc     1080
ataacgttcc atcgtcattg attcttcatt agtatgcgtt tatgaagctt tttcaattta     1140
attctctttg gtagatctta agattcctct gtttcttgca aaataaaggg ttcaattatg     1200
ctaatatttt ttatatcaat tttgacagga tatagaccat ggtctagaac tagtggatcc     1260
cccgggctgc aggattaagc tcaaatcaaa gtgatgaatg attgttctgt attggtaaag     1320
ccttttgttc atcgactttg ttgcaaaata ttcttttgtt ttctatgttt cttccaccact    1380
acattacatt tctttcttgt tgttatcctc ttttggtgtt tctgctatta atcgaaaaag     1440
aaattttctt ttcttagttt cttttttctc ctcttcttaa ttctgtgaag ataaaaaga      1500
aggatgaaac cagtggccag tgggcattgg atttggcttt ttattttagg caaaagacaa     1560
gcttggtacc caattc                                                    1576
```

<210> SEQ ID NO 24
<211> LENGTH: 2492
<212> TYPE: DNA
<213> ORGANISM: Arabidopsis thaliana

<400> SEQUENCE: 24

```
accaaaccaa accactcggt aaacttgtat agcctcttgt atatattatg atatatatca       60
ataataatta cacgtgtaat gtaagatgca ttttgatttg aagatgcatt atgctgattt      120
gtaaaacata aacggctttg gtccctttt agtgtgtccg aatgaataag gtgttcaaaa       180
tagcgtgtga tttgtaattt gtaatttgta attagtctga aacgttgtat atatgaatat      240
tcttcaatta tataaaagct tgctttcaaa tatatcaatt tatctatctt ttgattatat     300
tgtcccttt tcgtggacca caagtattaa cttatctcat acaaataatt cgtgcttaag      360
tttggtgtta aaattattga aaattgattt acattgaatt tttttcgcgg taattgataa     420
ttcatgaaaa tcgatgaaat ttactaattt tatttcacat taaagtcaat aaaatgggaa     480
aatatttgat gagaataaaa taaaataaaa taaagagaag ggacgagaaa tgaatagctt     540
aggaggaatt aggagttggc cggcgaattg gagaagtacg acggcgtcaa tgggaacgac     600
gacggagagc gttagaaagg ttccgcaagt tttaacagtg gcgggatcag attccggcgc     660
cggagctgga attcaagccg accttaaagt ctgcgcagct cgtggtgtgt attgcgcttc     720
cgtcataacc gcagtcactg ctcagaacac tcgaggagtt caatctgttc atcttcttcc     780
```

-continued

```
tccggaattt atctctgaac agctcaaatc cgtcctctct gacttcgaat tcgacgtcgt      840
gaagactggg atgcttcctt ctactgagat cgttgaggtc cttcttcaaa atctatcaga      900
ttttccagtt cgtggtagag attacctcgc tttgttctct ttggttgttg atcctgtgat      960
ggtatctact agtggtcacg ttttggctgg ttcttctatt ctctctatct ttagagagag     1020
attactacca attgctgaca taattacccc aaatgtgaaa gaggcttctg ctttacttga     1080
tggttttcgg attgagactg ttgcagaaat gcggtctgca gcaaagtcgt tgcatgaaat     1140
gggtcctaga ttcgtacttg ttaaaggtgg tgatcttcct gactcatcag attcagtaga     1200
tgtttacttt gatggcaagg agtttcatga actccgttct cctcgcatag ctacaagaaa     1260
tactcatggg actggttgca ctttggcttc ctgtattgca gctgagcttg caaaaggctc     1320
ttccatgctc tcagccgtca aggtggctaa acgctttgtc gataatgccc tagattacag     1380
caaagatatt gtcattggca gtgggatgca aggaccttttt gaccatttttt ttggtcttaa     1440 gaaggatcct caaagttctc gatgcagcat attcaatcca gatgacctgt ttctatatgc     1500
tgttacagat tctagaatga acaaaaaatg gaaccgttcc attgtggatg ccttgaaagc     1560
tgctatagag ggaggggcca ccatcataca actgaggttt gatcattttc ttgaagaagc     1620
aaaagcatgc attgatatat gccggtccca tggagttagt ttgctgataa acgacaggat     1680
cgacattgcc cttgcttgtg atgctgatgg agtccatgtt ggtcaatccg acatgccggt     1740
tgatctagtt cggtctcttc ttggcccgga caagatcata ggggtctcat gtaagacacc     1800
agaacaagct catcaagcat ggaaagatgg tgcggactac attgggtcag gaggagtttt     1860
tccaacgaac actaaggcca acaatcgtac cataggactt gatgggctaa agaagtatg     1920 tgaagcatca aaattaccgg ttgttgcaat cggaggcata gggatctcaa atgctgggtc     1980
tgttatgcag atcgatgcac cgaacctaaa aggtgtagca gttgtgtcag ctttgttcga     2040
ccaagattgt gttttgactc aagctaagaa gttgcataaa acgcttaaag agagcaaaag     2100
gggaatttga accaaaaggt gttttttagtt ttgtttttagg tgcttacaaa atgttgtaaa     2160
ccttttactt cttacttga tgtattttttt tttttttttt gagaaagcca gaaaagataa     2220
atagtaatga ttgctacaaa cattttttact tccaaaaact tccaacattc tcaaattctc     2280
caagagataa catttgtgta tttcatttgc cttcactcct ctaagaaatt tattgttaca     2340
ggcagcaatc tgaaaaatgg aacaaaattt accttttgaca aaggtatcta atgcttgctt     2400
acaaacaaac gatttaactt gcctctctat atacacatag ccactggaat ggtacaaaga     2460
agatgaggta tttgacatat tcttgttttt gt                                   2492
```

<210> SEQ ID NO 25
<211> LENGTH: 1439
<212> TYPE: DNA
<213> ORGANISM: Arabidopsis thaliana

<400> SEQUENCE: 25

```
tcggatgatc ctcaccgcac tttcaataga gtaaatagtt gtccaagaca cgaagaagat       60
aacggtactt tatgcttctg tatctttaga gagagttcca cttctacatt gtaacctgtg      120
actttgagag tgtttgttcc attgttgttg tagaaaaacc atctcaaagc tgagaaatga      180
aacgactcgg ttcattggtt gaagtctaaa ccggtataaa atcccggttt taatctaatc      240
tagaccaaac cgtgtttctt atatatattt gaatccgtga tttacgcacg actggttaaa      300
gcagaatgga atcaaaatca gaacaaaacg agtggagctc cggcgtgtgg gctcacttaa      360
ccgccgtacg gcaacaatcg ccgcttgttc agtgcatcac caacttcgtc tcgatggatc      420
```

```
tcgttgccaa cacgctttta tccgccggtg catctccagc gatggtccat tccgtcgttg    480
agattcctga tttcactcct catattcacg cgctctgcgt caacgtcgga acacttacac    540
ctgactggct tccgtcaatg aaagctgccg ctgaactcgc ttctcagctc cgaaagcctt    600
gggttcttga tcccgccgcc gtgagttgct ccggattccg attaaaagcg tgtttggagc    660
tcatcgagct aaaacctact gtaatcaaag gaaacggttc tgagattatt gctctctcct    720
ctgcttcacg tggacaaact aagggtgctg atagctcaca tgaatcaaca gacgctatag    780
aagctgcaaa gtcattagcg atgtcaagtg gtgctgttgt tgcagtgtca ggagctgttg    840
atattgttac tgatgggaaa caggttattg gtgttcacaa cgggacgaag atgatgcaac    900
agattactgc aactggttgt tctctagctg gtttgattgt agcgtttctt gctattgatt    960
catcacgggt actggaagct acggtttccg ctatggctgt cttggcatt gcaggtgagt    1020 tgggtgaagc gatggcgaat ggtccagcgt cattgagaat gcatttgata gattgtcttt    1080
atgggttgga tgaaaccaca gtgcttaaac gtgtgaatgt gaccaggttg ggttgatgta    1140
catgaatcat cttctttgaa taaagtttct taagatatct ctgcaatttt cttgatcatt    1200
agtatatcgt ccagcttcag gtagatagga gtgtcatggt tatatagctt ttgtggtcac    1260
catcttagac tttaaggcaa tgttcaaaaa ttacactttt aacaatctta gaagtttcat    1320
ggctttggat gatttgcttt cgatcaataa ctgttacata caacaacaaa gaacattca    1380 cacacacgca cacatgtaga aatttgaaat cttttggtaa ggctacttt gggttttgt    1439
```

```
<210> SEQ ID NO 26
<211> LENGTH: 1824
<212> TYPE: DNA
<213> ORGANISM: Arabidopsis thaliana

<400> SEQUENCE: 26
atggacacta agatcggatc tatcgacgcg tgtaacccga ccaaccacga tatcggcggt     60
cctccaaacg gcggagtctc caccgttcaa aacacaagtc cacttcactc caccaccgtc    120 agccctgcg acgcgactct ggccgttac ctagcaagac ggttagtcga atcggcgtc     180 accgatgtct tctccgttcc tggtgatttc aacctgacgc ttctcgatca cctaatcgcc    240
gaaccaaacc tcaagctgat cggttgctgc aacgagctta cgccggata cgctgctgac    300 ggttacgcta gatctcgcgg tgttggtgcg tgcgtcgtta cgttcaccgt cggtggattg    360
agtgttctga atgcgatcgc cggtgcttac agtgagaatc tgcctctgat ttgcatcgtc    420
ggtggtccaa actccaacga ttacggtacc aataggattc ttcatcatac aattggttta    480
cctgatttca ctcaagagct taggtgtttt caagctgtta cttgttttca agctgtgatt    540
aataacttag aagaggctca tgaacttatc gatactgcga tttcaactgc tttgaaagaa    600
agcaaacctg tttatatcag tatcagctgt aatttaccgg cgattcctct tccgacgttt    660
agtcgtcatc ctgttccgtt catgcttccg atgaaggtta gcaatcagat tggtttagat    720
gcggcggtgg aggcagctgc tgagttcttg aacaaagctg tgaagccagt tcttgttggt    780
gggccgaaaa tgcgggttgc gaaagccgcg atgcttttg ttgagcttgc tgatgcttct    840
ggctatggtc ttgctgtgat gccttctgct aaaggacaag tacctgagca tcacaagcat    900
tttataggga cgtattgggg agctgtgagt acagctttt gtgctgaaat cgttgaatct    960
gcggatgctt atctgtttgc aggtccgatt ttcaacgatt acagttctgt tgggtattct   1020
ctgcttctca gaaggagaa ggcaatcatc gttcagcctg atcgggttac tatcggtaac   1080
ggacctgcgt ttggatgtgt tcttatgaag gatttcctaa gcgagttggc taaacgaatt   1140
```

-continued

```
aagcacaaca acacttctta tgagaattat cacaggatct atgtcccaga aggaaagcct    1200
ttgagagata acccgaatga gtctttgagg gttaatgtac tgttccaaca cattcagaat    1260
atgctctctt ctgagtctgc tgtgcttgct gagacaggag attcctggtt caactgtcag    1320
aagctgaagc tccctgaagg atgcggttac gaattccaaa tgcagtacgg atcaattggc    1380
tggtcagtgg gtgctactct aggctatgct caagccatgc caaacaggcg tgtcattgct    1440
tgtattggag atggtagttt ccaggtaacc gcacaggatg tatctacgat gatacggtgt    1500
gggcaaaaga ccataatctt cctcatcaac aacggaggct acaccattca agtggaaatt    1560
cacgatggtc cttacaatgt cataaagaac tggaactaca cagcttttgt tgaggccata    1620
cacaatggag aaggaaaatg ctggactgcc aaggtgagat gcgaggagga gttagtgaaa    1680
gcaatcaaca cggcaaccaa tgaggaaaaa gagagctttt gtttcattga agtgatagtg    1740
cacaaagacg atacaagcaa ggaacttttg gagtggggct ctagagtctc tgctgctaat    1800
agtcgtcccc caaatccgca gtag                                           1824
```

<210> SEQ ID NO 27
<211> LENGTH: 506
<212> TYPE: PRT
<213> ORGANISM: Arabidopsis thaliana

<400> SEQUENCE: 27

```
Met Gly Thr Thr Thr Glu Ser Val Arg Lys Val Pro Gln Val Leu Thr
  1               5                  10                  15

Val Ala Gly Ser Asp Ser Gly Ala Gly Ala Gly Ile Gln Ala Asp Leu
             20                  25                  30

Lys Val Cys Ala Ala Arg Gly Val Tyr Cys Ala Ser Val Ile Thr Ala
         35                  40                  45

Val Thr Ala Gln Asn Thr Arg Gly Val Gln Ser Val His Leu Leu Pro
     50                  55                  60

Pro Glu Phe Ile Ser Glu Gln Leu Lys Ser Val Leu Ser Asp Phe Glu
 65                  70                  75                  80

Phe Asp Val Val Lys Thr Gly Met Leu Pro Ser Thr Glu Ile Val Glu
                 85                  90                  95

Val Leu Leu Gln Asn Leu Ser Asp Phe Pro Val Arg Gly Arg Asp Tyr
            100                 105                 110

Leu Ala Leu Phe Ser Leu Val Val Asp Pro Val Met Val Ser Thr Ser
        115                 120                 125

Gly His Val Leu Ala Gly Ser Ser Ile Leu Ser Ile Phe Arg Glu Arg
    130                 135                 140

Leu Leu Pro Ile Ala Asp Ile Ile Thr Pro Asn Val Lys Glu Ala Ser
145                 150                 155                 160

Ala Leu Leu Asp Gly Phe Arg Ile Glu Thr Val Ala Glu Met Arg Ser
                165                 170                 175

Ala Ala Lys Ser Leu His Glu Met Gly Pro Arg Phe Val Leu Val Lys
            180                 185                 190

Gly Gly Asp Leu Pro Asp Ser Ser Asp Ser Val Asp Val Tyr Phe Asp
        195                 200                 205

Gly Lys Glu Phe His Glu Leu Arg Ser Pro Arg Ile Ala Thr Arg Asn
    210                 215                 220

Thr His Gly Thr Gly Cys Thr Leu Ala Ser Cys Ile Ala Ala Glu Leu
225                 230                 235                 240

Ala Lys Gly Ser Ser Met Leu Ser Ala Val Lys Val Ala Lys Arg Phe
                245                 250                 255
```

```
Val Asp Asn Ala Leu Asp Tyr Ser Lys Asp Ile Val Ile Gly Ser Gly
            260                 265                 270

Met Gln Gly Pro Phe Asp His Phe Gly Leu Lys Lys Asp Pro Gln
        275                 280                 285

Ser Ser Arg Cys Ser Ile Phe Asn Pro Asp Leu Phe Leu Tyr Ala
    290                 295                 300

Val Thr Asp Ser Arg Met Asn Lys Lys Trp Asn Arg Ser Ile Val Asp
305                 310                 315                 320

Ala Leu Lys Ala Ala Ile Glu Gly Gly Ala Thr Ile Ile Gln Leu Arg
                325                 330                 335

Phe Asp His Phe Leu Glu Glu Ala Lys Ala Cys Ile Asp Ile Cys Arg
            340                 345                 350

Ser His Gly Val Ser Leu Leu Ile Asn Asp Arg Ile Asp Ile Ala Leu
            355                 360                 365

Ala Cys Asp Ala Asp Gly Val His Val Gly Gln Ser Asp Met Pro Val
        370                 375                 380

Asp Leu Val Arg Ser Leu Leu Gly Pro Asp Lys Ile Ile Gly Val Ser
385                 390                 395                 400

Cys Lys Thr Pro Glu Gln Ala His Gln Ala Trp Lys Asp Gly Ala Asp
                405                 410                 415

Tyr Ile Gly Ser Gly Gly Val Phe Pro Thr Asn Thr Lys Ala Asn Asn
            420                 425                 430

Arg Thr Ile Gly Leu Asp Gly Leu Lys Glu Val Cys Glu Ala Ser Lys
        435                 440                 445

Leu Pro Val Val Ala Ile Gly Gly Ile Gly Ile Ser Asn Ala Gly Ser
    450                 455                 460

Val Met Gln Ile Asp Ala Pro Asn Leu Lys Gly Val Ala Val Val Ser
465                 470                 475                 480

Ala Leu Phe Asp Gln Asp Cys Val Leu Thr Gln Ala Lys Lys Leu His
                485                 490                 495

Lys Thr Leu Lys Glu Ser Lys Arg Gly Ile
            500                 505

<210> SEQ ID NO 28
<211> LENGTH: 276
<212> TYPE: PRT
<213> ORGANISM: Arabidopsis thaliana

<400> SEQUENCE: 28

Met Glu Ser Lys Ser Glu Gln Asn Glu Trp Ser Ser Gly Val Trp Ala
1               5                   10                  15

His Leu Thr Ala Val Arg Gln Gln Ser Pro Leu Val Gln Cys Ile Thr
            20                  25                  30

Asn Phe Val Ser Met Asp Leu Val Ala Asn Thr Leu Leu Ser Ala Gly
        35                  40                  45

Ala Ser Pro Ala Met Val His Ser Val Val Glu Ile Pro Asp Phe Thr
    50                  55                  60

Pro His Ile His Ala Leu Cys Val Asn Val Gly Thr Leu Thr Pro Asp
65                  70                  75                  80

Trp Leu Pro Ser Met Lys Ala Ala Glu Leu Ala Ser Gln Leu Arg
                85                  90                  95

Lys Pro Trp Val Leu Asp Pro Ala Ala Val Ser Cys Ser Gly Phe Arg
            100                 105                 110

Leu Lys Ala Cys Leu Glu Leu Ile Glu Leu Lys Pro Thr Val Ile Lys
        115                 120                 125
```

```
Gly Asn Gly Ser Glu Ile Ile Ala Leu Ser Ser Ala Ser Arg Gly Gln
        130                 135                 140

Thr Lys Gly Ala Asp Ser Ser His Glu Ser Thr Asp Ala Ile Glu Ala
145                 150                 155                 160

Ala Lys Ser Leu Ala Met Ser Ser Gly Ala Val Val Ala Val Ser Gly
                165                 170                 175

Ala Val Asp Ile Val Thr Asp Gly Lys Gln Val Ile Gly Val His Asn
                180                 185                 190

Gly Thr Lys Met Met Gln Gln Ile Thr Ala Thr Gly Cys Ser Leu Ala
            195                 200                 205

Gly Leu Ile Val Ala Phe Leu Ala Ile Asp Ser Ser Arg Val Leu Glu
        210                 215                 220

Ala Thr Val Ser Ala Met Ala Val Phe Gly Ile Ala Gly Glu Leu Gly
225                 230                 235                 240

Glu Ala Met Ala Asn Gly Pro Ala Ser Leu Arg Met His Leu Ile Asp
                245                 250                 255

Cys Leu Tyr Gly Leu Asp Glu Thr Thr Val Leu Lys Arg Val Asn Val
                260                 265                 270

Thr Arg Leu Gly
            275

<210> SEQ ID NO 29
<211> LENGTH: 605
<212> TYPE: PRT
<213> ORGANISM: Arabidopsis thaliana

<400> SEQUENCE: 29

Met Asp Thr Lys Ile Gly Ser Ile Asp Ala Cys Asn Pro Thr Asn His
1               5                   10                  15

Asp Ile Gly Gly Pro Pro Asn Gly Val Ser Thr Val Gln Asn Thr
            20                  25                  30

Ser Pro Leu His Ser Thr Thr Val Ser Pro Cys Asp Ala Thr Leu Gly
                35                  40                  45

Arg Tyr Leu Ala Arg Arg Leu Val Glu Ile Gly Val Thr Asp Val Phe
        50                  55                  60

Ser Val Pro Gly Asp Phe Asn Leu Thr Leu Leu Asp His Leu Ile Ala
65                  70                  75                  80

Glu Pro Asn Leu Lys Leu Ile Gly Cys Cys Asn Glu Leu Asn Ala Gly
                85                  90                  95

Tyr Ala Ala Asp Gly Tyr Ala Arg Ser Arg Gly Val Gly Ala Cys Val
                100                 105                 110

Val Thr Phe Thr Val Gly Gly Leu Ser Val Leu Asn Ala Ile Ala Gly
            115                 120                 125

Ala Tyr Ser Glu Asn Leu Pro Leu Ile Cys Ile Val Gly Gly Pro Asn
        130                 135                 140

Ser Asn Asp Tyr Gly Thr Asn Arg Ile Leu His His Thr Ile Gly Leu
145                 150                 155                 160

Pro Asp Phe Thr Gln Glu Leu Arg Cys Phe Gln Ala Val Thr Cys Phe
                165                 170                 175

Gln Ala Val Ile Asn Asn Leu Glu Glu Ala His Glu Leu Ile Asp Thr
                180                 185                 190

Ala Ile Ser Thr Ala Leu Lys Glu Ser Lys Pro Val Tyr Ile Ser Ile
            195                 200                 205

Ser Cys Asn Leu Pro Ala Ile Pro Leu Pro Thr Phe Ser Arg His Pro
        210                 215                 220
```

-continued

```
Val Pro Phe Met Leu Pro Met Lys Val Ser Asn Gln Ile Gly Leu Asp
225                 230                 235                 240

Ala Ala Val Glu Ala Ala Glu Phe Leu Asn Lys Ala Val Lys Pro
            245                 250                 255

Val Leu Val Gly Gly Pro Lys Met Arg Val Ala Lys Ala Ala Asp Ala
            260                 265                 270

Phe Val Glu Leu Ala Asp Ala Ser Gly Tyr Gly Leu Ala Val Met Pro
            275                 280                 285

Ser Ala Lys Gly Gln Val Pro Glu His His Lys His Phe Ile Gly Thr
            290                 295                 300

Tyr Trp Gly Ala Val Ser Thr Ala Phe Cys Ala Glu Ile Val Glu Ser
305                 310                 315                 320

Ala Asp Ala Tyr Leu Phe Ala Gly Pro Ile Phe Asn Asp Tyr Ser Ser
                325                 330                 335

Val Gly Tyr Ser Leu Leu Leu Lys Lys Glu Lys Ala Ile Ile Val Gln
            340                 345                 350

Pro Asp Arg Val Thr Ile Gly Asn Gly Pro Ala Phe Gly Cys Val Leu
            355                 360                 365

Met Lys Asp Phe Leu Ser Glu Leu Ala Lys Arg Ile Lys His Asn Asn
            370                 375                 380

Thr Ser Tyr Glu Asn Tyr His Arg Ile Tyr Val Pro Glu Gly Lys Pro
385                 390                 395                 400

Leu Arg Asp Asn Pro Asn Glu Ser Leu Arg Val Asn Val Leu Phe Gln
                405                 410                 415

His Ile Gln Asn Met Leu Ser Ser Glu Ser Ala Val Leu Ala Glu Thr
            420                 425                 430

Gly Asp Ser Trp Phe Asn Cys Gln Lys Leu Lys Leu Pro Glu Gly Cys
            435                 440                 445

Gly Tyr Glu Phe Gln Met Gln Tyr Gly Ser Ile Gly Trp Ser Val Gly
            450                 455                 460

Ala Thr Leu Gly Tyr Ala Gln Ala Met Pro Asn Arg Arg Val Ile Ala
465                 470                 475                 480

Cys Ile Gly Asp Gly Ser Phe Gln Val Thr Ala Gln Asp Val Ser Thr
            485                 490                 495

Met Ile Arg Cys Gly Gln Lys Thr Ile Ile Phe Leu Ile Asn Asn Gly
            500                 505                 510

Gly Tyr Thr Ile Gln Val Glu Ile His Asp Gly Pro Tyr Asn Val Ile
            515                 520                 525

Lys Asn Trp Asn Tyr Thr Ala Phe Val Glu Ala Ile His Asn Gly Glu
530                 535                 540

Gly Lys Cys Trp Thr Ala Lys Val Arg Cys Glu Glu Glu Leu Val Lys
545                 550                 555                 560

Ala Ile Asn Thr Ala Thr Asn Glu Glu Lys Glu Ser Phe Cys Phe Ile
                565                 570                 575

Glu Val Ile His Lys Asp Asp Thr Ser Lys Glu Leu Leu Glu Trp Gly
            580                 585                 590

Ser Arg Val Ser Ala Ala Ser Arg Pro Pro Asn Pro Gln
            595                 600                 605
```